US009597387B2

(12) United States Patent
Urwyler et al.

(10) Patent No.: US 9,597,387 B2
(45) Date of Patent: Mar. 21, 2017

(54) TARGETS OF *ACINETOBACTER BAUMANNII*

(71) Applicant: Aridis Pharmaceuticals, San Jose, CA (US)

(72) Inventors: Simon Urwyler, Bern (CH); Markus Haake, Bern (CH); Michael Rodolf, Ittigen (CH)

(73) Assignee: Aridis Pharmaceuticals, Inc., San Jose, CA (US)

( * ) Notice: Subject to any disclaimer, the term of this patent is extended or adjusted under 35 U.S.C. 154(b) by 0 days.

(21) Appl. No.: 14/362,058

(22) PCT Filed: Nov. 29, 2012

(86) PCT No.: PCT/EP2012/004939
§ 371 (c)(1),
(2) Date: May 30, 2014

(87) PCT Pub. No.: WO2013/079207
PCT Pub. Date: Jun. 6, 2013

(65) Prior Publication Data
US 2015/0023999 A1    Jan. 22, 2015

(30) Foreign Application Priority Data

Nov. 30, 2011  (EP) .................................. 11191320

(51) Int. Cl.
*A61K 39/104* (2006.01)
*C07K 14/21* (2006.01)
*C07K 16/12* (2006.01)
*C07K 14/22* (2006.01)
*A61K 39/00* (2006.01)

(52) U.S. Cl.
CPC ........ *A61K 39/1045* (2013.01); *A61K 39/104* (2013.01); *C07K 14/212* (2013.01); *C07K 14/22* (2013.01); *C07K 16/1217* (2013.01); *A61K 2039/55555* (2013.01)

(58) Field of Classification Search
None
See application file for complete search history.

(56) References Cited

U.S. PATENT DOCUMENTS

| 6,562,958 | B1  | 5/2003 | Breton et al. |
| 6,713,062 | B1  | 3/2004 | Merchant |
| 7,262,050 | B2  | 8/2007 | Adair et al. |
| 2005/0042664 | A1* | 2/2005 | Wu ...................... C07K 16/465 |
|  |  |  | 435/6.16 |

FOREIGN PATENT DOCUMENTS

| EP | 1580195 A1 | 9/2005 |
| ES | 2366735 | * 10/2011 |
| WO | WO 02/077183 A2 | 10/2002 |
| WO | WO 2011/125015 A2 | 10/2011 |

OTHER PUBLICATIONS

Uniprot Accession No. D0CDE3 "Porin B" Acinetobacter baumannii Nov. 24, 2009.*
Siddiqui et al. Indian J Pharm Science, Jan.-Feb. 2010:72(1):12-17.*
Eveillard, et al. (2010) "The virulence variability of different Acinetobacter baumannii strains in experimental pneumonia." *J Infect.*, 60(2):154-61.
Hugh and Reese (1967) "Designation of the Type Strain for Bacterium Anitratum Schaub and Hauber 1948." *Int J Syst Bacteriol.*, 17(3):245-254.
McConnell and Pachón (2011) "Expression, purification, and refolding of biologically active Acinetobacter baumannii OmpA from *Escherichia coli* inclusion bodies." *Protein Expr Purif.*, 77(1):98-103.
Pantophlet, et al. (2002) "Identification of Acinetobacter isolates from species belonging to the Acinetobacter calcoaceticus-Acinetobacter baumannii complex with monoclonal antibodies specific for O Antigens of their lipopolysaccharides." *Clin Diagn Lab Immunol.*, 9(1):60-65.
Wang, et al. (2007) "MMDB: annotating protein sequences with Entrez's 3D-structure database." *Nucleic Acids Res.*, 35(Database issue):D298-300.
International Search Report dated Feb. 20, 2013, from corresponding International Application No. PCT/EP2012/004939.

* cited by examiner

*Primary Examiner* — Oluwatosin Ogunbiyi
(74) *Attorney, Agent, or Firm* — Quine Intellectual Property Law Group P.C.

(57) ABSTRACT

The present invention provides antigenic polypeptides expressed during an infection by a pathogenic organism, such as *Acinetobacter* and compositions comprising these polypeptides. The invention further provides compositions for use in treating, preventing or detecting a bacterial infection, in particular vaccine compositions using the antigenic polypeptides. The invention further provides antibodies directed to said antigenic polypeptides.

6 Claims, 14 Drawing Sheets

Figure 1: IgG titres in sera from convalescent *A. baumannii* patients

Figure 2: ELISA from rabbit sera

Figure 3: Immunoblot analysis

Figure 4: Immunoblot analysis

Figure 5: Immunoblot analysis

Figure 6: FACS analysis

Figure 7: FACS analysis

Figure 9: Bactericidal assay

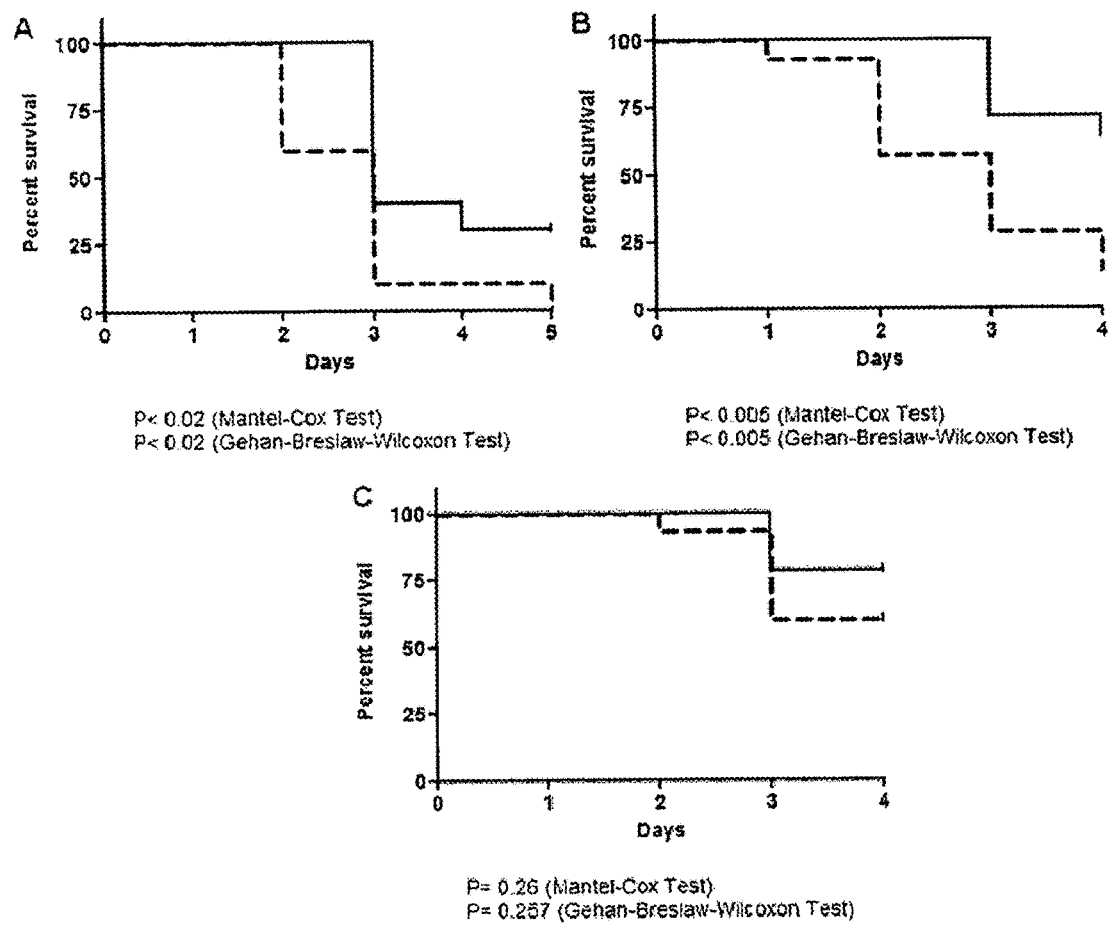
Figure 11: Passive Immunization

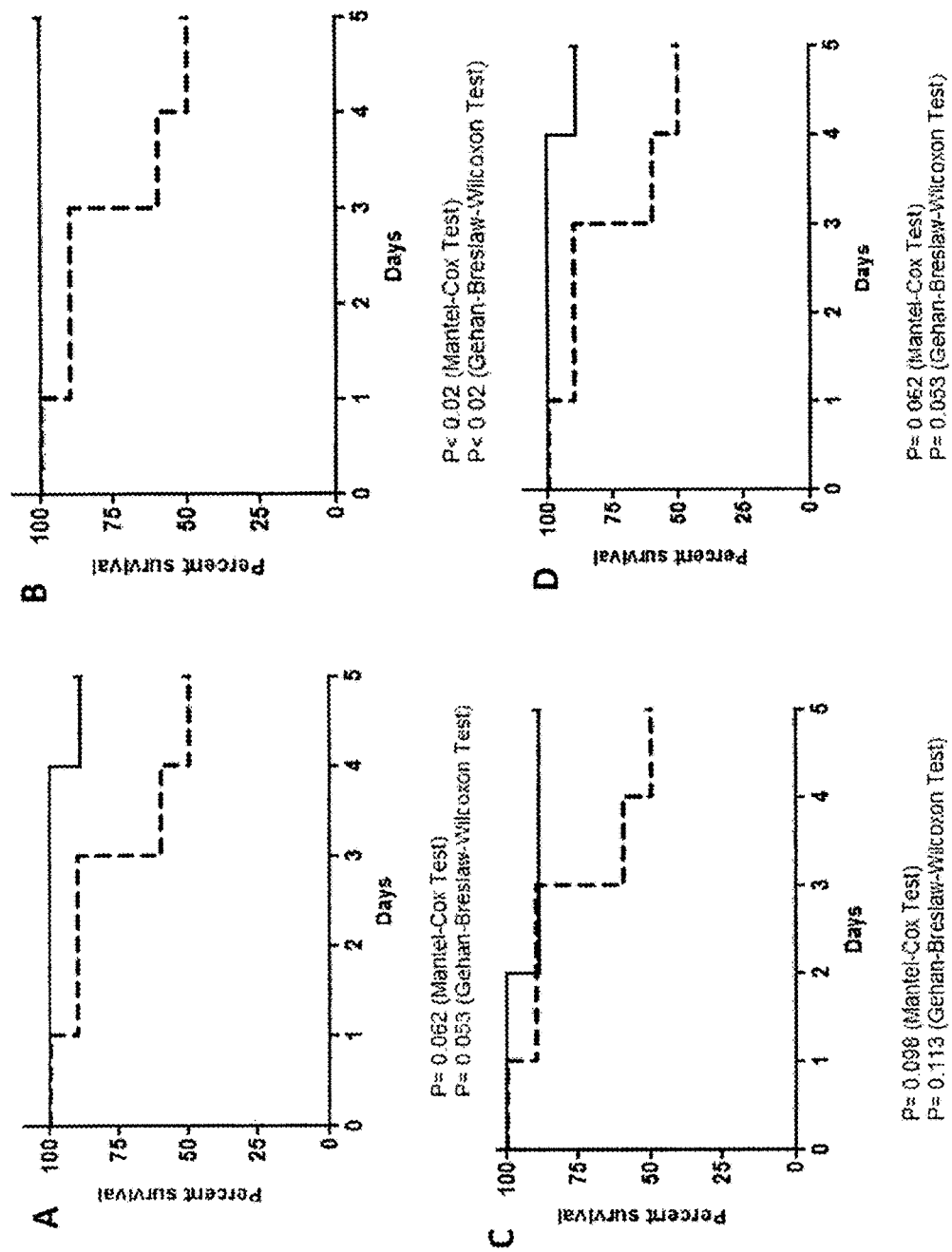
Figure 12: Active Immunization Experiment

SEQUENCE LISTING

<160> NUMBER OF SEQ ID NOS: 36

<210> SEQ ID NO 1
<211> LENGTH: 1254
<212> TYPE: DNA
<213> ORGANISM: Acinetobacter baumannii

<400> SEQUENCE: 1

```
atgaaaacgc ataaatcttt gatggtttcc tgtttatccg ttttatcaat tactcttttt      60
gttcagcatg cacaagctgc tgctgcattt gacccaaatg gttcttggat gttgggtgat     120
tggaacgggc aacgtacagc gttgcaagca caaggttatg attttttcttt tggatatacc    180 ggtgaatatg ccggtatttt agattccaaa caaacatcta cacacggtag tgcttataca     240
gggcaacttg ctttaggttc tcatttggac ctaggtaaaa ttttagggtg gcaagataca     300
gaagctcaaa tcacattaac ttatcgtgat gggcaatcgc tttctgaaca ttctccagca     360
ttggctgggc accaaagttc tgttcaagaa gtgtggggcc gtgaacaaac ttggcgttta     420
acagatttat ggatcaagaa aaaattcctt gatcagaagt tagatgttaa agtgggccgt     480
tttggtgagg gtgaagactt taatagtttt gactgtgatt tccagaactt ggcactttgt     540
ggttcacaag tgggtaactg ggtaggcgat cagtggtata actggccagt tagccaatgg     600
gcaatgcgtg tcaaatataa cttgcaacct gatttatata cacaagtggg tgtatatgaa     660
tataaccctg aaaacttgga acgtggcaaa ggcttcaacc taagtacaga tggttctcac     720
ggtgcaatta ttccagcaga agtagtttgg tcacctaaac taggtgtgca aagcatgcct     780
ggtgaatacc gtttaggtta ttactatagt actgccgatg ccaaagaaat tgcagattca     840
actaaaacat ctcataagca aggtgtttgg gtaactgcaa aacagaaatt attccagcca     900
gctgatcaaa ctgaccgtgg tttaacaggg tttgtgaacc tgactttcca cgactcagat     960
```

```
accaacaaag ttgataacat gcaaaatata ggcttagtct ataaaggttt gctgaatcaa   1020
cgtcctcaag atgagttggc acttggtgtt gctcgtatcc atatcaatga tgattggagc   1080
gatgttcaag ccaaagaata cgacaccgaa tataataccg agctttacta tggtattcat   1140
gccactaact ggctaactat tcgtccaaat gtgcaatatg ttcgtcatgt tggtgcatta   1200
aaaaatggtg ataacacttg ggtaggcggt attaagttct caactgcatt ctaa         1254
```

<210> SEQ ID NO 2
<211> LENGTH: 417
<212> TYPE: PRT
<213> ORGANISM: Acinetobacter baumannii

<400> SEQUENCE: 2

```
Met Lys Thr His Lys Ser Leu Met Val Ser Cys Leu Ser Val Leu Ser
1               5                   10                  15

Ile Thr Leu Phe Val Gln His Ala Gln Ala Ala Ala Phe Asp Pro
            20                  25                  30

Asn Gly Ser Trp Met Leu Gly Asp Trp Asn Gly Gln Arg Thr Ala Leu
        35                  40                  45

Gln Ala Gln Gly Tyr Asp Phe Ser Phe Gly Tyr Thr Gly Glu Tyr Ala
    50                  55                  60

Gly Ile Leu Asp Ser Lys Gln Thr Ser Thr His Gly Ser Ala Tyr Thr
65                  70                  75                  80

Gly Gln Leu Ala Leu Gly Ser His Leu Asp Leu Gly Lys Ile Leu Gly
                85                  90                  95

Trp Gln Asp Thr Glu Ala Gln Ile Thr Leu Thr Tyr Arg Asp Gly Gln
            100                 105                 110

Ser Leu Ser Glu His Ser Pro Ala Leu Ala Gly His Gln Ser Ser Val
        115                 120                 125

Gln Glu Val Trp Gly Arg Glu Gln Thr Trp Arg Leu Thr Asp Leu Trp
    130                 135                 140

Ile Lys Lys Lys Phe Leu Asp Gln Lys Leu Asp Val Lys Val Gly Arg
145                 150                 155                 160

Phe Gly Glu Gly Glu Asp Phe Asn Ser Phe Asp Cys Asp Phe Gln Asn
                165                 170                 175

Leu Ala Leu Cys Gly Ser Gln Val Gly Asn Trp Val Gly Asp Gln Trp
            180                 185                 190

Tyr Asn Trp Pro Val Ser Gln Trp Ala Met Arg Val Lys Tyr Asn Leu
        195                 200                 205

Gln Pro Asp Leu Tyr Thr Gln Val Gly Val Tyr Glu Tyr Asn Pro Glu
    210                 215                 220

Asn Leu Glu Arg Gly Lys Gly Phe Asn Leu Ser Thr Asp Gly Ser His
225                 230                 235                 240

Gly Ala Ile Ile Pro Ala Glu Val Val Trp Ser Pro Lys Leu Gly Val
                245                 250                 255

Gln Ser Met Pro Gly Glu Tyr Arg Leu Gly Tyr Tyr Ser Thr Ala
            260                 265                 270

Asp Ala Lys Glu Ile Ala Asp Ser Thr Lys Thr Ser His Lys Gln Gly
        275                 280                 285

Val Trp Val Thr Ala Lys Gln Lys Leu Phe Gln Pro Ala Asp Gln Thr
    290                 295                 300

Asp Arg Gly Leu Thr Gly Phe Val Asn Leu Thr Phe His Asp Ser Asp
305                 310                 315                 320

Thr Asn Lys Val Asp Asn Met Gln Asn Ile Gly Leu Val Tyr Lys Gly
```

|     |     |     | 325 |     |     |     | 330 |     |     |     | 335 |     |
| --- | --- | --- | --- | --- | --- | --- | --- | --- | --- | --- | --- | --- |
| Leu | Leu | Asn | Gln | Arg | Pro | Gln | Asp | Glu | Leu | Ala | Leu | Gly | Val | Ala | Arg |
|     |     |     | 340 |     |     |     | 345 |     |     |     | 350 |     |

Ile His Ile Asn Asp Asp Trp Ser Asp Val Gln Ala Lys Glu Tyr Asp
              355                      360                     365

Thr Glu Tyr Asn Thr Glu Leu Tyr Tyr Gly Ile His Ala Thr Asn Trp
  370                          375                         380

Leu Thr Ile Arg Pro Asn Val Gln Tyr Val Arg His Val Gly Ala Leu
385                         390                         395                     400

Lys Asn Gly Asp Asn Thr Trp Val Gly Gly Ile Lys Phe Ser Thr Ala
              405                      410                       415

Phe

<210> SEQ ID NO 3
<211> LENGTH: 1308
<212> TYPE: DNA
<213> ORGANISM: Acinetobacter baumannii

<400> SEQUENCE: 3

```
ttgatggatc tattccttaa tcgtaaatcg tttgttgtta aaagtttagc tattacagta      60
acagctttaa tgatgagtgg ggcaaatgcg gcaacttctg ataaagagga aattcgaaaa     120
cttcgtcaag aagttgaagc attaaaagca ttagttcaag aacaacgtca agtacagcaa     180
caacagcaac aagtacagca gcaacagcaa gtacagttag ctgaagtaaa agcacaacct     240
caacctgtgg cagcaccagt gtctccatta gcaggattta atctaaagc tggcgctgat      300
gtgaaccttt atggttttgt tcgtggcgat gctaactata ttattgaagg tgcagataac     360
gactttggtg atgtaagtaa gtcagacggt aaaacacatg ataaattacg tgcgactgct     420
aaaacaacac gcctcggttt agattttaat acacctgttg agacgacaa agttggtggt      480
aaaatcgaag tcgattttgc tggttcaacc acagattcaa atggctcatt gcgtattcgc     540
catgcttatt aacctataa caactggttg tttggtcaaa cgacttcaaa cttcttatct      600
aaccatgcac cagaaatgat cgacttctcg acaaacattg gtggtggtac taaacgtgta     660
cctcaagtac gctataacta caaactaggt ccaactacac aattatttgt ttctgctgaa     720
aaaggtgata gtactacttc ggtaacaggt gatagtatta gtatagcct accagcatta      780
actgctaaaa tcactcaagg ctatgcagaa ggcagaggtt ctgcttcagc tcgtgttctt     840
gtagaaaatt ataaatcaca acttgctgat gatgataaaa ctggttgggg cgttgcagtt     900
ggtactgact ttaaagtgtc tgatcctta  aaactctttg ctgacgcatc atatgttgtg     960
ggtgataata gttacttgta tggtagtaac tctccatacg cagtagatgg gaattctatt    1020
gagcaaaatg aatttgtagc agtacaagtg gtggaacttg taagattttt acctaactta    1080
cgttctactt tagcgtatgg tgctcagttc tctgatgatg cactgattga tgcgagatta    1140
aatgcctctg caaatgaaaa agttcaacaa gcatggatca actttatcta tacgccagtt    1200
aaaccaattg acttaggcgt tgagtatgta aacggtaagc gtgatacatt tgaaggtaag    1260
tcttacaaag ataaccgtgt tggtttaatg gctaaatata gtttctaa                1308
```

<210> SEQ ID NO 4
<211> LENGTH: 435
<212> TYPE: PRT
<213> ORGANISM: Acinetobacter baumannii

<400> SEQUENCE: 4

```
Met Met Asp Leu Phe Leu Asn Arg Lys Ser Phe Val Lys Ser Leu
1               5                   10                  15

Ala Ile Thr Val Thr Ala Leu Met Met Ser Gly Ala Asn Ala Ala Thr
            20                  25                  30

Ser Asp Lys Glu Glu Ile Arg Lys Leu Arg Gln Glu Val Glu Ala Leu
            35                  40                  45

Lys Ala Leu Val Gln Glu Gln Arg Gln Val Gln Gln Gln Gln Gln Gln
50                  55                  60

Val Gln Gln Gln Gln Val Gln Leu Ala Glu Val Lys Ala Gln Pro
65                  70                  75                  80

Gln Pro Val Ala Ala Pro Val Ser Pro Leu Ala Gly Phe Lys Ser Lys
                85                  90                  95

Ala Gly Ala Asp Val Asn Leu Tyr Gly Phe Val Arg Gly Asp Ala Asn
                100                 105                 110

Tyr Ile Ile Glu Gly Ala Asp Asn Asp Phe Gly Asp Val Ser Lys Ser
            115                 120                 125

Asp Gly Lys Thr His Asp Lys Leu Arg Ala Thr Ala Lys Thr Thr Arg
    130                 135                 140

Leu Gly Leu Asp Phe Asn Thr Pro Val Gly Asp Asp Lys Val Gly Gly
145                 150                 155                 160

Lys Ile Glu Val Asp Phe Ala Gly Ser Thr Thr Asp Ser Asn Gly Ser
                165                 170                 175

Leu Arg Ile Arg His Ala Tyr Leu Thr Tyr Asn Asn Trp Leu Phe Gly
            180                 185                 190

Gln Thr Thr Ser Asn Phe Leu Ser Asn His Ala Pro Glu Met Ile Asp
            195                 200                 205

Phe Ser Thr Asn Ile Gly Gly Gly Thr Lys Arg Val Pro Gln Val Arg
    210                 215                 220

Tyr Asn Tyr Lys Leu Gly Pro Thr Thr Gln Leu Phe Val Ser Ala Glu
225                 230                 235                 240

Lys Gly Asp Ser Thr Thr Ser Val Thr Gly Asp Ser Ile Lys Tyr Ser
                245                 250                 255

Leu Pro Ala Leu Thr Ala Lys Ile Thr Gln Gly Tyr Ala Glu Gly Arg
                260                 265                 270

Gly Ser Ala Ser Ala Arg Val Leu Val Glu Asn Tyr Lys Ser Gln Leu
            275                 280                 285

Ala Asp Asp Lys Thr Gly Trp Gly Val Ala Val Gly Thr Asp Phe
            290                 295                 300

Lys Val Ser Asp Pro Leu Lys Leu Phe Ala Asp Ala Ser Tyr Val Val
305                 310                 315                 320

Gly Asp Asn Ser Tyr Leu Tyr Gly Ser Asn Ser Pro Tyr Ala Val Asp
                325                 330                 335

Gly Asn Ser Ile Glu Gln Asn Glu Phe Val Ala Val Gln Val Gly Gly
            340                 345                 350

Thr Tyr Lys Ile Leu Pro Asn Leu Arg Ser Thr Leu Ala Tyr Gly Ala
            355                 360                 365

Gln Phe Ser Asp Asp Gly Thr Asp Tyr Ala Arg Leu Asn Ala Ser Ala
    370                 375                 380

Asn Glu Lys Val Gln Gln Ala Trp Ile Asn Phe Ile Tyr Thr Pro Val
385                 390                 395                 400

Lys Pro Ile Asp Leu Gly Val Glu Tyr Val Asn Gly Lys Arg Asp Thr
                405                 410                 415

Phe Glu Gly Lys Ser Tyr Lys Asp Asn Arg Val Gly Leu Met Ala Lys
```

```
                    420           425           430
Tyr Ser Phe
        435

<210> SEQ ID NO 5
<211> LENGTH: 1443
<212> TYPE: DNA
<213> ORGANISM: Acinetobacter baumannii

<400> SEQUENCE: 5 atgttttttaa gaaaaacact ttcgattgca ttattagcaa ctgcttcatc ggctgttttt      60
gcacaaggtt tagtgcttaa taatgatgat ttacgtaccg acttaaactg gttgaatcaa     120
caaggtgtta ttaacatcag cacttctact tggccattaa gtggtgatga aattcaaaga     180
gctctctctc aagctaaagt gactcatcca gcacagcaaa aagttattaa ttcagttctc     240
aatgcattaa aggcagataa cgatacagtt aaagtgggtg cttttgctga aactgatatc     300
aaaaatattc ctcaagcatt tggtgataac caaaaatcgc agtaccaagg ttcattagag     360
tttaatgctg gtggtgaaaa ttgggatgca aaaatccgtg taaacgcaga aaaagaccct     420
caaattgata gtgggcatga cgttaacgtt gagggttcat atgtcgctgg taaactctgg     480
aaccagtggc ttgttgcagg tcaaattcca acatggtggg gacctggaca tgatggtagc     540
ttaatccgag cgatgcaag tcgtcctgtg tatggcgtga cggcacaaag agctgtacaa     600
aatgcttttg agacaaaatg gttatcttgg attggaccct tggcaatatca agcttttgca     660 ggccaattag atgattataa agctgttcct catgcgaaat tattaggctt acgttttaact    720 gcaagacctt taccctattt agaactaggt gcttctcgta ctttacaatg gggtggtgaa     780
ggacgttctg aaagtgggga ttcttttgtgg aatgcaatta aagggaatga caatgtgtat    840
gattctgatg aagatcgttc taaccaaatt gcaggttttg atgctcgttt aaatctacaa     900
tctcttataa atgctcctgt tggtatttat ggtcaatatg ttggtgaaga tgaagctgga     960
ctacttcctt ctaaaaaaat gtatttagca ggagtcgact attcttctag ctataataat    1020
atgccatatc aactttatgc agaatgggct gatacccgca ctaataatga tgtgaagggt    1080
atttcctata tcattatgt ttataaagat ggttattatc aacatggctt cccattagga    1140
catgcgatgg gtggcgatgg acaaatgtat tctgtgggtg gtgatatccg ctttgacgtg    1200
atgaaccgtt taagcggtcg tgctatggtg gttaaagtta accaatctaa cttggcaatt    1260
aataaagcat tccctaaaga tgatgaaatt aaagcgcttg atctaacttg gacacattac    1320
atcaaacctg atcttccatt aaaaattaat ggttgggtaa gtgattctga cttagaaggt    1380
aatgatgcgg gtgcatcaat tggagtggaa attcctctag agcgtaaaat gtttggtttc    1440
taa                                                                  1443

<210> SEQ ID NO 6
<211> LENGTH: 480
<212> TYPE: PRT
<213> ORGANISM: Acinetobacter baumannii

<400> SEQUENCE: 6

Met Phe Leu Arg Lys Thr Leu Ser Ile Ala Leu Leu Ala Thr Ala Ser
1               5                   10                  15

Ser Ala Val Phe Ala Gln Gly Leu Val Leu Asn Asn Asp Asp Leu Arg
            20                  25                  30

Thr Asp Leu Asn Trp Leu Asn Gln Gln Gly Val Ile Asn Ile Ser Thr
        35                  40                  45
```

```
Ser Thr Trp Pro Leu Ser Gly Asp Glu Ile Gln Arg Ala Leu Ser Gln
    50                  55                  60

Ala Lys Val Thr His Pro Ala Gln Gln Lys Val Ile Asn Ser Val Leu
65                  70                  75                  80

Asn Ala Leu Lys Ala Asp Asn Asp Thr Val Lys Val Gly Ala Phe Ala
                    85                  90                  95

Glu Thr Asp Ile Lys Asn Ile Pro Gln Ala Phe Gly Asp Asn Gln Lys
                100                 105                 110

Ser Gln Tyr Gln Gly Ser Leu Glu Phe Asn Ala Gly Gly Glu Asn Trp
            115                 120                 125

Asp Ala Lys Ile Arg Val Asn Ala Glu Lys Asp Pro Gln Ile Asp Ser
        130                 135                 140

Gly His Asp Val Asn Val Glu Gly Ser Tyr Val Ala Gly Lys Leu Trp
145                 150                 155                 160

Asn Gln Trp Leu Val Ala Gly Gln Ile Pro Thr Trp Gly Pro Gly
                    165                 170                 175

His Asp Gly Ser Leu Ile Arg Gly Asp Ala Ser Arg Pro Val Tyr Gly
                180                 185                 190

Val Thr Ala Gln Arg Ala Val Gln Asn Ala Phe Glu Thr Lys Trp Leu
            195                 200                 205

Ser Trp Ile Gly Pro Trp Gln Tyr Gln Ala Phe Ala Gly Gln Leu Asp
        210                 215                 220

Asp Tyr Lys Ala Val Pro His Ala Lys Leu Leu Gly Leu Arg Leu Thr
225                 230                 235                 240

Ala Arg Pro Leu Pro Tyr Leu Glu Leu Gly Ala Ser Arg Thr Leu Gln
                    245                 250                 255

Trp Gly Gly Glu Gly Arg Ser Glu Ser Trp Asp Ser Leu Trp Asn Ala
                260                 265                 270

Ile Lys Gly Asn Asp Asn Val Tyr Asp Ser Asp Glu Asp Arg Ser Asn
            275                 280                 285

Gln Ile Ala Gly Phe Asp Ala Arg Leu Asn Leu Gln Ser Leu Ile Asn
        290                 295                 300

Ala Pro Val Gly Ile Tyr Gly Gln Tyr Val Gly Glu Asp Glu Ala Gly
305                 310                 315                 320

Leu Leu Pro Ser Lys Lys Met Tyr Leu Ala Gly Val Asp Tyr Ser Ser
                    325                 330                 335

Ser Tyr Asn Asn Met Pro Tyr Gln Leu Tyr Ala Glu Trp Ala Asp Thr
                340                 345                 350

Arg Thr Asn Asn Asp Val Lys Gly Ile Ser Tyr Asn His Tyr Val Tyr
            355                 360                 365

Lys Asp Gly Tyr Tyr Gln His Gly Phe Pro Leu Gly His Ala Met Gly
        370                 375                 380

Gly Asp Gly Gln Met Tyr Ser Val Gly Gly Asp Ile Arg Phe Asp Val
385                 390                 395                 400

Met Asn Arg Leu Ser Gly Arg Ala Met Val Lys Val Asn Gln Ser
                    405                 410                 415

Asn Leu Ala Ile Asn Lys Ala Phe Pro Lys Asp Asp Glu Ile Lys Ala
                420                 425                 430

Leu Asp Leu Thr Trp Thr His Tyr Ile Lys Pro Asp Leu Pro Leu Lys
            435                 440                 445

Ile Asn Gly Trp Val Ser Asp Ser Asp Leu Glu Gly Asn Asp Ala Gly
        450                 455                 460
```

Ala Ser Ile Gly Val Glu Ile Pro Leu Glu Arg Lys Met Phe Gly Phe
465                 470                 475                 480

<210> SEQ ID NO 7
<211> LENGTH: 2721
<212> TYPE: DNA
<213> ORGANISM: Acinetobacter baumannii

<400> SEQUENCE: 7

| | | | | | |
|---|---|---|---|---|---|
| atgccttcta | aaattaagtt | taaacagtca | actctttctc | actctatgca | tttaatctta | 60 |
| aaaatgcaga | gtatacctaa | acttatttgt | agcagcttat | tattaagttt | atgtgttact | 120 |
| ccttgttatg | ctcaaagttc | ggctgagacc | gttacaccag | aagcaaatca | gtcggtaaca | 180 |
| gattcattgg | tacaacaaac | taatacaaat | aacccaagtg | atgttccaat | taccgatgtc | 240 |
| gctactcttg | taactcaagc | acagcaacaa | caagatagct | tggctatatt | gcaacaacaa | 300 |
| gaacaatttc | cgaatcagat | tgaagaattt | aagccaatta | cgcttgataa | tcttgaagac | 360 |
| ttaccggtta | tgcctgttga | tcagaatatg | gcaaatgaaa | tttatcgggt | agcagaagag | 420 |
| gcaaaaaacg | aggctcaaaa | cttccagaat | ggtacgcaaa | acaaccaga | aatggtggtg | 480 |
| aatgacgcat | cacaagcaga | attacatgaa | attaatcagg | ccctgtaaa | tattgaccag | 540 |
| ctcatgcatg | agattcaatc | tgatagtaag | attgtggttg | aagccaatga | aacaggaaaa | 600 |
| actttacctg | agcttactgc | tgccgttgaa | gagccacccg | aagaaaaagg | tttctttaga | 660 |
| cgtatattca | ataaaatccg | tccacctcgg | gtaattccaa | tggagcagat | accccgtatt | 720 |
| actgctgagg | ttacgggtgc | gccagatgat | ttagctaaaa | atatcaaagg | taaattatct | 780 |
| acatttaccc | aagaatcatt | tgaagatttt | aatgcagcgc | taccgcaact | taggagctta | 840 |
| agtaatcagg | ctgctcaagc | tgtaggttat | acaatgctg | agtttcgttt | tgaaaagtta | 900 |
| agtgccagtc | gcgtacgcgt | taatgtaacg | ccaaatgaac | cagtacggat | taatgaacaa | 960 |
| aacattgaat | ttactggtgc | tggtgcaaaa | cagccacaat | ttcaggtcat | tcgtttagtt | 1020 |
| cctgaccaag | atgtaggtga | tatttttaat | catggccttt | acgaaaccac | aaaaagccga | 1080 |
| attgtcgatg | ctgcatcgga | taatggttat | tttgatgcgt | attggcgttt | acatgacgta | 1140 |
| aaagtgagcc | aacctgaaaa | taaagcggat | attaacctca | gtatgagac | tggtgagcgt | 1200 |
| tataagcttg | gtaaggttga | gtttcgcatg | agcgatccat | caaaaccatt | acctttaaat | 1260 |
| atgaatattc | ttgaaagcat | ggcaccgtgg | aaagagggtg | atgactatgc | ttttggcgt | 1320 |
| gtaaatgttt | tagcaaataa | cctgactaac | tcacgttatt | ttaactatac | cttggtcgat | 1380 |
| tcaattaaac | ccgacccaat | tgaaaaacca | cttgagttac | cacccgattt | acaagcgttg | 1440 |
| gtcgatcagc | agaatgttga | tattgacgaa | tcgaagctgc | ttcctttaga | gcaacaacaa | 1500 |
| cttgccaaag | cacgccagtt | ggcttcctca | agtaaagaag | taacacaaaa | tgtggtagat | 1560 |
| gaaaaacaat | tgccggaac | tgaaagtgta | caagccgccc | ctgcatcttt | aaaagctgca | 1620 |
| actgtacaac | atgaagaaca | agagtctgaa | caagaccgtt | acaggctca | agctcgggaa | 1680 |
| gaaaaacgta | ccagtgat | tgtgacgtta | aatgccgata | aactaaatag | tctggaaaca | 1740 |
| ggtattggtt | atggtaccga | cactggcgcc | cgtttacgta | gccaatatag | acgttcgatt | 1800 |
| gtgaataaat | acggtcattc | atttgacgca | aacttggagc | tttcccaaat | tcgtcaatct | 1860 |
| atagatgggc | gctatagtat | tccttataaa | catccgttaa | atgattactt | taatattgtg | 1920 |
| ggtggttacg | agcgtgagac | gagggatgat | attggtccgg | atgtaagttt | acttacagaa | 1980 |
| tcggcagttt | taggggtga | gcgagttatt | aaaaaaccgc | tcggaaactg | gcaacatact | 2040 |

-continued

```
attggggtac gttatcgtct cgaccgccta actcaaaagg ggaatgtgga tatctctgag    2100
ctaccagatg catttaaaac tgctgcatca gagcaagaag cattattatt tagttatgag    2160
acctctaaaa cttcaagtaa tacacgctta aacccgacca aagcttttaa acaaacttat    2220
aaattagaat taggtagtga aagtttactt tcagatgcca atatggcgat tgcaactgcg    2280
ggttggagat ttatttattc tttaggtgaa atgatgacc atcagtttgt tgggcggtcc     2340
gattttagtt atattttac cgatgagttt gataaagttc catacaattt aagattcttt     2400
actggtggtg accagacaat tcgtggtttt gattataaaa gtctttcacc agaagataat    2460
ggatataaga ttggtggaca ggctctagca gtaggctctt tagaatataa ctatcaattc    2520
aaagagggtt ggcgagcagc tgttttttct gatttttggta atgcttacga taagagtttt   2580
agtaatccga cggcctatag tgtgggtgtt ggtattcgtt ggaagtcccc aattggacca    2640
attcgtttag acgtggcttc tggtatttct gatgataacc atccgattcg tttgcatttc    2700
tttattggtc cacaactttta a                                             2721
```

<210> SEQ ID NO 8
<211> LENGTH: 906
<212> TYPE: PRT
<213> ORGANISM: Acinetobacter baumannii

<400> SEQUENCE: 8

```
Met Pro Ser Lys Ile Lys Phe Lys Gln Ser Thr Leu Ser His Ser Met
1               5                   10                  15

His Leu Ile Leu Lys Met Gln Ser Ile Pro Lys Leu Ile Cys Ser Ser
            20                  25                  30

Leu Leu Leu Ser Leu Cys Val Thr Pro Cys Tyr Ala Gln Ser Ser Ala
        35                  40                  45

Glu Thr Val Thr Pro Glu Ala Asn Gln Ser Val Thr Asp Ser Leu Val
    50                  55                  60

Gln Gln Thr Asn Thr Asn Asn Pro Ser Asp Val Pro Ile Thr Asp Val
65                  70                  75                  80

Ala Thr Leu Val Thr Gln Ala Gln Gln Gln Asp Ser Leu Ala Ile
                85                  90                  95

Leu Gln Gln Gln Glu Gln Phe Pro Asn Gln Ile Glu Glu Phe Lys Pro
            100                 105                 110

Ile Thr Leu Asp Asn Leu Glu Asp Leu Pro Val Met Pro Val Asp Gln
        115                 120                 125

Asn Met Ala Asn Glu Ile Tyr Arg Val Ala Glu Glu Ala Lys Asn Glu
    130                 135                 140

Ala Gln Asn Phe Gln Asn Gly Thr Gln Lys Gln Pro Glu Met Val Val
145                 150                 155                 160

Asn Asp Ala Ser Gln Ala Glu Leu His Glu Ile Asn Gln Ala Pro Val
                165                 170                 175

Asn Ile Asp Gln Leu Met His Glu Ile Gln Ser Asp Ser Lys Ile Val
            180                 185                 190

Val Glu Ala Asn Glu Thr Gly Lys Thr Leu Pro Glu Leu Thr Ala Ala
        195                 200                 205

Val Glu Glu Pro Pro Glu Lys Gly Phe Phe Arg Arg Ile Phe Asn
    210                 215                 220

Lys Ile Arg Pro Pro Arg Val Ile Pro Met Glu Gln Ile Pro Arg Ile
225                 230                 235                 240

Thr Ala Glu Val Thr Gly Ala Pro Asp Asp Leu Ala Lys Asn Ile Lys
                245                 250                 255
```

```
Gly Lys Leu Ser Thr Phe Thr Gln Glu Ser Phe Glu Asp Phe Asn Ala
            260                 265                 270

Ala Leu Pro Gln Leu Arg Ser Leu Ser Asn Gln Ala Gln Ala Val
        275                 280                 285

Gly Tyr Tyr Asn Ala Glu Phe Arg Phe Glu Lys Leu Ser Ala Ser Arg
290                 295                 300

Val Arg Val Asn Val Thr Pro Asn Glu Pro Val Arg Ile Asn Glu Gln
305                 310                 315                 320

Asn Ile Glu Phe Thr Gly Ala Gly Ala Lys Gln Pro Gln Phe Gln Val
                325                 330                 335

Ile Arg Leu Val Pro Asp Gln Asp Val Gly Asp Ile Phe Asn His Gly
            340                 345                 350

Leu Tyr Glu Thr Thr Lys Ser Arg Ile Val Asp Ala Ala Ser Asp Asn
        355                 360                 365

Gly Tyr Phe Asp Ala Tyr Trp Arg Leu His Asp Val Lys Val Ser Gln
370                 375                 380

Pro Glu Asn Lys Ala Asp Ile Asn Leu Lys Tyr Glu Thr Gly Glu Arg
385                 390                 395                 400

Tyr Lys Leu Gly Lys Val Glu Phe Arg Met Ser Asp Pro Ser Lys Pro
                405                 410                 415

Leu Pro Leu Asn Met Asn Ile Leu Glu Ser Met Ala Pro Trp Lys Glu
            420                 425                 430

Gly Asp Asp Tyr Ala Phe Trp Arg Val Asn Val Leu Ala Asn Asn Leu
        435                 440                 445

Thr Asn Ser Arg Tyr Phe Asn Tyr Thr Leu Val Asp Ser Ile Lys Pro
        450                 455                 460

Asp Pro Ile Glu Lys Pro Leu Glu Leu Pro Pro Asp Leu Gln Ala Leu
465                 470                 475                 480

Val Asp Gln Gln Asn Val Asp Ile Asp Glu Ser Lys Leu Leu Pro Leu
                485                 490                 495

Glu Gln Gln Gln Leu Ala Lys Ala Arg Gln Leu Ala Ser Ser Ser Lys
            500                 505                 510

Glu Val Thr Gln Asn Val Val Asp Glu Lys Gln Phe Ala Gly Thr Glu
        515                 520                 525

Ser Val Gln Ala Ala Pro Ala Ser Leu Lys Ala Thr Val Gln His
530                 535                 540

Glu Glu Gln Glu Ser Glu Gln Asp Arg Leu Gln Ala Gln Ala Arg Glu
545                 550                 555                 560

Glu Lys Arg Ile Pro Val Ile Val Thr Leu Asn Ala Asp Lys Leu Asn
                565                 570                 575

Ser Leu Glu Thr Gly Ile Gly Tyr Gly Thr Asp Thr Gly Ala Arg Leu
            580                 585                 590

Arg Ser Gln Tyr Arg Arg Ser Ile Val Asn Lys Tyr Gly His Ser Phe
        595                 600                 605

Asp Ala Asn Leu Glu Leu Ser Gln Ile Arg Gln Ser Ile Asp Gly Arg
        610                 615                 620

Tyr Ser Ile Pro Tyr Lys His Pro Leu Asn Asp Tyr Phe Asn Ile Val
625                 630                 635                 640

Gly Gly Tyr Glu Arg Glu Thr Arg Asp Asp Ile Gly Pro Asp Val Ser
                645                 650                 655

Leu Leu Thr Glu Ser Ala Val Leu Gly Gly Glu Arg Val Ile Lys Lys
            660                 665                 670
```

```
Pro Leu Gly Asn Trp Gln His Thr Ile Gly Val Arg Tyr Arg Leu Asp
            675                 680                 685

Arg Leu Thr Gln Lys Gly Asn Val Asp Ile Ser Glu Leu Pro Asp Ala
        690                 695                 700

Phe Lys Thr Ala Ala Ser Glu Gln Ala Leu Leu Phe Ser Tyr Glu
705                 710                 715                 720

Thr Ser Lys Thr Ser Ser Asn Thr Arg Leu Asn Pro Thr Lys Ala Phe
                725                 730                 735

Lys Gln Thr Tyr Lys Leu Glu Leu Gly Ser Glu Ser Leu Leu Ser Asp
                740                 745                 750

Ala Asn Met Ala Ile Ala Thr Ala Gly Trp Arg Phe Ile Tyr Ser Leu
                755                 760                 765

Gly Glu Asn Asp Asp His Gln Phe Val Gly Arg Ser Asp Phe Ser Tyr
            770                 775                 780

Ile Phe Thr Asp Glu Phe Asp Lys Val Pro Tyr Asn Leu Arg Phe Phe
785                 790                 795                 800

Thr Gly Gly Asp Gln Thr Ile Arg Gly Phe Asp Tyr Lys Ser Leu Ser
                805                 810                 815

Pro Glu Asp Asn Gly Tyr Lys Ile Gly Gly Gln Ala Leu Ala Val Gly
            820                 825                 830

Ser Leu Glu Tyr Asn Tyr Gln Phe Lys Glu Gly Trp Arg Ala Ala Val
            835                 840                 845

Phe Ser Asp Phe Gly Asn Ala Tyr Asp Lys Ser Phe Ser Asn Pro Thr
        850                 855                 860

Ala Tyr Ser Val Gly Val Gly Ile Arg Trp Lys Ser Pro Ile Gly Pro
865                 870                 875                 880

Ile Arg Leu Asp Val Ala Ser Gly Ile Ser Asp Asp Asn His Pro Ile
                885                 890                 895

Arg Leu His Phe Phe Ile Gly Pro Gln Leu
            900                 905

<210> SEQ ID NO 9
<211> LENGTH: 1500
<212> TYPE: DNA
<213> ORGANISM: Acinetobacter baumannii

<400> SEQUENCE: 9
ttgttatata aaatgccaac acatcaatat cgacagtcta aacgtccttt tttgtttaaa      60
cccaattacc ttgcgttggt attgggagta ttaattgcaa cgcctattta tgcgcaaagt     120
ttaagttatg ctgaagcaga acaacaggct ttaaaaagct catacagcac tcaagccaac     180
caagcattac aacaagcctc tcagttagaa gccgaagcgg taaaaggttt aggactcccc     240
agagttgatt taaatgtgag agcatatgct tttcatagtg aaacagatgt acccttaggc     300
tcttttaaac aaaaacttga aaatgattta agccaaggac tcaatgataa attatcccag     360
tggaacaatg tcattccatc agatgtttta ggtcaagttc aagaaggctc aaaccaaatc     420
atacatgacg gtataaaccg ttttcctgac tacgctaatt tgactgtaga agaccaagta     480
gtccgaccat ctatttcagt ggtgatgccg ctctacacag ggggcttaac aactagtgcc     540
aaaaaaatag ccaacattca ggctcaacgc tccgagcttt caagccaaca caacaagat     600 atccagcgct tcgaagtcgt acaaagttat tttaatgtgc aattacaaca caactggtc     660 gcaagtagtc tatttaactt taatgcaatg caaaaacatt acagcaatgc gttaaagctc     720
gaacagcaag gttttattag taaagggcaa cgtatgcagt ttgaagttgc tcgtaacaat     780
```

```
gccgaacgaa ctctacaaaa tgcgcaggca aatctgaatg ctagccaatt taatttaaac    840
aatcttttgc accagcaaaa taatgctgat ttaagtactc ctcttttttgt aaatactgtt    900 cgtagccaat cgttagaatc tcttttaagc agttactctc aaaaatctag ccttgtgcaa    960
aaaatgcagt tagacactca attggcaaat gcaaatattc aggctcaaca agcagcaaaa    1020
aaaccgagtc ttttcgcttt tggtgagtat tcactcgatg aaaatgaaaa ctggattgta    1080
ggtgttatgg caaaatacaa tctgtttttct ggcgtagata aaaataagaa tattcatgct    1140
gccgagttaa aacgttatgc ttcagaactc atgactgaac gaactaaaca agagattgaa    1200
gcattattga ataagtctta taacgagctc aattcagcac agcaaagtca tacgctattg    1260
caaaggaata tcagcgcagc tcaagaaaac ctacgtattc aggaactttc tttccgagaa    1320
ggcatgggta cagcgactca agtgatcgat gcacaaaatg cattaagtgc tttaaaaaca    1380
gaaatggctt taaatgctta taaatatgtc atgtcgctcg caacgctatt acaaagccat    1440
ggttctatgg accagtttaa agcttatgtg actcaaccac acactgacta tatccgctaa    1500
```

<210> SEQ ID NO 10
<211> LENGTH: 499
<212> TYPE: PRT
<213> ORGANISM: Acinetobacter baumannii

<400> SEQUENCE: 10

```
Met Leu Tyr Lys Met Pro Thr His Gln Tyr Arg Gln Ser Lys Arg Pro
1               5                   10                  15

Phe Leu Phe Lys Pro Asn Tyr Leu Ala Leu Val Leu Gly Val Leu Ile
            20                  25                  30

Ala Thr Pro Ile Tyr Ala Gln Ser Leu Ser Tyr Ala Glu Ala Glu Gln
        35                  40                  45

Gln Ala Leu Lys Ser Ser Tyr Ser Thr Gln Ala Asn Gln Ala Leu Gln
    50                  55                  60

Gln Ala Ser Gln Leu Glu Ala Glu Ala Val Lys Gly Leu Gly Leu Pro
65                  70                  75                  80

Arg Val Asp Leu Asn Val Arg Ala Tyr Ala Phe His Ser Glu Thr Asp
                85                  90                  95

Val Pro Leu Gly Ser Phe Lys Gln Lys Leu Glu Asn Asp Leu Ser Gln
            100                 105                 110

Gly Leu Asn Asp Lys Leu Ser Gln Trp Asn Asn Val Ile Pro Ser Asp
        115                 120                 125

Val Leu Gly Gln Val Gln Glu Gly Ser Asn Gln Ile Ile His Asp Gly
    130                 135                 140

Ile Asn Arg Phe Pro Asp Tyr Ala Asn Leu Thr Val Glu Asp Gln Val
145                 150                 155                 160

Val Arg Pro Ser Ile Ser Val Val Met Pro Leu Tyr Thr Gly Gly Leu
                165                 170                 175

Thr Thr Ser Ala Lys Lys Ile Ala Asn Ile Gln Ala Gln Arg Ser Glu
            180                 185                 190

Leu Ser Ser Gln Gln Gln Gln Asp Ile Gln Arg Phe Glu Val Val Gln
        195                 200                 205

Ser Tyr Phe Asn Val Gln Leu Gln Gln Leu Val Ala Ser Ser Leu
    210                 215                 220

Phe Asn Phe Asn Ala Met Gln Lys His Tyr Ser Asn Ala Leu Lys Leu
225                 230                 235                 240

Glu Gln Gln Gly Phe Ile Ser Lys Gly Gln Arg Met Gln Phe Glu Val
                245                 250                 255
```

Ala Arg Asn Asn Ala Glu Arg Thr Leu Gln Asn Ala Gln Ala Asn Leu
                260                 265                 270

Asn Ala Ser Gln Phe Asn Leu Asn Leu Leu His Gln Gln Asn Asn
        275                 280                 285

Ala Asp Leu Ser Thr Pro Leu Phe Val Asn Thr Val Arg Ser Gln Ser
290                 295                 300

Leu Glu Ser Leu Leu Ser Ser Tyr Ser Gln Lys Ser Ser Leu Val Gln
305                 310                 315                 320

Lys Met Gln Leu Asp Thr Gln Leu Ala Asn Ala Asn Ile Gln Ala Gln
                325                 330                 335

Gln Ala Ala Lys Lys Pro Ser Leu Phe Ala Phe Gly Glu Tyr Ser Leu
            340                 345                 350

Asp Glu Asn Glu Asn Trp Ile Val Gly Val Met Ala Lys Tyr Asn Leu
        355                 360                 365

Phe Ser Gly Val Asp Lys Asn Lys Asn Ile His Ala Ala Glu Leu Lys
370                 375                 380

Arg Tyr Ala Ser Glu Leu Met Thr Glu Arg Thr Lys Gln Glu Ile Glu
385                 390                 395                 400

Ala Leu Leu Asn Lys Ser Tyr Asn Glu Leu Asn Ser Ala Gln Gln Ser
                405                 410                 415

His Thr Leu Leu Gln Arg Asn Ile Ser Ala Ala Gln Glu Asn Leu Arg
            420                 425                 430

Ile Gln Glu Leu Ser Phe Arg Glu Gly Met Gly Thr Ala Thr Gln Val
        435                 440                 445

Ile Asp Ala Gln Asn Ala Leu Ser Ala Leu Lys Thr Glu Met Ala Leu
450                 455                 460

Asn Ala Tyr Lys Tyr Val Met Ser Leu Ala Thr Leu Leu Gln Ser His
465                 470                 475                 480

Gly Ser Met Asp Gln Phe Lys Ala Tyr Val Thr Gln Pro His Thr Asp
                485                 490                 495

Tyr Ile Arg

<210> SEQ ID NO 11
<211> LENGTH: 534
<212> TYPE: DNA
<213> ORGANISM: Acinetobacter baumannii

<400> SEQUENCE: 11
atgaaaaaac ttgctttgat cgctgctctt tcggttgtag ggattgcgaa tgctcaagct      60
gctgatggta caattacaat taatggttta gttacagaca aaacttgtga catcgttact     120
cctgctggta agatttcac agtgactctt cctactgttt ctaaacaaac tttagctgtt      180
gctggggatg ttgctggccg tactcctttc caaatcaact tagctaactg ttcacaaggt     240
aaagtagcta cttactttga accaggtgca actgttgact tcaatactgg tcgtttactt     300
aaccaagacg ctactggtgc taaaaacgtt aacgttcaac ttttaggtag caacaataac     360
ttcatcccag tacttgctgc tggtgcaaac ggtgctcaag ctaactctca atgggttgac     420
gtagctgaag gtgcaagtgc tgaccttaac tactatgctg aatactatgc aactggtgct     480
tctactgctg gtaaagtaac tacttctgtt caatacacaa ttatctatca ataa           534

<210> SEQ ID NO 12
<211> LENGTH: 177
<212> TYPE: PRT
<213> ORGANISM: Acinetobacter baumannii

<400> SEQUENCE: 12

Met Lys Lys Leu Ala Leu Ile Ala Ala Leu Ser Val Val Gly Ile Ala
1               5                   10                  15

Asn Ala Gln Ala Ala Asp Gly Thr Ile Thr Ile Asn Gly Leu Val Thr
            20                  25                  30

Asp Lys Thr Cys Asp Ile Val Thr Pro Ala Gly Lys Asp Phe Thr Val
        35                  40                  45

Thr Leu Pro Thr Val Ser Lys Gln Thr Leu Ala Val Ala Gly Asp Val
    50                  55                  60

Ala Gly Arg Thr Pro Phe Gln Ile Asn Leu Ala Asn Cys Ser Gln Gly
65                  70                  75                  80

Lys Val Ala Thr Tyr Phe Glu Pro Gly Ala Thr Val Asp Phe Asn Thr
                85                  90                  95

Gly Arg Leu Leu Asn Gln Asp Ala Thr Gly Ala Lys Asn Val Asn Val
            100                 105                 110

Gln Leu Leu Gly Ser Asn Asn Asn Phe Ile Pro Val Leu Ala Ala Gly
        115                 120                 125

Ala Asn Gly Ala Gln Ala Asn Ser Gln Trp Val Asp Val Ala Glu Gly
    130                 135                 140

Ala Ser Ala Asp Leu Asn Tyr Tyr Ala Glu Tyr Tyr Ala Thr Gly Ala
145                 150                 155                 160

Ser Thr Ala Gly Lys Val Thr Thr Ser Val Gln Tyr Thr Ile Ile Tyr
                165                 170                 175

Gln

<210> SEQ ID NO 13
<211> LENGTH: 543
<212> TYPE: DNA
<213> ORGANISM: Acinetobacter baumannii

<400> SEQUENCE: 13
atgaatatga aaacattca gaaatcactt cttgcagcat taatagttgc tggttatgcg      60
gtaaatactc aagcagctgt tactggtcag gttgacgtta aattaaatat ctcaacaggc    120
tgtactgtag gtggtagtca aactgaagga aatatgaaca gtttggtac tttaaatttt     180
ggtaaaactt ccggtacttg gaacaacgta ttaacagctg aagttgcttc agcagcaaca    240
ggtggcaata tttctgtgac ttgtgacgga acagatcctg ttgattttac agtcgcaatt    300
gacggtggtg aacgtacaga ccgcacttta aaaaatactg cttctgctga gtagttgca    360
tataacgttt atcgtgatgc tgcacgtaca aaccttatg ttgtaaaacca accacaacag    420
ttcactacag taagtggcca agctactgcc gtaccaattt tcggtgcaat tgctccaaac    480
acaggtacac caaaagcaca aggcgattat aaagatactc tattagtcac tgtaaatttc    540
taa                                                                   543

<210> SEQ ID NO 14
<211> LENGTH: 180
<212> TYPE: PRT
<213> ORGANISM: Acinetobacter baumannii

<400> SEQUENCE: 14

Met Asn Met Lys Asn Ile Gln Lys Ser Leu Leu Ala Ala Leu Ile Val
1               5                   10                  15

Ala Gly Tyr Ala Val Asn Thr Gln Ala Ala Val Thr Gly Gln Val Asp
            20                  25                  30

```
Val Lys Leu Asn Ile Ser Thr Gly Cys Thr Val Gly Ser Gln Thr
         35                  40                  45

Glu Gly Asn Met Asn Lys Phe Gly Thr Leu Asn Phe Gly Lys Thr Ser
 50                  55                  60

Gly Thr Trp Asn Val Leu Thr Ala Glu Val Ala Ser Ala Ala Thr
 65                  70                  75                  80

Gly Gly Asn Ile Ser Val Thr Cys Asp Gly Thr Asp Pro Val Asp Phe
                 85                  90                  95

Thr Val Ala Ile Asp Gly Gly Glu Arg Thr Asp Arg Thr Leu Lys Asn
             100                 105                 110

Thr Ala Ser Ala Asp Val Val Ala Tyr Asn Val Tyr Arg Asp Ala Ala
         115                 120                 125

Arg Thr Asn Leu Tyr Val Val Asn Gln Pro Gln Gln Phe Thr Thr Val
     130                 135                 140

Ser Gly Gln Ala Thr Ala Val Pro Ile Phe Gly Ala Ile Ala Pro Asn
145                 150                 155                 160

Thr Gly Thr Pro Lys Ala Gln Gly Asp Tyr Lys Asp Thr Leu Leu Val
                165                 170                 175

Thr Val Asn Phe
            180

<210> SEQ ID NO 15
<211> LENGTH: 1071
<212> TYPE: DNA
<213> ORGANISM: Acinetobacter baumannii

<400> SEQUENCE: 15
atgaaattga gtcgtattgc acttgctact atgcttgttg ctgctccatt agctgctgct      60
aatgctggcg taacagttac tccattattg cttggttaca cttttccaaga cagccaacac    120
aacaatggcg gtaaagatgg taacttaact aacggtcctg agttacaaga cgatttattc    180
gttggcgcag ctcttggtat cgagttaact ccatggttag gtttcgaagc tgaatataac    240
caagttaaag cgacgtaga cggcgcttct gctggtgctg aatataaaca aaaacaaatc     300
aacggtaact tctatgttac ttctgattta attactaaaa actacgacag caaaatcaag    360
ccgtacgtat tattaggtgc tggtcactat aaatacgact ttgatggcgt aaaccgtggt   420
acacgtggta cttctgaaga aggtacttta ggtaacgctg tgttggtgc tttctggcgc    480
ttaaacgacg ctttatctct tcgtactgaa gctcgtgcta cttataatgc tgatgaagag   540
ttctggaact atacagctct tgctggctta aacgtagttc ttggtggtca cttgaagcct   600
gctgctcctg tagtagaagt tgctccagtt gaaccaactc cagttgctcc acaaccacaa   660
gagttaactg aagaccttaa catggaactt cgtgtgttct tgatactaa caaatcaaac    720
atcaaagacc aatacaagcc agaaattgct aaagttgctg aaaaattatc tgaatacct    780
aacgctactg cacgtatcga aggtcacaca gataacactg gtccacgtaa gttgaacgaa   840
cgtttatctt tagctcgtgc taactctgtt aaatcagctc ttgtaaacga atacaacgtt   900
gatgcttctc gtttgtctac tcaaggtttc gcttgggatc aaccgattgc tgacaacaaa   960
actaaagaag tcgtgctat gaaccgtcgt gtattcgcga caatcactgg tagccgtact   1020
gtagtagttc aacctggtca agaagcggca gctcctgcag cagctcaata a            1071

<210> SEQ ID NO 16
<211> LENGTH: 356
<212> TYPE: PRT
```

<213> ORGANISM: Acinetobacter baumannii

<400> SEQUENCE: 16

Met Lys Leu Ser Arg Ile Ala Leu Ala Thr Met Leu Val Ala Ala Pro
1               5                   10                  15

Leu Ala Ala Ala Asn Ala Gly Val Thr Val Thr Pro Leu Leu Leu Gly
            20                  25                  30

Tyr Thr Phe Gln Asp Ser Gln His Asn Asn Gly Gly Lys Asp Gly Asn
        35                  40                  45

Leu Thr Asn Gly Pro Glu Leu Gln Asp Asp Leu Phe Val Gly Ala Ala
    50                  55                  60

Leu Gly Ile Glu Leu Thr Pro Trp Leu Gly Phe Glu Ala Glu Tyr Asn
65                  70                  75                  80

Gln Val Lys Gly Asp Val Asp Gly Ala Ser Ala Gly Ala Glu Tyr Lys
                85                  90                  95

Gln Lys Gln Ile Asn Gly Asn Phe Tyr Val Thr Ser Asp Leu Ile Thr
            100                 105                 110

Lys Asn Tyr Asp Ser Lys Ile Lys Pro Tyr Val Leu Leu Gly Ala Gly
        115                 120                 125

His Tyr Lys Tyr Asp Phe Asp Gly Val Asn Arg Gly Thr Arg Gly Thr
    130                 135                 140

Ser Glu Glu Gly Thr Leu Gly Asn Ala Gly Val Gly Ala Phe Trp Arg
145                 150                 155                 160

Leu Asn Asp Ala Leu Ser Leu Arg Thr Glu Ala Arg Ala Thr Tyr Asn
                165                 170                 175

Ala Asp Glu Glu Phe Trp Asn Tyr Thr Ala Leu Ala Gly Leu Asn Val
            180                 185                 190

Val Leu Gly Gly His Leu Lys Pro Ala Ala Pro Val Val Glu Val Ala
        195                 200                 205

Pro Val Glu Pro Thr Pro Val Ala Pro Gln Pro Gln Glu Leu Thr Glu
    210                 215                 220

Asp Leu Asn Met Glu Leu Arg Val Phe Phe Asp Thr Asn Lys Ser Asn
225                 230                 235                 240

Ile Lys Asp Gln Tyr Lys Pro Glu Ile Ala Lys Val Ala Glu Lys Leu
                245                 250                 255

Ser Glu Tyr Pro Asn Ala Thr Ala Arg Ile Glu Gly His Thr Asp Asn
            260                 265                 270

Thr Gly Pro Arg Lys Leu Asn Glu Arg Leu Ser Leu Ala Arg Ala Asn
        275                 280                 285

Ser Val Lys Ser Ala Leu Val Asn Glu Tyr Asn Val Asp Ala Ser Arg
    290                 295                 300

Leu Ser Thr Gln Gly Phe Ala Trp Asp Gln Pro Ile Ala Asp Asn Lys
305                 310                 315                 320

Thr Lys Glu Gly Arg Ala Met Asn Arg Arg Val Phe Ala Thr Ile Thr
                325                 330                 335

Gly Ser Arg Thr Val Val Val Gln Pro Gly Gln Glu Ala Ala Ala Pro
            340                 345                 350

Ala Ala Ala Gln
        355

<210> SEQ ID NO 17
<211> LENGTH: 27
<212> TYPE: DNA
<213> ORGANISM: Artificial Sequence
<220> FEATURE:

```
<223> OTHER INFORMATION: primer

<400> SEQUENCE: 17
ggcaggatcc gctgctgcat ttgaccc                                        27

<210> SEQ ID NO 18
<211> LENGTH: 26
<212> TYPE: DNA
<213> ORGANISM: Artificial Sequence
<220> FEATURE:
<223> OTHER INFORMATION: primer

<400> SEQUENCE: 18
cggaatgtcg acttagaatg cagttg                                         26

<210> SEQ ID NO 19
<211> LENGTH: 28
<212> TYPE: DNA
<213> ORGANISM: Artificial Sequence
<220> FEATURE:
<223> OTHER INFORMATION: primer

<400> SEQUENCE: 19
ggcaggatcc gcaacttctg ataaagag                                       28

<210> SEQ ID NO 20
<211> LENGTH: 29
<212> TYPE: DNA
<213> ORGANISM: Artificial Sequence
<220> FEATURE:
<223> OTHER INFORMATION: primer

<400> SEQUENCE: 20
caaagtcgac ttagaagcta tatttagcc                                      29

<210> SEQ ID NO 21
<211> LENGTH: 35
<212> TYPE: DNA
<213> ORGANISM: Artificial Sequence
<220> FEATURE:
<223> OTHER INFORMATION: primer

<400> SEQUENCE: 21
tcgcggatcc caaggtttag tgcttaataa tgatg                               35

<210> SEQ ID NO 22
<211> LENGTH: 32
<212> TYPE: DNA
<213> ORGANISM: Artificial Sequence
<220> FEATURE:
<223> OTHER INFORMATION: primer

<400> SEQUENCE: 22
cgacaagctt agaaaccaaa cattttacgc tc                                  32

<210> SEQ ID NO 23
<211> LENGTH: 29
<212> TYPE: DNA
<213> ORGANISM: Artificial Sequence
<220> FEATURE:
<223> OTHER INFORMATION: primer

<400> SEQUENCE: 23
cttgtggatc ccaaagttcg gctgagacc                                      29
```

<210> SEQ ID NO 24
<211> LENGTH: 36
<212> TYPE: DNA
<213> ORGANISM: Artificial Sequence
<220> FEATURE:
<223> OTHER INFORMATION: primer

<400> SEQUENCE: 24
aaagtcgact taaagttgtg gaccaataaa gaaatg                              36

<210> SEQ ID NO 25
<211> LENGTH: 31
<212> TYPE: DNA
<213> ORGANISM: Artificial Sequence
<220> FEATURE:
<223> OTHER INFORMATION: primer

<400> SEQUENCE: 25
aaaggatcca gagcatatgc ttttcatagt g                                   31

<210> SEQ ID NO 26
<211> LENGTH: 37
<212> TYPE: DNA
<213> ORGANISM: Artificial Sequence
<220> FEATURE:
<223> OTHER INFORMATION: primer

<400> SEQUENCE: 26
aaagtcgact taagatggtc ggactacttg gtcttct                             37

<210> SEQ ID NO 27
<211> LENGTH: 30
<212> TYPE: DNA
<213> ORGANISM: Artificial Sequence
<220> FEATURE:
<223> OTHER INFORMATION: primer

<400> SEQUENCE: 27
ggacgaggat ccgctgatgg tacaattaca                                     30

<210> SEQ ID NO 28
<211> LENGTH: 30
<212> TYPE: DNA
<213> ORGANISM: Artificial Sequence
<220> FEATURE:
<223> OTHER INFORMATION: primer

<400> SEQUENCE: 28
aactaagctt tcaacccatt gattgagcac                                     30

<210> SEQ ID NO 29
<211> LENGTH: 27
<212> TYPE: DNA
<213> ORGANISM: Artificial Sequence
<220> FEATURE:
<223> OTHER INFORMATION: primer

<400> SEQUENCE: 29
aatactggat ccgctgttac tggtcag                                        27

<210> SEQ ID NO 30
<211> LENGTH: 36
<212> TYPE: DNA
<213> ORGANISM: Artificial Sequence
<220> FEATURE:
<223> OTHER INFORMATION: primer

```
<400> SEQUENCE: 30
aactaagctt ttagaaattt acagtgacta atagag                           36

<210> SEQ ID NO 31
<211> LENGTH: 28
<212> TYPE: DNA
<213> ORGANISM: Artificial Sequence
<220> FEATURE:
<223> OTHER INFORMATION: primer

<400> SEQUENCE: 31
ctgctgaatt cggcgtaaca gttactcc                                    28

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
caagaaagct tattattgag                                             20

<210> SEQ ID NO 33
<211> LENGTH: 19
<212> TYPE: DNA
<213> ORGANISM: Artificial Sequence
<220> FEATURE:
<223> OTHER INFORMATION: primer

<400> SEQUENCE: 33
taatacgact cactatagg                                              19

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
tgctagttat tgctcagcgg                                             20

<210> SEQ ID NO 35
<211> LENGTH: 22
<212> TYPE: DNA
<213> ORGANISM: Artificial Sequence
<220> FEATURE:
<223> OTHER INFORMATION: primer

<400> SEQUENCE: 35
cgggtgcgcc agatgattta gc                                          22

<210> SEQ ID NO 36
<211> LENGTH: 8
<212> TYPE: PRT
<213> ORGANISM: Acinetobacter baumannii
<220> FEATURE:
<223> OTHER INFORMATION: epitope

<400> SEQUENCE: 36

Pro Val Asp Phe Thr Val Ala Ile
                5
```

TARGETS OF *ACINETOBACTER BAUMANNII*

CROSS-REFERENCE TO RELATED APPLICATIONS

This application is a 371 application of PCT/EP2012/004939, Novel Targets of *Acinetobacter Baumannii*, by Simon Urwyler, et al, filed Nov. 29, 2012, and which claims priority to and benefit of: European Patent Application 11191320.8, filed Nov. 30, 2011. The full disclosure of the prior application is incorporated herein by reference.

FIELD OF THE INVENTION

The present invention relates to antigenic polypeptides expressed during an infection by a pathogenic organism, such as *Acinetobacter* and compositions comprising these polypeptides. The invention further relates to their use in treating, preventing or detecting a bacterial infection, in particular the use of the antigenic polypeptides in vaccination. The invention further relates to antibodies directed to said antigenic polypeptides.

BACKGROUND ART

*Acinetobacter* spp. are widely distributed in nature. The genus *Acinetobacter* is divided into about 20 species. They are gram-negative, oxidase-negative, non-motile, nitrate-negative, non-fermentative bacteria.

*Acinetobacter baumannii* is the most frequently isolated species in this genus. They are able to survive on various surfaces (both moist and dry) in the hospital environment. *A. baumannii* has only recently been recognized as a nosocomial pathogen. Invasive techniques such as surgery, and pulmonary ventilation combined with immunocompromized patients, have led to the increased importance of the *Acinetobacter* genus as nosocomial pathogens.

The frequencies of both nosocomial and community-acquired infections have increased steadily over the years. In addition, treatment of these infections has become more challenging due to the emergence of (multi)-drug resistant strains.

*Acinetobacter* infections are usually diagnosed through symptoms for aerobic bacterial infections in combination with microbial cultures of body fluids originating from the infected tissue. The cultured bacteria are then identified in vitro. A variety of genotypic methods has been explored and applied to investigate the diversity or phylogeny in the genus. These methods include high-resolution fingerprinting with AFLP, PCR-RFLP with digestion of PCR amplified sequences, and analysis of various DNA sequences.

One of the most important developments in recent medical history is the development of vaccines which provide prophylactic protection from a wide variety of pathogenic organisms. Many vaccines are produced by inactivated or attenuated pathogens which are injected into an individual. The immunized individual responds by producing both a humoral (antibody) and cellular (cytolytic and/or helper and/or regulatory T cells etc) response.

However the use of attenuated organisms in vaccines for certain diseases is problematic due to the lack of knowledge regarding the pathology of the condition and the nature of the attenuation. An alternative to the use of inactivated or attenuated pathogens is the identification of pathogen epitopes to which the immune system is particularly sensitive. In this regard many pathogenic toxins produced by pathogenic organisms during an infection are particularly useful in the development of vaccines which protect the individual from a particular pathogenic organism.

A so-called subunit vaccine presents an antigen to the immune system without introducing pathogenic particles, such as viruses, whole or otherwise. Mostly such subunit vaccines are produced by recombinant expression of an antigen in a host organism, purification from the host organism and preparation of a vaccine composition.

In general, *Acinetobacter* species are considered non-pathogenic to healthy individuals. The recently recognized clinical importance of *Acinetobacter* species has stimulated interest in understanding the various bacterial and host components involved in the pathogenesis of these diseases. The knowledge of the interaction plays an important role in controlling the infection. *Acinetobacter* infections usually involve organ systems that have a high fluid content (e.g. respiratory tract, CSF (cerebrospinal fluid), peritoneal fluid, urinary tract), manifesting as nosocomial pneumonia, infections associated with continuous ambulatory peritoneal dialysis (CAPD), or catheter-associated bacteriuria.

Pantophlet et al. describe O antigens of *Acinetobacter* lipopolysaccharides (LPS) and corresponding antibodies for identification of *Acinetobacter* isolates (Pantophlet R. et al., *Clinical and Diagnostic Laboratory Immunology*, 9, 60-65 (2002)).

Tomarasz et al. identified the polycistronic csuAB gene cluster and showed its importance in the production and assembly of pili as well as in the subsequent formation of biofilms, e.g. on hospital surfaces and medical devices (Tomarasz A. P. et al., *Microbiology*, 154, 3398-3409 (2008)).

U.S. Pat. No. 6,562,958 discloses about 4000 nucleic acid and amino acid sequences relating to *A. baumannii*, however, they are mostly with unidentified function. U.S. Pat. No. 6,713,062 discloses OmpA and OmpA like protein being capable of stimulating gastrin and IL-8 gene expression.

However, no vaccines were developed as of today. Vaccines based on surface-exposed and secreted proteins against *Acinetobacter* infections have not been developed yet due to a lack of availability of feasible targets.

Therefore, there is a high medical need in the art for antigenic polypeptides expressed during an infection by *Acinetobacter*, preferably *A. baumannii*, and which are suitable for vaccine development and which are feasible for production of diagnostic, prophylactic and therapeutic antibodies.

A number of methods have been developed to identify potential antigenic polypeptides from various pathogens, however, they do not provide a general tool to prove the suitability of such polypeptides as immunogenic target in a vaccine composition.

Accordingly, the technical problem underlying the present invention is to provide clinically prevalent *A. baumannii* targets to be used in a vaccine composition and/or for production of diagnostic, prophylactic and therapeutic valuable antibodies.

The technical problem is solved by the provision of nucleic acids encoding antigenic polypeptides and antibodies or antibody-binding fragments that bind the antigenic polypeptides.

SUMMARY OF THE INVENTION

The present invention provides a vaccine composition comprising at least one polypeptide encoded by a nucleic acid molecule comprising a polynucleotide selected from the group consisting of:

a) a polynucleotide having the nucleic acid sequence depicted in any one of SEQ ID NOs: 1, 3, 5, 7, 9, 11, 13 and 15;
b) a polynucleotide encoding a fragment, analog or functional derivative of a polypeptide encoded by the polynucleotide of (a), wherein said fragment, analog or functional derivative has immunostimulatory activity;
c) a polynucleotide encoding a polypeptide having an amino acid sequence that is at least 80% identical to the amino acid sequence depicted in any one of SEQ ID NOs: 2, 4, 6, 8, 10, 12, 14, and 16 and having immunostimulatory activity;
d) a polynucleotide which is at least 80% identical to the polynucleotide of (a), and which encodes a polypeptide having immunostimulatory activity;
e) a polynucleotide which hybridizes under stringent conditions to the polynucleotide of any one of (a) to (d); and
f) a polynucleotide that is complementary to the full length of a polynucleotide of any of (a) to (d).

Preferably said nucleic acid molecule is genomic DNA.

In one embodiment of the invention, said polypeptide is derived from the genus *Acinetobacter*; preferably said polypeptide is derived from the species *Acinetobacter baumanii*.

In another embodiment of the invention, the vaccine composition further comprises a pharmaceutically acceptable carrier and/or adjuvant.

In another embodiment, the present invention provides an antigenic polypeptide consisting of an amino acid sequence depicted in any one of SEQ ID NOs: 2, 4, 6, 8, 10, 12, 14 and 16; or fragment, analog or functional derivative thereof, wherein said fragment, analog or functional derivative has immunostimulatory activity.

In further embodiments, the present invention provides a nucleic acid molecule encoding the antigenic polypeptide of the invention, an expression vector comprising said nucleic acid molecule and a host cell comprising said vector and/or said nucleic acid of the invention.

In a further embodiment, the present invention provides an antibody or an antigen-binding fragment thereof that specifically binds the antigenic polypeptide of the invention, wherein said antibody or antigen-binding fragment thereof is capable of inducing an effector function towards *Acinetobacter baumanii*. The antibody provided by the invention is polyclonal or monoclonal; preferably human. Said antibody may be N-terminally, internally and/or C-terminally modified, such as by oligomerization, and conjugation to a drug and/or a label.

The monoclonal antibody or an antigen-binding fragment thereof of the invention preferably is capable of inducing an effector function towards *Acinetobacter baumanii*. Most preferably, the monoclonal antibody of the invention or an antigen-binding fragment thereof specifically binds the epitope consensus motif PVDFTVAI shown in SEQ ID NO: 36.

The monoclonal antibody of the invention is preferably produced from a human B cell or a hybridoma obtained by fusion of said human B cell with a myeloma or heteromyeloma cell. The invention thus provides a hybridoma capable of producing the monoclonal antibody of the invention. The invention further provides a nucleic acid encoding the light chain and the heavy chain of the inventive antibody and a vector comprising said nucleic acid as well as a host cell comprising said vector and/or said nucleic acid.

In a further embodiment, the present invention provides a method for producing the monoclonal antibody of the invention comprising culturing the hybridoma as defined herein under conditions allowing for secretion of an antibody, and optionally purifying the antibody from the culture supernatant.

In a further embodiment, the present invention provides a pharmaceutical composition comprising the antigenic polypeptide or the antibody of the invention and a pharmaceutically acceptable carrier. In a further embodiment, the present invention provides a diagnostic composition comprising the antigenic polypeptide or the antibody of the invention for detecting a bacterial infection in a patient. The antibody of the invention is provided for use in the treatment, prevention and/or detection of a bacterial infection in a mammal; preferably a human.

In a further embodiment, the present invention provides a polypeptide for use in the treatment and/or prevention of a bacterial infection in a mammal encoded by a nucleic acid molecule comprising a polynucleotide selected from the group consisting of:
a) a polynucleotide having the nucleic acid sequence depicted in any one of SEQ ID NOs: 1, 3, 5, 7, 9, 11, 13, and 15;
b) a polynucleotide encoding a fragment, analog or functional derivative of a polypeptide encoded by the polynucleotide of (a), wherein said fragment, analog or functional derivative has immunostimulatory activity;
c) a polynucleotide encoding a polypeptide having an amino acid sequence that is at least 80% identical to the amino acid sequence depicted in any one of SEQ ID NOs: 2, 4, 6, 8, 10, 12, 14, and 16 and having immunostimulatory activity;
d) a polynucleotide which is at least 80% identical to the polynucleotide of (a), and which encodes a polypeptide having immunostimulatory activity;
e) a polynucleotide which hybridizes under stringent conditions to the polynucleotide of any one of (a) to (d); and
f) a polynucleotide that is the complement of the full length of a polynucleotide of any of (a) to (d).

Preferably the mammal is human. In a further embodiment of the present invention the bacterial infection to be treated, prevented and/or detected is caused by *Acinetobacter baumanii*, said bacterial infection may be hospital-acquired. The antigenic polypeptide compositions for use according to invention may further comprise a delivery vehicle; preferably a virosome.

Antigenic polypeptides according to the invention were recombinantly expressed, purified and tested by ELISA with sera from convalescent *A. baumannii* patients and ordinary, randomly selected blood donors in different dilutions. Numbers within the charts reflect the number of sera tested and reacting with the antigenic polypeptide (A-H) at a dilution as indicated by the different colours given in the legend.

Titres are defined as the highest serum dilution that generates an antigen specific ELISA signal twice the signal of the corresponding blank. The majority of patient sera tested contain antibodies against the targets identified by the present invention. The patient sera contain generally higher titers compared to healthy blood donors. For all antigens, individual patient sera could be identified with extremely high antibody titers ($\geq 1/6400$), proving that the antigens are immunogenic in human and are expressed during infection.

This strongly indicates that these newly identified targets are feasible for vaccine development and generation of prophylactic/therapeutic antibodies.

A: His-AB023 corresponding to SEQ ID NO: 2; B: His-AB024 corresponding to SEQ ID NO: 4; C: His-AB025 corresponding to SEQ ID NO: 6; D: His-AB030 corresponding to SEQ ID NO: 8; E: His-AB031L1 corresponding to SEQ ID NO: 10; F: His-FimA corresponding to SEQ ID NO: 12; G: His-CsuAB corresponding to SEQ ID NO: 14; H: His-OmpA corresponding to SEQ ID NO: 16.

Figure 2:
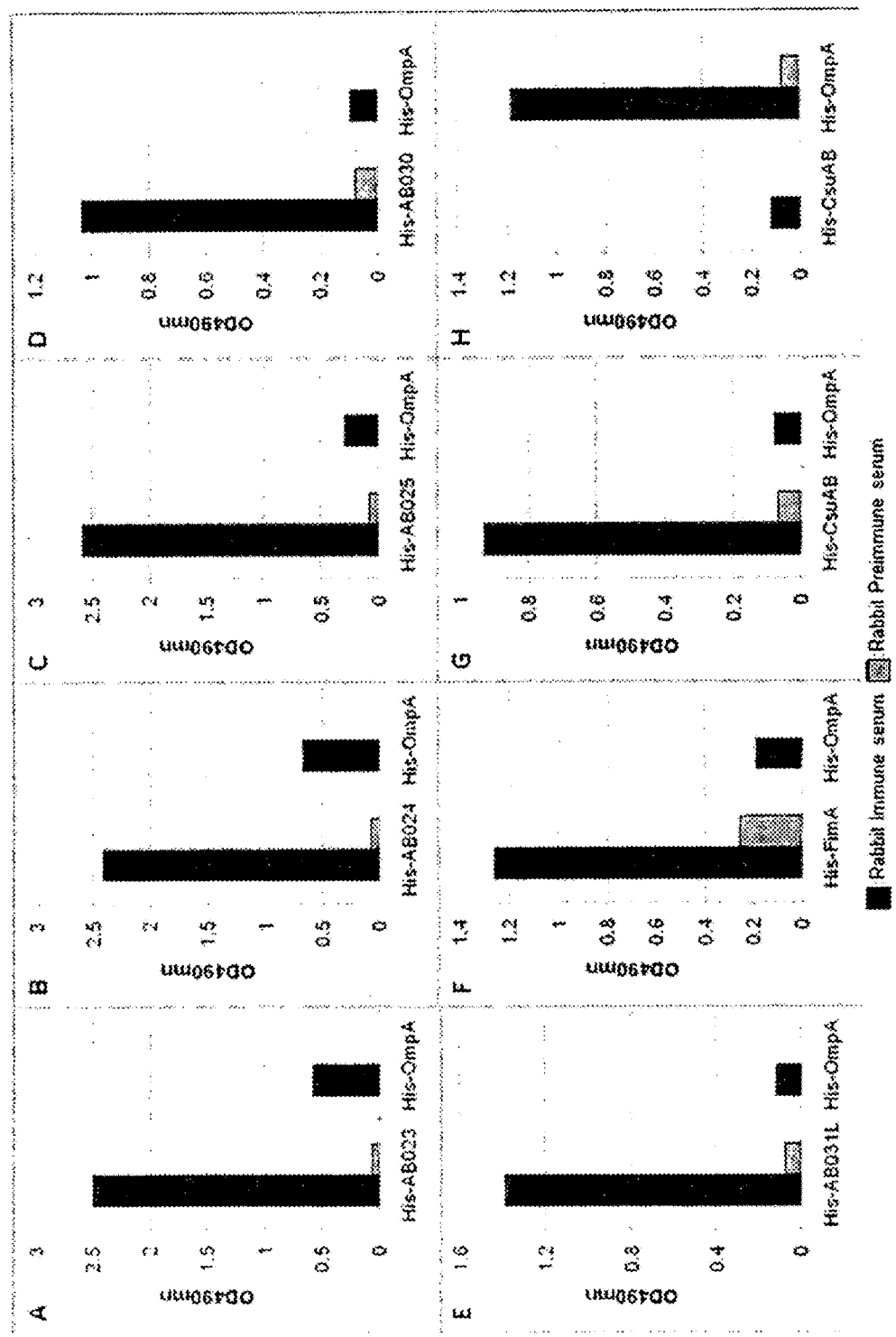

FIG. 2 shows an ELISA from rabbit sera.

Rabbits were immunized with a recombinant his-tagged antigenic polypeptide. Final bleed and pre-immune sera were tested via ELISA on ELISA plates coated individually with the different antigenic polypeptides. In addition the final bleeds were tested via ELISA on plates coated with control reagents: His-tagged OmpA which served as a control for A-G and His-CsuAB which served as a control for H. The Figures show that the major immune response is caused by the target and not by the His-tag which is present on the control as well. Comparable results were obtained with a duplicate set of immunized rabbits. The immune and preimmune sera dilutions used were:

A: α-His-AB023 (1:6400); B: α-His-AB024 (1:6400); C: α-His-AB025 (1:6400); D: α-His-AB030 (1:25600); E: α-His-AB031L1 (1:12800); F: α-His-FimA (1:400); G: α-His-CsuAB (1:3200); H: α-His-OmpA (1:6400).

Figure 3:
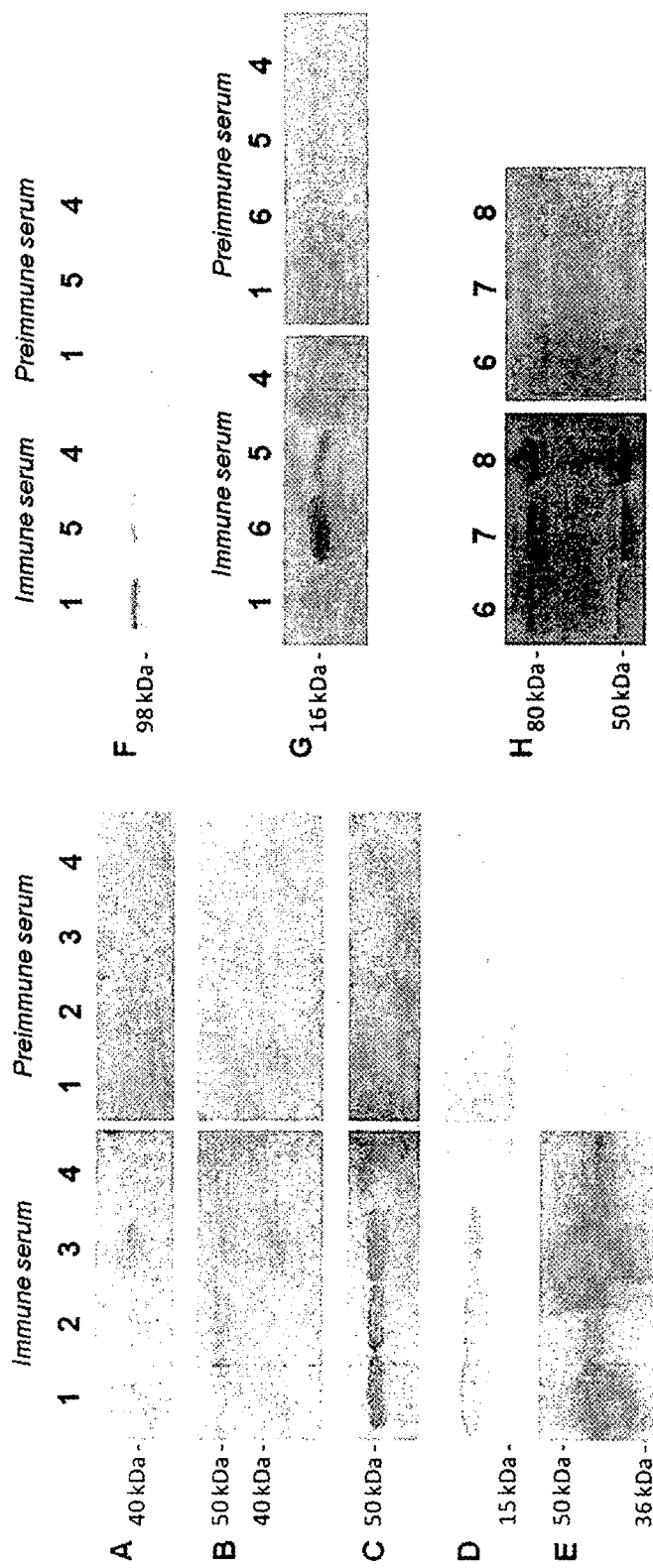

FIG. 3 shows an immunoblot analysis.

The specificity of the rabbit antisera was tested. Cell lysates from various *A. baumannii* (AB) and *P. aeruginosa* (PA) strains as negative controls, respectively were prepared, proteins separated on SDS-PAGE and blotted onto nitrocellulose. Rabbit sera against the different polypeptides (immune sera) and pre-immune sera were used at a dilution 1:1000 (experimental details given in Example 6).

Figure 4:
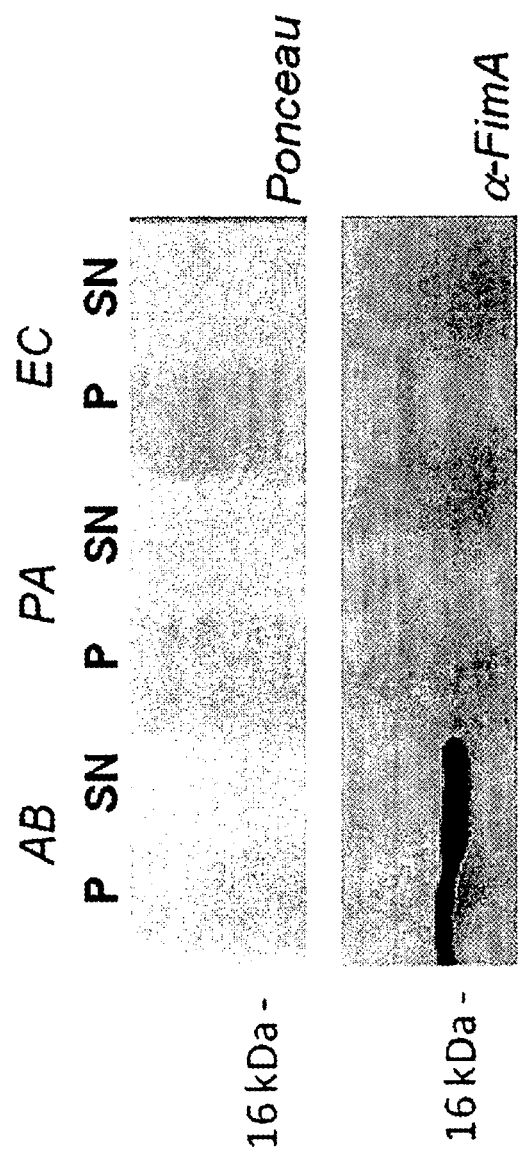

Bacterial lysates: 1: AB: ATCC19606 wild type; 2: AB: ATCC19606 OmpA K.O; 3: AB: ATCC19606; CsuE K.O; 4: PA O11; 5: AB: AB-N; 6: AB: Luh8168; 7: AB: Ruh134; 8: AB: SAN;

Immune-sera: A: α-His-AB023; B: α-His-AB024; C: α-His-AB025; D: α-His-CsuAB; E: α-His-OmpA; F: α-His-AB030; G: α-His-FimA; H: α-His-AB031L1;

FIG. 4 shows another immunoblot analysis.

The specificity of the rabbit antiserum specific for the polypeptide FimA was tested within culture supernatant. FIG. 4 shows a representative immunoblot of an *A. baumannii* (AB-Non-mucoid), a *P. aeruginosa* (PA O11) and an *E. coli* (DH5α) strain.

Overnight bacteria cultures were centrifuged and the proteins within the supernatant precipitated. The cell pellets (P) and precipitated supernatant (SN) of equivalent culture volumes were examined by immunoblot analysis for the presence of FimA using a-His-FimA rabbit antiserum. A total of 29 *A. baumannii* strains were analyzed by immunoblotting for the presence of FimA within the supernatant as well as the bacterial pellet. 45% contained detectable amounts in the cell pellet while 55% contained detectable amounts in the SN.

AB: *A. baumannii* strain AB-NM (Non-mucoid); PA: *P. aeruginosa* O11; EC: *E. coli* DH5α

Figure 5:
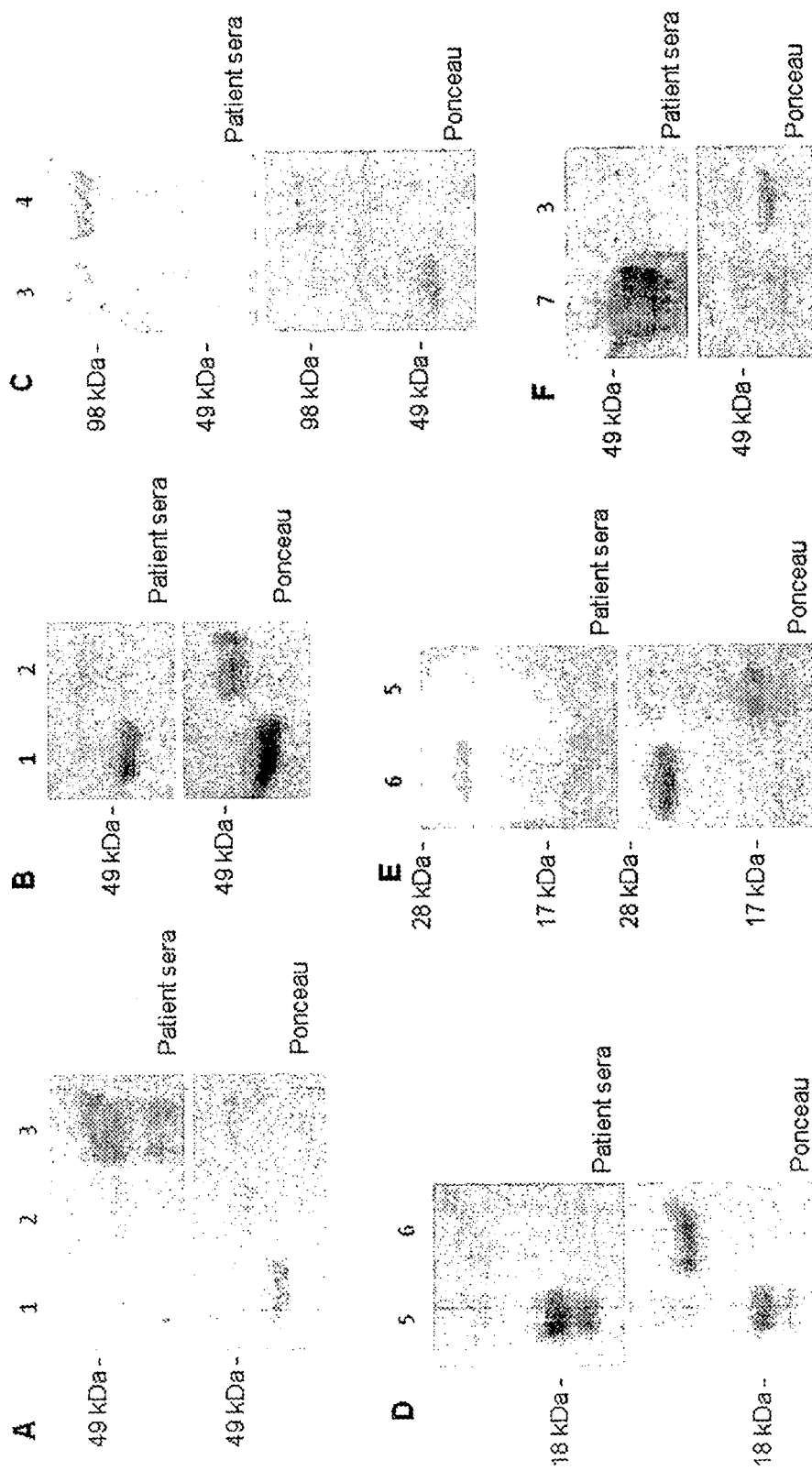

FIG. 5 shows another immunoblot analysis.

The specificity of the selected human sera was tested by immunoblot analysis. Recombinant proteins were separated on SDS-PAGE and blotted onto nitrocellulose. Different patient sera (A-F) were used against the different polypeptides (1-7) at a dilution of 1:500 (experimental details are given in Example 6). To exclude artefacts of antibodies directed against the His-tag, combinations of recombinant antigens were chosen to include with each immunoblot a His-tagged protein as negative control that is not recognized by the corresponding patient serum.

Recombinant proteins: 1—His-AB023; 2—His-AB024; 3—His-AB025; 4—His-AB030; 5—His-FimA; 6—His-CsuAB; 7—His-OmpA; 8—AB031-L1 (no human sera identified yet for AB031 L1 on immunoblots).

Figure 6:
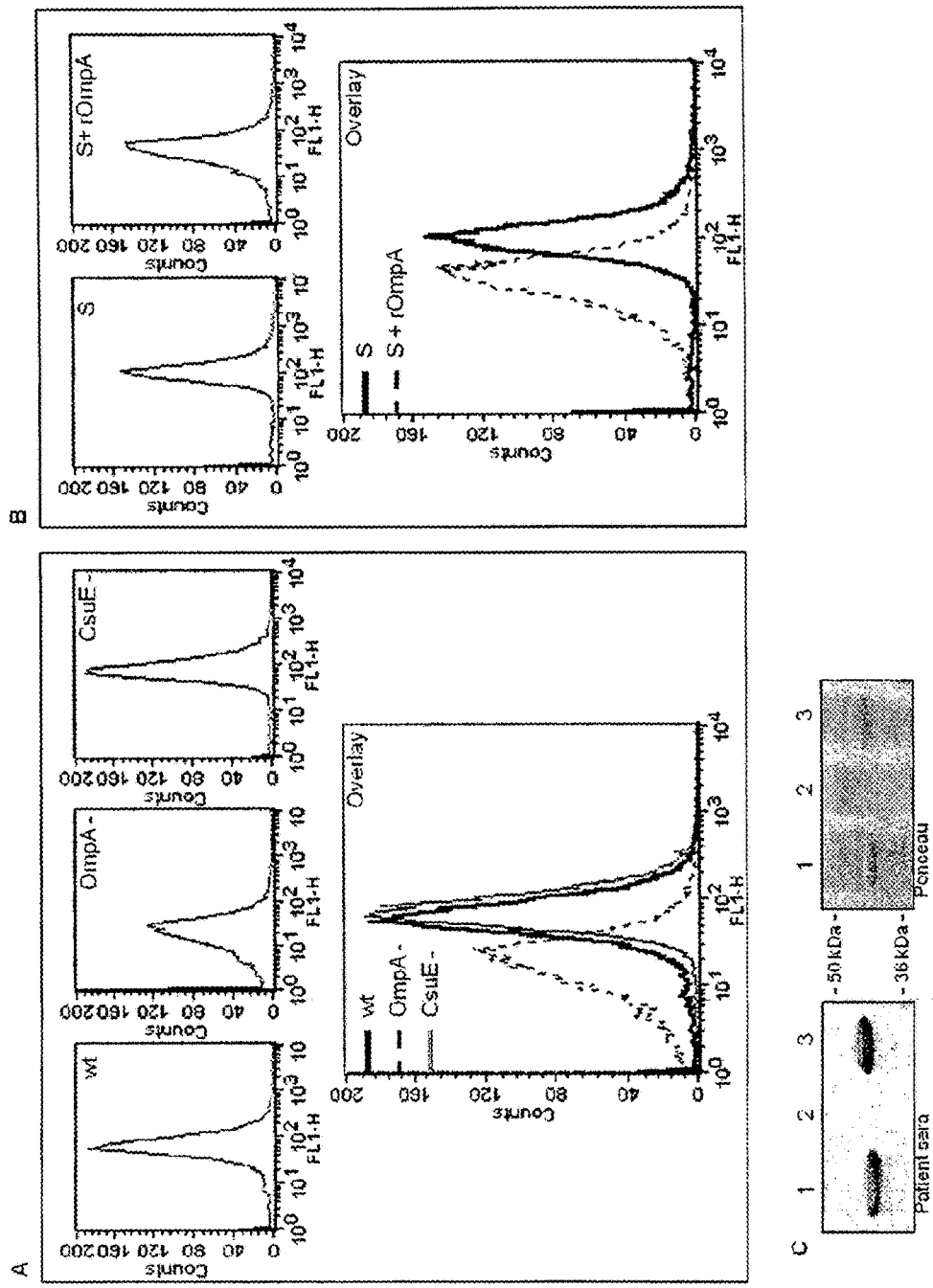

FIG. 6 shows a FACS analysis; wherein picture A shows FACS analysis of *A. baumannii* strains ATCC19606 wild type (wt), OmpA KO (OmpA-) and CsuE KO (CsuE-) using a patient sera at a dilution of 1:200. Bacterial population was gated using forward and sideward scatter and 20'000 bacteria were measured;

picture B shows FACS analysis of *A. baumannii* strains ATCC19606 wild type (wt) using the same patient sera and instrument settings as in A. Patient serum was used without (S) or with recombinant OmpA (S+rOmpA) as inhibitory agent; and picture C shows an immunoblot analysis using patient sera of cell lysates of *A. baumannii* ATCC19606 wild type (1), OmpA KO (2) as negative control and CsuE KO (3). Ponceau stain of blot confirms equal loading of cell lysates. The protein band of OmpA in cell lysates of ATCC19606 wild type and CsuE KO is apparent as well with the Ponceau stain.

Figure 7:
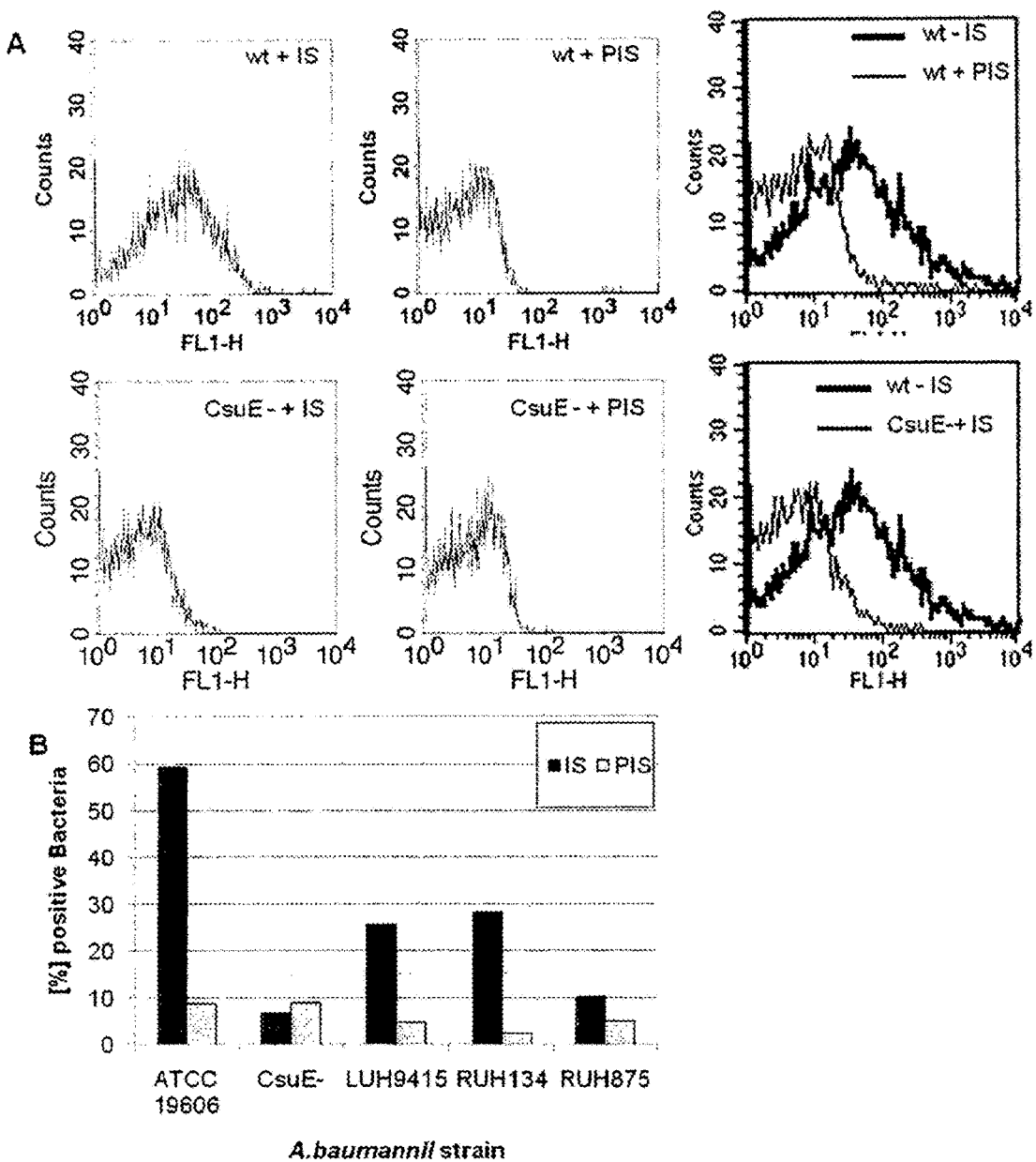

FIG. 7 relates to another FACS analysis; wherein picture A shows FACS analysis of *A. baumannii*, strains ATCC19606 (wt) and CsuE-KO (CsuE-) with indirectly fluorescence labelled αCsuAB rabbit immune serum (IS) or corresponding preimmune serum (PIS). As secondary antibody, FITC labelled goat-anti-rabbit-IgG was used. Histogram charts blotting the fluorescence signal intensity to number of events was prepared from gated bacteria. Bacterial population was gated using forward and sideward scatter and 5'000 bacteria were measured.

picture B shows FACS analysis of different *A. baumannii* strains (ATCC 19606, CsuE KO, Luh9415, Ruh134, Ruh875). The chart shows the percentage of bacteria that were indirectly fluorescence labelled with αCsuAB rabbit immune serum (IS) or corresponding preimmune serum (PIS). Bacteria were considered positive with a FL1-H signal intensity of >20.

Figure 8:
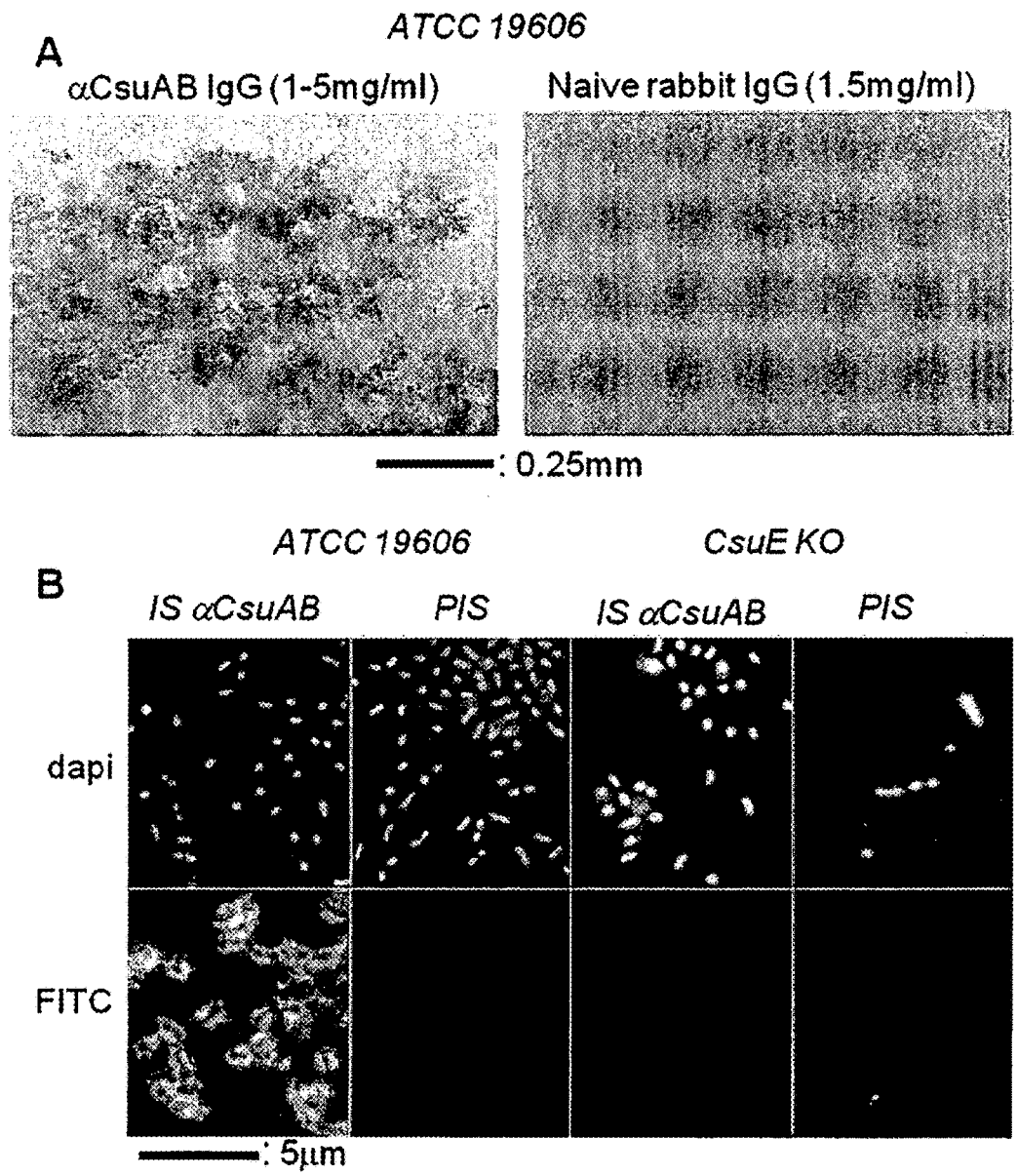

FIG. 8 shows the results of an agglutination assay and an immunofluorescence analysis; wherein picture A shows an agglutination of live *A. baumannii* (Strain ATCC19606) using 1.5 mg/ml total rabbit IgG, purified from αCsuAB rabbit immuneserum or naive rabbit serum; and picture B shows an immunofluorescence analysis of *A. baumannii* (Strains ATCC 19606 and CsuE KO). Bacteria were grown on glass slides for 24 h in cell culture medium (IMDM) containing 10% FCS. Bacteria were labelled with DAPI to localize bacterial DNA (top Figures) and indirectly fluorescence labelled using αCsuAB rabbit immune serum (IS) or corresponding preimmune serum (PIS) with FITC labelled secondary antibody (bottom Figures).

Figure 9:
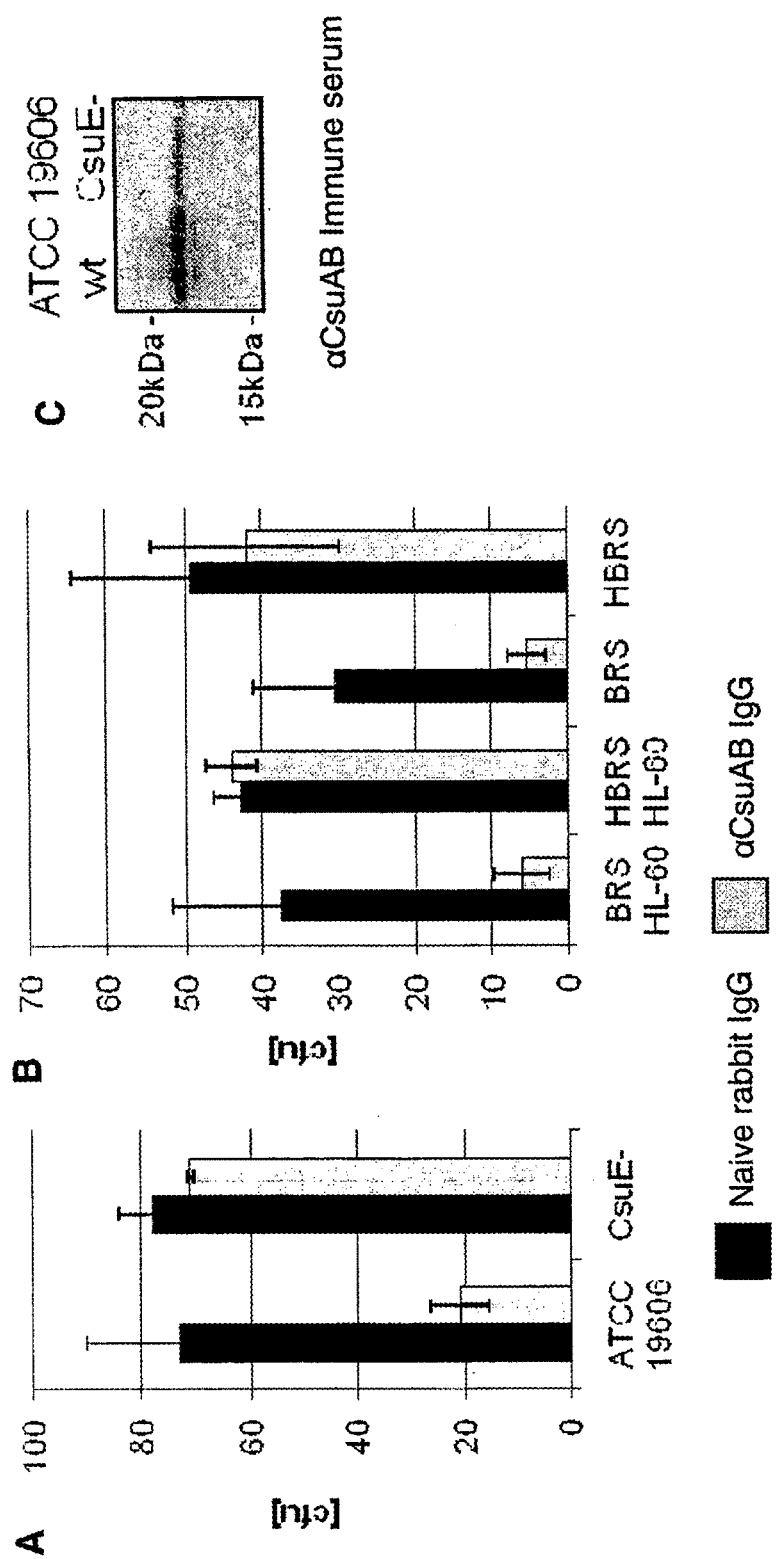

FIG. 9 shows a bactericidal assay and an immunoblot analysis; wherein pictures A and B show the bactericidal assay. The charts shows the number of colony forming units (cfu) after incubation with purified IgG from rabbit CsuAB immune serum (grey bars) or from naive rabbit serum (black bars); wherein A relates to logarithmic growing *A. baumannii*, ATCC 19606 and CsuE KO (CsuE-), which were incubated with antibody (0.5 µg/well) for 20 minutes at 37° C. As complement source baby rabbit serum (BRS) was added and incubated for 2 h. Eventually cfu were quantified by plating onto LBA; and B relates to logarithmic growing *A. baumannii* Ruh 134, which was incubated with antibody (5 µg/well) for 20 minutes at 37° C. As complement source baby rabbit serum (BRS) or as control heat inactivated BRS (HBRS) were added and supplemented with or without HL-60 cells (+HL60) previously transformed to neutrophils. Mixtures were incubated further for 2 h. Eventually cfu were quantified by plating onto LBA.

A and B: error bars show Standard deviation of three independent wells; Student's T-test (equal variance, 2-tailed) show statistical significance of <0.05 for: ATCC19606/αCsuAB compared with CsuE-/αCsuAB; ATCC19606/αCsuAB compared with ATCC19606/Naive IgG; Ruh134+BRS+HL60/αCsuAB compared with Ruh134+HBRS+HL60/αCsuAB; Ruh134+BRS+HL60/αCsuAB compared with Ruh134+BRS+HL60/Naive IgG; Ruh134+BRS/αCsuAB compared with Ruh134+HBRS/αCsuAB; Ruh134+BRS/αCsuAB compared with Ruh134+BRS/Naive IgG.

Figure 10:
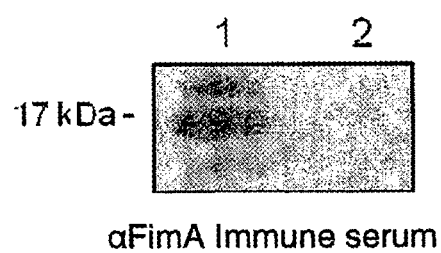

Picture C shows an immunoblot analysis of wild type and CsuE KO *A. baumannii* of the strain ATCC19606; and FIG. 10 shows the result of an FimA pulldown assay; wherein total IgG (10 µg) from FimA rabbit immune serum (1) was coated onto Protein A beads (20 µl bed volume) and used to capture native FimA from *A. baumannii* culture supernatant (0.4 ml) of the strain Luh9415, known to secrete FimA into the SN. Equal amounts of total IgG from a naive rabbit serum (2) was used as negative control. Total captured proteins were released into SDS-PAGE sample buffer by boiling for 10 min and 7% were separated by SDS-PAGE. Native FimA was visualized by immunoblot analysis using αFimA immuneserum at a dilution of 1:1000.

FIG. 11 shows passive immunization with CsuAB rabbit immune sera.

Neutropenic mice were infected with *A. baumannii* after i.p. injection with either 0.15 ml immune serum (solid lines) or an equal volume of serum from a naive animal (dashed lines). Survival of mice was recorded for 4-5 days. The virulence of the *A. baumannii* strain varied between different strains and dates of executions. Experiments B and C were performed in parallel while the experiment shown in A was performed on a separate date.

Picture A shows Strain AB-M, 10 animals per group; picture B shows Strain AB-M, 14 animal per group, and picture C shows strain AYE, 14-15 animals per group.

Figure 12:
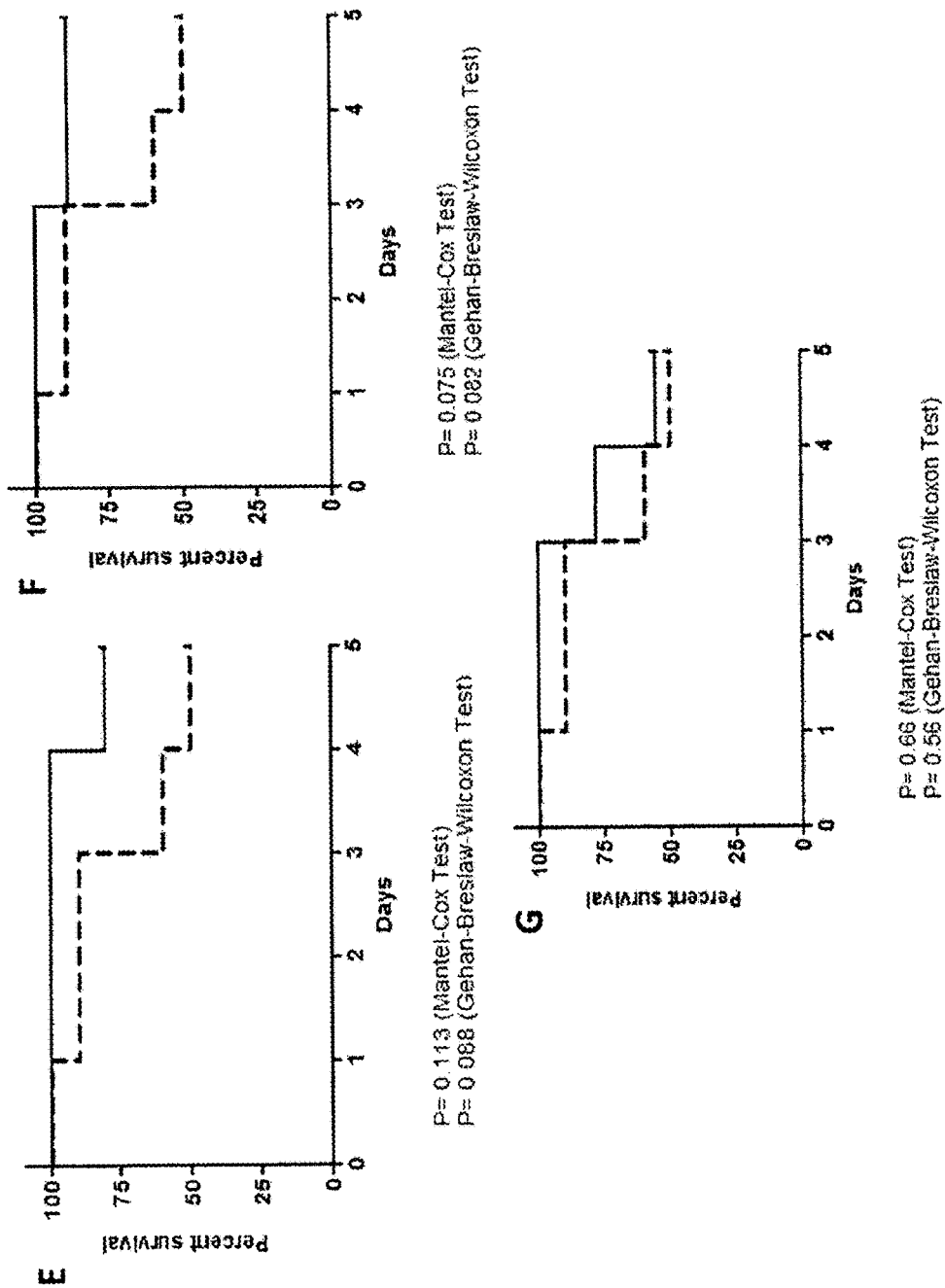

FIG. 12 shows an active immunization experiment. Mortality in a model for *A. baumannii* induced pneumonia model after active immunization. Mice were vaccinated with antigens (solid lines A-F: A: AB025—9 animals, B: AB030—10 animals, C: AB031L1—9 animals, D: FimA—9 animals, E: CsuAB—10 animals, F: OmpA—9 animals) and pneumonia was induced afterwards by intra-tracheal inoculation of *A. baumannii* (strain AB-M). As a control, a group of mice was vaccinated with the adjuvant only (dashed line A-G; 10 animals). In a second control group PBS was used instead of a vaccine or adjuvant (solid line G; 9 animals). For all antigens tested (A-F), a beneficial effect of the vaccine compared to the adjuvant control group was observed. A statistically significant effect was observed for AB030, while the other antigens just missed the threshold of 5% for statistical significance. Two reasons might contribute to this effect. Firstly, the low number of animals and, secondly the lower mortality of the control groups (G), as compared to previous experiments. The mortality was most likely lower because the animals in active immunization experiments are much older than those used in passive immunization. This is due to the duration of the active immunization protocol of several weeks.

Figure 13:
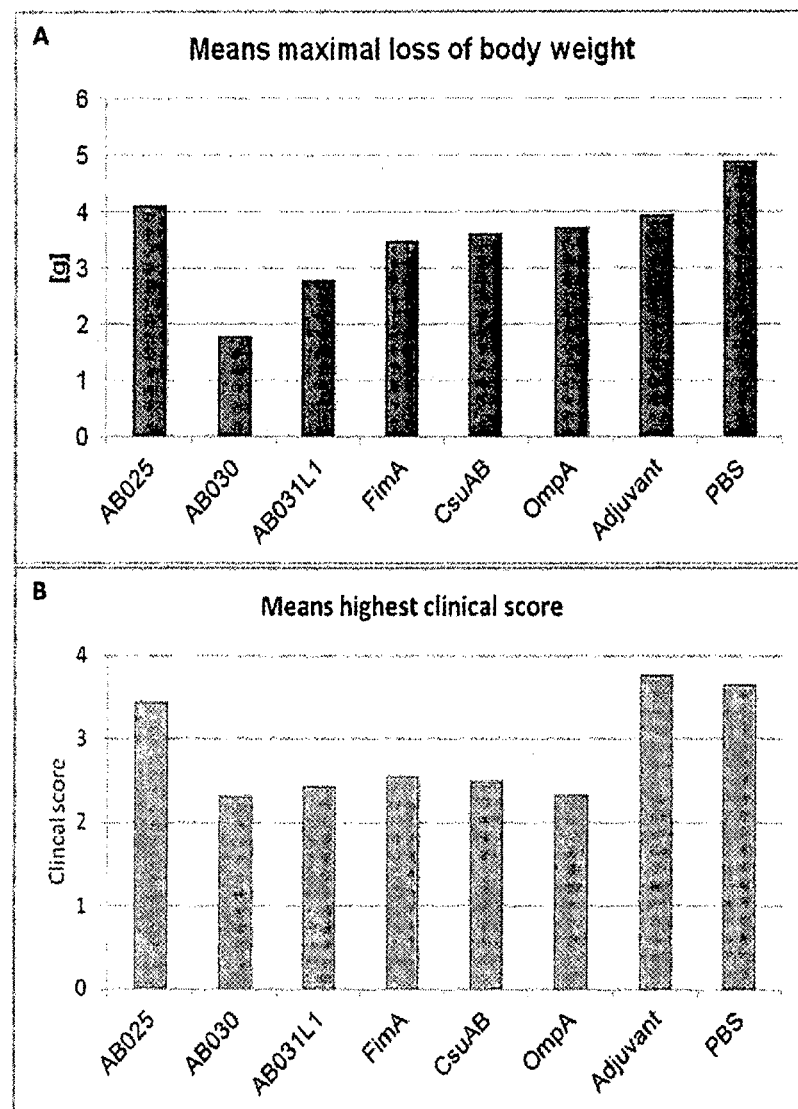

FIG. 13 shows a passive immunization experiment. Mice were rendered transiently neutropenic by intra-peritoneal injection of cyclophosphamide on days 4 and 3 before *A. baumannii* inoculation. On day 0, 3 h before *A. baumannii* inoculation, mice were passively vaccinated intraperitoneally with either 0.15 ml rabbit antiserum, naïve rabbit serum or PBS. Pneumonia was induced analogous to the active immunization protocol. Survival, clinical score and body weight were monitored.

DETAILED DESCRIPTION OF THE INVENTION

According to the present invention a vaccine composition is provided comprising at least one polypeptide encoded by a nucleic acid molecule comprising a polynucleotide selected from the group consisting of a) a polynucleotide having the nucleic acid sequence depicted in any one of SEQ ID NOs: 1, 3, 5, 7, 9, 11, 13 and 15;

b) a polynucleotide encoding a fragment, analog or functional derivative of a polypeptide encoded by the polynucleotide of (a), wherein said fragment, analog or functional derivative has immunostimulatory activity;

c) a polynucleotide encoding a polypeptide having an amino acid sequence that is at least 80% identical to the amino acid sequence depicted in any one of SEQ ID NOs: 2, 4, 6, 8, 10, 12, 14 and 16 and having immunostimulatory activity;

d) a polynucleotide which is at least 80% identical to the polynucleotide of (a), and which encodes a polypeptide having immunostimulatory activity;

e) a polynucleotide which hybridizes under stringent conditions to the polynucleotide of any one of (a) to (d); and f) a polynucleotide that is complementary to the full length of a polynucleotide of any of (a) to (d).

The polypeptides of the invention, as referred to herein, are summarized in Table 1 below:

TABLE 1

| Polypeptide | Amino acid sequence | Nucleic acid sequence |
|---|---|---|
| AB023 | SEQ ID NO: 2 | SEQ ID NO: 1 |
| AB024 | SEQ ID NO: 4 | SEQ ID NO: 3 |
| AB025 | SEQ ID NO: 6 | SEQ ID NO: 5 |
| AB030 | SEQ ID NO: 8 | SEQ ID NO: 7 |
| AB031 | SEQ ID NO: 10 | SEQ ID NO: 9 |
| FimA | SEQ ID NO: 12 | SEQ ID NO: 11 |
| CsuAB | SEQ ID NO: 14 | SEQ ID NO: 13 |
| OmpA | SEQ ID NO: 16 | SEQ ID NO: 15 |

The term "fragment" as used herein refers to any fragment of the polypeptide as defined herein which has immunostimulatory activity. The fragment has a minimum length of at least 4, 8, 15, 20, 30, 50, 100 amino acids. It is preferred that the fragment comprises an epitope of 6-8 amino acids in length, a minimal length of 4-5 amino acids and a maximal length of 15 amino acids to the total length of the protein depicted in any one of SEQ ID NOs: 2, 4, 6, 8, 10, 12, 14, 16.

An "analog of a polypeptide" is meant to refer to a molecule substantially similar in function to either the entire molecule or to a fragment thereof.

The term "functional derivative" of a polypeptide means a polypeptide with a similar structure and the same biological function.

The term "immunostimulatory activity" as used herein, refers to inducing an initial immune response to an antigen. Preferably, the polypeptide having immunostimulatory activity as defined herein is capable of inducing an immune response against infection with *Acinetobacter*, most preferred the polypeptide of the invention is capable of inducing an immune response against infection with *A. baumannii*. The term 'immune response' as used herein refers to a change in antibody content in any body fluids, which are reactive with the polypeptides, as well as changes in cellular responses to the polypeptides, such as T-cells and cells of the innate immune system, as well as changes in inflammatory markers like cytokines and chemokines and other immunological markers indicative of a modulation of normal immune functions. The immune response against these pathogenic organisms was monitored with ELISA, immunoblot and the like.

The "sequence identities" as referred herein of related polypeptides and polynucleotides can be determined by means of known procedures. A sequence identity of the related polypeptides to the antigenic polypeptides depicted in any one of SEQ ID NOs: 2, 4, 6, 8, 10, 12, 14, 16 of at least 75%, more preferably 80% or 85%, and most preferred 90% or 95% is envisaged. As a rule, computer programs with algorithms taking account of the special requirements are used. For the purposes of the present invention, the computer program used for the determination of the identity between two sequences is BLASTP (for comparison of amino acid sequences) and BLASTN (for comparison of nucleotide sequences), as described e.g. by Altschul S et al., *Nucl Acid Res* 25: 3389-3402 (1997). The BLAST programs can be obtained from the National Centre for Biotechnology Information (NCBI) and from other sources (e.g. BLAST Handbook, Altschul S et al., NCB NLM NIH Bethesda Md. 20894; Altschul S et al., *J. Mol.* 215: 403-410 (1990)). For the purposes of the present invention, the BLASTN and BLASTP algorithm with the following default settings is used:

BLASTN: Scoring Parameters: Match/Mismatch Scores 1, −3; Gap costs: Existence: 5, Extension: 2; Filters and Masking: Low complexity regions selected; Mask for lookup Table only selected; Mask lower case letters not selected BLASTP: Scoring Parameters: Matrix: BLOSUM62; Gap costs: Existence: 11, Extension: 1; Compositional adjustments: Composition-based statistics 2; Filters and Masking: None selected; Program Advanced Options; −G Cost to open gap [Integer]; default=5 for nucleotides 11 proteins; −E Cost to extend gap [Integer]; default=2 nucleotides 1 proteins; −q Penalty for nucleotide mismatch [Integer]; default=−3; −r reward for nucleotide match [Integer]; default=1; −e expect value [Real]; default=10; −W wordsize [Integer]; default=11 nucleotides 3 proteins; −y Dropoff (X) for BLAST extensions in bits (default if zero); default=20 for BLASTN 7 for other programs, −X X dropoff value for gapped alignment (in bits); default=15 for all programs except for BLASTN for which it does not apply; −Z final X dropoff value for gapped alignment (in bits); 50 for BALSTN 25 for other programs.

For sequence comparison, the complete polypeptide sequence (SEQ ID NO: 2 or 4, 6, 8, 10, 12, 14 and 16, respectively) is used as the sequence to which a related sequence is compared. Specifically, to determine the identity of a polypeptide with unknown homology to e.g. the polypeptide with SEQ ID NO: 2 according to the invention, the amino acid sequence of said first polypeptide is compared to the amino acid sequence of the polypeptide shown in SEQ ID NO: 2, over the entire length of SEQ ID NO: 2. Similarly, to determine the identity of a polynucleotide with unknown homology to e.g. polynucleotide with SEQ ID NO: 1 according to the invention, the nucleic acid sequence of said first polynucleotide is compared to the nucleic acid sequence shown in SEQ ID NO: 1, over the entire length of SEQ ID NO: 1.

Standard "stringent conditions" for hybridization are disclosed in Ausubel et al. (Eds.), *Current Protocols in Molecular Biology*, John Wiley & Sons (2000). Exemplary stringent hybridization conditions include washes with 0.1×SSC/ 0.1% SDS for 15 min at 68° C.

The present invention provides a vaccine composition as defined above, wherein the nucleic acid molecule encoding a polypeptide is genomic DNA.

The nucleic acid sequences encoding the polypeptides of the present invention can be amplified by PCR from genomic DNA of an *A. baumannii* strain using primers containing appropriate restriction sites for cloning.

According to the present invention the vaccine composition comprises at least one polypeptide wherein said polypeptide is derived from the genus *Acinetobacter*.

More preferably the vaccine composition comprises at least one polypeptide wherein said polypeptide is derived from the species *Acinetobacter baumanii*.

The terms "*Acinetobacter baumannii*" or "*A. baumannii*" as used herein refer to *Acinetobacter* baumanii species as classified in *Acinetobacter Molecular Biology*, 2008, Ed.: Ulrike Gerischer, Caister Academic Press. Examples are *A. baumannii* strains SDF, AYE, ATCC 19606, ACICU Ruh134, Ruh875, AB-M, AB-NM and SAN, whose references and sources are described in Table 6. References and information regarding taxonomy and strains can be received on the Pubmed homepage.

*A. baumannii* causes different types of infections including, among others, pneumonia, bacteremia, and skin and soft tissue infections. Over the last decades *A. baumannii* has emerged as a pathogen of increasing clinical importance due to the global increase in the incidence of infections caused by this organism. Infections caused by this pathogen have been especially problematic in patients receiving mechanical ventilation and burn patients. *A. baumannii* can cause outbreaks in intensive care units and trauma/burn units, which are presumably caused by passage of the organism from infected or colonized individuals and contaminated hospital equipment to uninfected patients.

The results shown in Table 2, below prove that the targets identified by the present invention are representative of all *A. baumannii* clinical isolates tested so far. Strain SDF represents the only *A. baumannii* strain which is not a clinical isolate but was isolated from body lice. This strain is lacking the genes for FimA and CsuAB.

Table 2 below shows the percentage of amino acid identity of proteins encoded by different *A. baumannii* strains. Amino acid sequences encoded by the *A. baumannii* genome AB307, corresponding to the polypeptides identified by the present invention (SEQ ID NOs: 2, 4, 6, 8, 10, 12, 14, 16), were compared to 13 other sequenced genomes. In case of the antigen AB031 only the extracellular loop L1 was used for comparison.

TABLE 2

Conservation of amino acid identity by various A. baumannii strains

| Target | AB307 | AB056 | AB057 | AB058 | AB059 | SDF | AYE | ATCC 17978 | ATCC 19606 | ACICU | AB900 | 6013113 | 6013150 | 6014059 |
|---|---|---|---|---|---|---|---|---|---|---|---|---|---|---|
| AB023 | 100% | 100% | 100% | 100% | 100% | 99% | 100% | 99% | 99% | 100% | 99% | 100% | 99% | 100% |
| AB024 | 100% | 100% | 100% | 100% | 100% | 86% | 100% | 99% | 99% | 99% | 99% | 100% | 100% | 99% |
| AB025 | 100% | 100% | 100% | 100% | 100% | 90% | 100% | 93% | 91% | 91% | 88% | 100% | 100% | 91% |
| AB030 | 100% | 100% | 100% | 100% | 100% | 99% | 100% | 99% | 99% | 99% | 99% | 100% | 100% | 99% |
| AB031 | 100% | 100% | 100% | 100% | 100% | 100% | 100% | 100% | 100% | 100% | 97% | 100% | 100% | 100% |
| L1* |  |  |  |  |  |  |  |  |  |  |  |  |  |  |
| FimA | 100% | 100% | 100% | 100% | 100% | — | 100% | 74% | 100% | 100% | 94% | 100% | 100% | 100% |
| CsuAB | 100% | 100% | 100% | 100% | 100% | — | 100% | 100% | 100% | 100% | 100% | 100% | 100% | 100% |
| OmpA | 100% | 100% | 100% | 100% | 100% | 89% | 100% | 93% | 94% | 93% | 93% | 99% | 99% | 93% |

*loop compared only.
— no homologues detected

The high degree of amino acid identity of the proteins within various A. baumannii strains shows the broad specificity of the antigenic proteins and confirms their high therapeutic value. The high prevalence of the genes indicates that the protein is important, possibly essential, during the life cycle of the bacteria. Therefore the protein is likely expressed during infection. The high degree of conservation points increases the chance to induce an immune response or to identify a polyclonal or monoclonal antibody capable of binding most or possibly all clinically relevant A. baumannii strains. Additionally, the high degree of amino acid conservation indicates that mutations of these genes are rare, thus reducing chances for rescue mutants during therapeutic treatment.

The present invention provides a vaccine composition as defined herein wherein said vaccine composition further comprises a pharmaceutically acceptable carrier and/or adjuvant.

The term "adjuvant" as used herein refers to a substance distinct from target antigen that is capable of increasing the antigenic response. The adjuvant may be selected from Freund's adjuvants (complete and incomplete), Gerbu adjuvant (GERBU Biotechnik GmbH, Germany), mycobacteria such as BCG, M. vaccae, or Corynebacterium parvum, Cholera toxin or tetanus toxoid, E. coli heat-labile toxin, quil-saponin mixtures such as QS-21 (SmithKline Beecham), MF59 (Chiron) and various oil/water emulsions (e.g. IDEC-AF), MALP-2, ISCOMs. Other adjuvants which may be used include, but are not limited to: mineral salts or mineral gels such as aluminium hydroxide, aluminium phosphate, and calcium phosphate; surface active substances such as lysolecithin, pluronic polyols, polyanions, peptides, keyhole limpet hemocyanins, and dinitrophenol, immunostimulatory molecules, such as saponins, muramyl dipeptides and tripeptide derivatives, short nucleic acid stretches such as CpG dinucleotides, CpG oligonucleotides, monophosphoryl Lipid A, and polyphosphazenes, particulate and microparticulate adjuvants, such as emulsions, liposomes, virosomes, virus-like particles, cochleates, or immunostimulating complex adjuvants. Cytokines are also useful due to their lymphocyte stimulatory properties. Many cytokines useful for such purposes will be known to one of ordinary skill in the art, including interleukin-2 (IL-2), IL-12, GM-CSF and many others. Furthermore ligands from the chemokine family, such as RANTES, a lipoprotein, a lipopeptide, a yeast cell wall component, a double-stranded RNA, a bacterial cell-surface lipopolysaccharide (LPS), flagellin, a U-rich single-stranded viral RNA, a suppressor of cytokine signalling small interfering RNA (SOCS siRNA), a Pan DR epitope (PADRE) and mixtures thereof are suitable.

The definition of "pharmaceutically acceptable carrier" is meant to encompass any carrier, which does not interfere with effectiveness of the biological activity of the active ingredient and that is not toxic to the host to which it is administered.

Accordingly, one or more polypeptides of the invention or fragments, analogs and functional derivatives thereof may be used to prepare a prophylactic or therapeutic vaccine for administration to an individual in need thereof. Such a vaccine which contains one or more polypeptides of the present invention, as the principal or member active ingredient, can be administered in a wide variety of therapeutic/prophylactic dosage forms in the conventional vehicles for topical, mucosal (nasal, oral), systemic, local, and parenteral administration. Thus, the invention provides compositions for parenteral administration which comprise a solution of a polypeptide according to the invention optionally in combination with a suitable adjuvant and/or equivalent delivery vehicles dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, among many others. Actual methods for preparing parenterally administrable compounds will be known or apparent to those skilled in the art and are described in more detail in for example, *Remington: The Science and Practice of Pharmacy* ("Remington's Pharmaceutical Sciences") Gennaro A R ed. 20th edition, 2000: Williams & Wilkins PA, USA.

The route and regimen of administration will vary depending upon the stage or severity of the condition to be treated, and is to be determined by the skilled practitioner. For example, the polypeptide(s) according to the invention and compositions containing it can be used for preparing a pharmaceutical composition that can be administered in subcutaneous, intradermal, or topical or mucosal or intra-muscular form. All of these forms are well known to those of ordinary skill in the pharmaceutical arts.

Advantageously, suitable formulations of the present invention may e.g. be administered in a single dose, which may be repeated daily, weekly, or monthly.

Initial doses can be followed by booster doses, following immunization protocols standard in the art. The immunostimulatory effect of the compositions and methods of the instant invention can be further increased by combining any of the above-mentioned polypeptides, including their combination with delivery vehicles and/or with an immune response potentiating compound. Immune response potentiating compounds are classified as either adjuvants or cytokines. Adjuvants may enhance the immunological response by providing a reservoir of antigen (extracellularly or within macrophages), activating macrophages and stimulating specific sets of lymphocytes.

Each of the inventive polypeptides can be conjugated to a proteinous or non-proteinous delivery vehicle. Examples of such conjugations are described in Szaóo R. et al., (*Biochim Biophys Acta*. 2010 December; 1798(12):2209-16. Epub 2010 Jul. 24.) and in "Conjugation of haptens" (Lemus & Karol, *Methods Mol Med*. 138:167-82, 2008). It is preferred that the delivery vehicle itself has an immune effect, which means the delivery vehicle itself is immunogenic.

The delivery vehicle is selected from the group consisting of immunogenic peptides, immune stimulation nucleic acid sequences like GPC islands, limpet hemocyanin (KLH), tetanus toxoid (TT), cholera toxin subunit B (CTB), bacteria or bacterial ghosts, liposome, chitosome, virosomes, microspheres, dendritic cells, virus-like particles or their like.

In another embodiment, the present invention provides a vaccine composition further comprising a delivery vehicle as defined herein above. Preferably, the delivery vehicle is a virosome.

The antigenic polypeptides, compositions, or formulation thereof according to the present invention may be delivered via the delivery vehicles defined herein above, preferably by a virosome.

The prophylactic or therapeutic compositions of the present invention are for administration in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents. The preparations of the invention are administered in effective amounts. An effective amount is that amount of a pharmaceutical preparation that alone, or together with further doses, stimulates the desired response. Generally, doses of immunogens ranging from 0.01 µg/kilogram to 500 µg/kilogram body weight, depending upon the mode of administration, are considered effective. The preferred range is believed to be between 0.1 µg/kilogram and 10 µg/kilogram body weight. The absolute amount will depend upon a variety of factors, including the composition selected for administration, whether the administration is in single or multiple doses, and individual patient parameters including age, physical condition, size, weight, and the stage of the disease. These factors are well known to those of ordinary skill in the art and can be addressed with no more than routine experimentation.

The dosage regimen utilizing the compositions of the present invention is selected in accordance with a variety of factors, including for example species, age, weight, and medical condition of the patient, the stage and severity of the condition to be treated, and the particular compound thereof employed. A physician of ordinary skill can readily determine and prescribe the effective amount of the vaccine required to prevent, counter, or arrest the progress of an infectious disease. Optimal precision in achieving a concentration of a drug with the range that yields efficacy either without toxicity or with acceptable toxicity requires a regimen based on the kinetics of the drug's availability to target sites. This process involves a consideration of the distribution, equilibrium, and elimination of the drug, and is within the ability of the skilled practitioner.

In the uses of the present invention, the compounds herein described in detail can form the active ingredient and are typically administered in admixture with suitable pharmaceutical diluents or excipients suitably selected with respect to the intended form of administration, that is, oral tablets, capsules, elixirs, syrups, and the like, and consistent with conventional pharmaceutical practices. For instance, for administration in the form of a tablet or capsule, the active vaccine component can be combined with a non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethyl cellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, aga, bentonite, xanthan gum and the like.

For parenteral administration, sterile suspensions and solutions are desired. Isotonic preparations which generally contain suitable preservatives are employed when intravenous administration is desired. Intraesophageal preparations containing the active drug component can be admixed with a variety of carrier materials well known in the art, such as, for example, alcohols, aloe vera gel, allatoin, glycerine, vitamins A or E oils, mineral oil, PPG2 myristyl propionate, and the like, to form, for example, alcoholic solutions, topical cleansers, cleansing creams, gels, foams, and lotions, in cream or gel formulations especially suited for mucosal applications.

The antigenic polypeptides, compositions, or formulation thereof of the present invention may be coupled to a class of biodegradable polymers useful in achieving controlled release of a drug, for example, polylactic acid, polyepsilon caprolactone, polyhydroxy butyric acid, polyorthoesters, polyacetals, polydihyrdopyrans, polycyanoacrylates, and cross-linked or amphipathic block copolymers of hydrogels.

In the case the polypeptide according to the invention is used for preparing a pharmaceutical composition for treating an infectious disease, such as an infection caused by *A. baumannii*, the desired response is control of the infection and/or clearance of the antigenic polypeptide from the system. In the case of prophylaxis, the desired response is protective immunity to such polypeptide, as measured by immune responses upon exposure to the antigenic polypeptide. These desired responses can be monitored by diagnostic methods such as ELISA, immunoblot and the like [Raem A M. *Immunoassay*. 2007. P. Rauch [ed.] Spektrum Akademischer Verlag, Elsevier Gmbh].

The present invention provides an antigenic polypeptide consisting of an amino acid sequence depicted in any one of SEQ ID NOs: 2, 4, 6, 8, 10, 12, 14 and 16; or fragment, analog or functional derivative thereof, wherein said fragment, analog or functional derivative has immunostimulatory activity. Said antigenic polypeptides, fragments, analogs and functional derivatives thereof are defined in more detail herein above.

The antigenic polypeptide consisting of an amino acid sequence depicted in any one of SEQ ID NOs: 2, 4, 6, 8, 10, 12 14 and 16 that may comprises up to 50, 45, 40, 35, 30, 25, 20, 15, 10, preferably up to 5, more preferably up to 3 additional amino acids; or fragment, analog or functional derivative thereof, wherein said antigenic polypeptide, fragment, analog or functional derivative thereof has immunostimulatory activity.

Amino acids and amino acid residues described herein may be referred to according to the accepted one or three letter code referenced in text books well known to those of skill in the art, such as Stryer, *Biochemistry*, 4th Ed., Freeman and Co., New York, 1995 and Creighton, *Proteins*, 2nd Ed. Freeman and Co., New York, 1993.

As used herein, the terms "peptide" and "polypeptide" are used synonymously and in their broadest sense refer to a molecule of two or more amino acid residues, or amino acid analogs. The amino acid residues may be linked by peptide bonds, or alternatively by other bonds, e.g. ester, ether, etc. As used herein, the term "amino acid" or "amino acid residue" refers to natural and/or unnatural or synthetic amino acids, including both the D or L enantiomeric forms, and amino acid analogs.

Bacterial surface proteins play a fundamental role in the interaction between the bacterial cell and its environment. They are involved in adhesion to and invasion of host cells, in sensing the chemical and physical conditions of the external milieu and sending appropriate signals to the cytoplasmic compartment, in mounting defenses against host responses and in toxicity. Hence, surface proteins are potential targets of drugs aimed at preventing bacterial infections and diseases. Moreover, because surface proteins are likely to interact with the host immune system, they may become components of effective vaccines. Vaccines based on surface-exposed and secreted proteins are already commercially available for various infectious diseases; however a vaccine against *Acinetobacter* infections has not been developed yet due to a lack of availability of feasible targets.

Despite the biological relevance of bacterial surface proteins, their characterization is still incomplete. This is mostly owing to difficulties in defining the protein composition and topology on the bacterial surface.

To identify new vaccine candidates and targets for antibodies, three different methods were used. Each one selected for particular requirements for a vaccine and antibody target candidate.

The first method—"Shedome analysis"—uses proteolytic enzymes to "shed" the bacterial surface. The peptides generated are separated from the whole cells, identified by mass spectrometry and subsequently assigned to proteins using public available databases (Rodriguez-Ortega M J et al., *Nature Biotechnology*, 24, 191-197, 2006).

To discriminate between contaminants, such as intracellular proteins of highly abundant proteins like ribosomal proteins, and putative membrane targets, the identified proteins were analyzed for their localization within the bacteria using public available online tools. See, for example K. Imai et al., *Bioinformation* 2(9), 417-421 (2008). Proteins that were assigned as extracellular or outer membrane protein were selected for further analysis. In addition, proteins that were annotated by the UniprotKB Database as a homologue to known extracellular or outer membrane proteins were selected as well.

The concept of the second method—"Comparative proteomics"—is to focus on targets whose expression is experimentally confirmed in various *Acinetobacter* strains. Proteomics, the study of the proteome, has largely been practiced through the separation of proteins by two dimensional gel electrophoresis. In the first dimension, the proteins are separated by isoelectric focusing, which resolves proteins on the basis of charge. In the second dimension, proteins are separated by molecular weight using SDS-PAGE. The gel is dyed with Coomassie Brilliant Blue or silver to visualize the proteins. Spots on the gel are proteins that have migrated to specific locations.

The mass spectrometer has augmented proteomics. Peptide mass fingerprinting identifies a protein by cleaving it into short peptides and then deduces the protein's identity by matching the observed peptide masses against a sequence database.

According to the invention the whole proteome of protein preparation enriched for outer membrane proteins was determined by mass spectrometry of five different *A. baumannii* strains. The five *A. baumannii* strains ATCC19606, BMBF65, SDF, ACICU, AYE were selected due to their different sources of isolation. ATCC19606 is an old *A. baumannii* isolate from 1948 (Hugh R., Reese R., *Int. J. Syst. Bacteriol.* 17: 245-254, 1967), used by many research laboratories as a reference strain. AYE is an *A. baumannii* strain that was epidemic in France during 2001 (Vallenet et al., *PLoS One* 3:E1805-E1805 (2008)). ACICU was isolated during an outbreak in Rome, Italy 2005 (Iacono M., et al., *Antimicrob. Agents Chemother.* 52:2616-2625 (2008)).

BMBF-65 was isolated from a patient in Singapore in 2004. SDF is the only non-clinical isolate of *A. baumannii* that was isolated from body lice collected in 1997 in Marseille, France (Vallenet et al., *PLoS One* 3:E1805-E1805 (2008)).

To enrich for putative targets that are present on the extracellular surface, protein preparations were enriched for outer membrane proteins prior to MS analysis according to their hydrophilic and hydrophobic properties. The peptides identified by mass spectrometry were assigned to proteins using publicly available databases and selected according to IT-predictions and literature searches.

The third approach refers to identification of targets that are recognized by antibodies present in sera of convalescent *A. baumannii* patients. Accordingly, protein preparations enriched for outer membrane (OM) proteins, were separated by 2-dimensional gel electrophoresis (2DE). The 2DE constituted of an isoelectric focusing (IEF) followed by SDS-polyacrylamide gel electrophoresis (PAGE) step to resolve the OM proteins. Proteins recognized by patient sera were determined by immunoblot analysis. To increase chances to identify proteins that are expressed by various different strains, immunoblots of at least two *A. baumannii* strains were compared and proteins present in all strains analyzed were selected for protein identification by MS-analysis. The proteins were individually characterized and selected according to IT-predictions and literature searches. Proteins that were identified as *A. baumannii* protein and predicted to be or annotated as an outer membrane protein were chosen as putative targets. In case prior art predicted homologues of such targets to be down-regulated or absent in antibiotic resistant *A. baumannii* strains, these targets were excluded from further analysis.

According to an aspect of the invention there is provided at least one polypeptide identified by the approaches according to the invention.

In a preferred embodiment of the invention, said polypeptide is associated with infective pathogenicity of an organism, preferably of *A. baumannii*, according to any previous aspect or embodiment of the invention.

More preferably said polypeptide is at least one of the amino acid sequences SEQ ID NOs: 2, 4, 6, 8, 10, 12, 14 and 16 or fragment, analog or functional derivative thereof.

The targets that were selected for vaccine development fulfill at least two of the following three requirements:

1. The targets are accessible to large molecules (approach 1: surface proteins identified by Shedome analysis).
2. The targets are expressed by many *A. baumannii* strains preferably by strains which represent important clinical isolates (approach 2: Comparative Proteomics).
3. The targets induce an immune response and are expressed in patients during infection (approach 3: specific target identification).

The numbers of potential targets meeting the requirements of each selection step are specified in Table 3. The potential targets selected by this method are designated in the final row.

Table 3 below shows the selection process for target identification by different approaches. Each approach focuses on a particular requirement described above. Bold numbers indicate number of proteins that meet the requirements of the corresponding selection step. The details of the selection process are given in Example 1.2.

TABLE 3

| | Shedome Analyis | Comparative Proteomics | Specific Target Identification |
|---|---|---|---|
| Total numbers of potential targets | | >3500 annotated genes in *A. baumannii* genomes | |
| Experimental selection | Proteome determination of tryptic digest of live *A. baumannii* 163 | Proteome determination of outer membrane preparations of 5 different *A. baumannii* strains 1552 | Comparison of 2DE Immunoblots of outer membrane preparations of 2 different *A. baumannii* strains using patient sera. 7 |
| 1st in silico selection Proteins identified by 5 strains | N/A | 363 | N/A |
| 2nd in silico selection IT prediction: Extracellular proteins Outer membrane proteins with surface located epitopes. | 7 | 30 | 5 |
| 3rd in silico selection If available, data from literature IT prediction: high prevalence of genes high amino acid sequence conservation | 3 | 6 | 4 |
| Selected targets | FimA, CsuAB, OmpA | AB023, AB024, AB025, AB030, AB031, OmpA | AB023, AB024, AB025, OmpA |

IT-Prediction was performed as follows: Protein homology detection and structure prediction by HMM-HMM-comparison was performed using online software tool HHpred Soding J., p. 951-960, (2005) using the HMM database pdb70.sub.—3Sep11, HHblits as MSA generation method with maximal 3 iterations and local Alignment mode.

Table 4 shows the structural homologues of SEQ ID NOs: 2, 4, 6, 8, 10, 12, 14 and 16 as determined by databank analysis.

TABLE 4

| Antigen SEQ ID NO: | Protein ID[1] | Query HMM[2] | Template HMM[2] | Probability[3] [%] | E-value[4] | P-value[5] | Template Description[1] |
|---|---|---|---|---|---|---|---|
| AB023 SEQ ID NO: 2 | 2wjr 2o4v | 346-417 52-417 | 29-95 32-411 | 93.0 92.4 | 0.25 6.6 | 9.9E–06 0.00026 | NanC - Porin (*E. coli*) OprP - Porin (*P. aeruginosa*) |
| AB024 SEQ ID NO: 4 | 2zfg 2fgq | 97-435 100-435 | 7-340 3-332 | 99.7 99.5 | 4E–12 9E–11 | 1.6E–16 3.5E–15 | OmpF - Porin (*E. coli*) Omp32 - Porin (*D. acidovorans*) |

TABLE 4-continued

| Antigen SEQ ID NO: | Protein ID[1] | Query HMM[2] | Template HMM[2] | Probability[3] [%] | E-value[4] | P-value[5] | Template Description[1] |
|---|---|---|---|---|---|---|---|
| AB025 SEQ ID NO: 6 | 2o4v 2qtk | 116-439 144-474 | 60-411 88-389 | 96.3 90.4 | 0.79 14 | 3.1E−05 0.00054 | OprP - Porin (P. aeruginosa) Opdk - Porin (P. aeruginosa) |
| AB030 SEQ ID NO: 8 | 2qdz 3efc | 269-906 241-543 | 10-554 79-375 | 100.0 100.0 | 1.4E−45 2.5E−31 | 0 9.9E−36 | FahC - Omp85 (P. pertussis) YaeT - Omp85 (E. coli) |
| AB031 SEQ ID NO: 10 | 1ek9 1yc9 | 42-485 42-486 | 2-409 34-440 | 100.0 100.0 | 4.2E−45 1.7E−44 | 0 0 | TolC - channel (E. coli) Vcec - channel (V. cholerae) |
| FimA SEQ ID NO: 12 | 2jmr 2jty | 21-177 16-177 | 2-155 1-159 | 100.0 99.9 | 4.2E−30 1.1E−27 | 1.6E−34 4.3E−32 | FimF - type I Pili (E. coli) FimA - type I Pili (UP-E. coli) |
| CsuAB SEQ ID NO: 14 | 3me0 1ze3 | 40-180 38-180 | 8-127 1-121 | 98.3 97.8 | 1.4E−05 0.00043 | 5.6E−10 1.7E−08 | PapD - type I Pili (E. coli) FimD - type I Pili (E. coli) |
| OmpA SEQ ID NO: 16 | 3nb3 2kgw | 1-345 208-335 | 1-344 1-128 | 100.0 100.0 | 0 1.6E−28 | 0 6.2E−33 | OmpA - (E. coli) Ompatb - (M. tuberculosis) |

[1]Protein ID of structural homologue (http://www.ncbi.nlm.nih.qov/Wang Y, et al., *Nucleic Acids Res.* 2007 Jan; 35 (Database issue): D298-300.) including a short description (Name, function, Species) in the last column.
[2]HMM: Hidden Markov Model. Amino acid sequences producing homology between query and template. The number indicate the positions of amino acid sequence in the query (SEQ ID NOs: 2, 4, 6, 8, 10, 12, 14, 16) or template (Protein ID) sequence that produces homology.
[3]Probability: "Probability of template to be a true positive."
[4]E-value: "Expect-value. E-value and P-value are calculated without taking the secondary structure into account. The E-value gives the average number of false positives ('wrong hits') with a score better than the one for the template when scanning the database. It is a measure of reliability: E-values near 0 signify a very reliable hit, an E-value of 10 means about 10 wrong hits are expected to be found in the database with a score at least this good."
[5]P-Value: "The P-value is the E-value divided by the number of sequences in the database. It is the probability that in a pairwise comparison a wrong hit will score at least this good."

Any of the polypeptides with SEQ ID NOs: 2, 4, 6, 8, 10, 12, 14, 16 has immunostimulatory activity.

Table 5 refers to expression of the antigenic polypeptides of the invention in clinical isolates of *A. baumannii*. A total of 36 clinical strains isolated from blood, urine, cerebrospinal fluid, pus and tracheal aspirates of patients admitted to the hospital—were included in the study. Such clinical isolates (Example 1.1.4) were used to isolate bacterial lysates or precipitated culture supernatant which after gel electrophoresis were tested by immunoblot analysis. For the detection of each antigenic polypeptide the corresponding rabbit antiserum was used (Example 5).

Table 5 shows the percentages and the actual number of clinical isolates of *A. baumannii* wherein any of the individual antigenic polypeptides identified (target) was shown to be present or absent by immunoblot analysis in preparations from bacterial cell pellets.

TABLE 5

| Target | Number of clinical isolates | Target detected in bacterial cell pellet of clinical isolates | |
|---|---|---|---|
| | | present | absent |
| AB023 | 20 | 100% (20) | 0% (0) |
| AB024 | 20 | 100% (20) | 0% (0) |
| AB025 | 21 | 100% (21) | 0% (0) |
| AB030 | 21 | 100% (21) | 0% (0) |
| AB031 | 24 | 100% (24) | 0% (0) |
| FimA | 36 | 44% (16) | 56% (20) |
| CsuAB* | 36 | 81% (29) | 19% (7) |
| OmpA | 32 | 100% (32) | 0% (0) |

*Expression levels of csuAB varied between different strains. 19% showed no, 24% weak and 62% medium to strong expression.

FIG. 2 shows the polypeptides of the invention having immunostimulatory activity. Rabbits were immunized with the polypeptides. The sera of these rabbits proved positive for polypeptide specific antibodies.

According to a further aspect of the invention there is provided a nucleic acid molecule encoding said antigenic polypeptide(s).

In a further aspect, the present invention relates to a vector comprising the nucleic acid molecule according to the invention. Moreover, the present invention relates to a host cell comprising said vector.

There is a significant amount of published literature with respect to expression vector construction and production and purification of recombinantly expressed polypeptides (Sambrook et al (1989) *Molecular Cloning: A Laboratory Manual*, Cold Spring Harbour Laboratory, Cold Spring Harbour, NY and references therein; DNA Cloning: F M Ausubel et al, *Current Protocols in Molecular Biology*, John Wiley & Sons, Inc. (1994).

Further, the present invention provides host cells comprising the vector and/or the nucleic acid suitable for the expression of the vector. In the art, numerous prokaryotic and eukaryotic expression systems are known wherein eukaryotic host cells such as yeast cells, insect cells, plant cells and mammalian cells, such as HEK293-cells, PerC6-cells, CHO-cells, COS-cells or HELA-cells and derivatives thereof are preferred. Particularly preferred are human production cell lines. It is preferred that the transfected host cells secrete the produced antibody into the culture medium. If intracellular expression is achieved, then renaturation is performed in accordance with standard procedures such as described by Benetti P. H. et al., *Protein Expr. Purif.* 13(3):283-290 (1998).

Production of the polypeptides according to any previous aspect or embodiment of the invention comprise: (i) providing a cell transformed/transfected with a vector according to the invention; (ii) growing said cell in conditions conducive to the manufacture of said polypeptides; and (iii) purifying said polypeptide from said cell, or its growth environment.

In a preferred embodiment of the invention said cell is a prokaryotic cell.

Alternatively said cell is a eukaryotic cell selected from: fungal, yeast, insect, algae, mammalian, plant.

The present invention provides an antibody or an antigen-binding fragment thereof that specifically binds the polypeptide as defined above, wherein said antibody or antigen-binding fragment thereof is capable of neutralizing *Acinetobacter baumanii*.

The term "antigen-binding fragment" means any fragment of the antibody capable of binding to any of the polypeptides defined by the claims. The fragment has a length of at least 10, preferably 20, more preferably 50 amino acids. It is preferred that the fragment comprises the binding region of the antibody. It is preferred that the fragment is a Fab or F(ab')2 fragment or a mixture thereof.

An antibody mediated "effector function" can be the inhibition of a specific function of the target antigen, such as the neutralization of an effect of a secreted bacterial toxin, thereby preventing the detrimental effects of the toxin on protein interactions, enzymatic function, cellular functions, cell integrity, tissue structures and other biological process. Another antibody mediated effector function can be the inactivation of the function of a specific bacterial protein, such as a porin and other proteins or structures on the cell surface, thereby affecting the normal bacterial life cycle. Another antibody mediated effector function can consist of activation of immunological processes, such as activation of complement cascade, induction of cytokine and chemokine production, activation of cellular components of the immune system and other immunological reactions leading to the destruction and removal of bacterial cells.

In a preferred embodiment of the invention said antibody is a polyclonal or a monoclonal antibody, wherein said antibodies are specific to said polypeptide.

In order to produce polyclonal antibodies in a host, such as a mouse or rabbit, the host is immunized with the antigenic polypeptide or fragment or analog or functional derivative thereof, optionally with an adjuvant. Antibodies to the antigenic polypeptide are subsequently collected from the sera of the host. The polyclonal antibody can be affinity purified against the antigen rendering it specific. Such polyclonal antibody preparations can also be derived from human donors, either vaccinated, convalescent or normal healthy donors, by plasma fractionating to generate polyclonal immunoglobulin fractions and further enriched against the antigen rendering it specific.

Such polyclonal antibodies were raised by immunizing rabbits with the antigenic polypeptides AB023, AB024, AB025, AB030, AB031L, ABFimA, ABCsuAB and ABOmpA. Four to eight weeks after immunization blood samples were collected and sera tested for presence of polypeptide specific antibodies; see FIGS. 3 and 4.

Polyclonal antibodies recognize many different epitopes. In contrast monoclonal antibodies are specific for a single epitope. Further details regarding antibody structure and their various functions can be found in, "*Using Antibodies: A laboratory manual*", Cold Spring Harbour Laboratory Press, 1999.

In a further preferred embodiment, the antibody of the invention is a monoclonal antibody or an antigen-binding fragment thereof which is capable of inducing an effector function towards *Acinetobacter* baumanii. Most preferably, the monoclonal antibody of the invention or an antigen-binding fragment thereof specifically binds the epitope consensus motif PVDFTVAI shown in SEQ ID NO: 36.

The term "epitope" includes any determinant, preferably a polypeptide determinant, capable of specific binding to an immunoglobulin. In certain embodiments, epitope determinants include chemically active surface groupings of molecules such as amino acids, sugar side chains, phosphoryl, or sulfonyl groups, and, in certain embodiments, may have specific three-dimensional structural characteristics, and/or specific charge characteristics. An epitope is a region of an antigen that is bound by an antibody. Monoclonal antibodies usually bind to these consensus motifs, which are mostly 5 amino acids in lengths, or 6, 7 or 8 amino acids in length. In a preferred embodiment the antibody provided by the invention is monoclonal and specifically binds to an epitope consensus motif of 8 amino acids in length. In certain embodiments, an antibody is said to specifically bind an antigen when it preferentially recognizes its target antigen in a complex mixture of proteins and/or macromolecules. In preferred embodiments, an antibody is said to specifically bind an antigen when the dissociation constant is less than or equal to about 10 nM, more preferably when the dissociation constant is less than or equal to about 100 pM, or when the dissociation constant is less than or equal to about 10 pM.

In a further embodiment the antibody of the invention is human. The term "human" as used herein encompasses any partially or fully human antibody independent of the source from which the antibody is obtained. The production of a human monoclonal antibody by a hybridoma is preferred. For example, the human monoclonal antibody consisting of human amino acid sequence can be obtained from a hybridoma wherein the B-cell is a human B-cell. The monoclonal antibody may also be obtained by genetic engineering.

"Humanized" antibodies are also contemplated, as are chimeric antibodies from mouse, rat, or other species bearing human constant and/or variable region domains, bispecific antibodies, recombinant and engineered antibodies and fragments thereof. "Humanizing" techniques typically involve the use of recombinant DNA technology to manipulate DNA sequences encoding the polypeptide chains of the antibody molecule. Early methods for humanizing monoclonal antibodies (MAbs) involved production of chimeric antibodies in which an antigen binding site comprising the complete variable domains of one antibody is linked to constant domains derived from another antibody. Methods for carrying out such chimerization procedures are described in EP0120694 (Celltech Limited), EP0125023 (Genentech Inc. and City of Hope), EP-A-0 171496 (Rev. Dev. Corp. Japan), EP-A-0 173 494 (Stanford University), and WO 86/01 533 (Celltech Limited). Generally these applications disclose processes for preparing an antibody molecule having the variable domains from a mouse MAb and the constant domains from a human immunoglobulin. Alternative approaches are described in EP-A 023 9400 (Winter), in which the complementary determining regions (CDRs) of a mouse MAb have been grafted onto the framework regions of the variable domains of a human immunoglobulin by site directed mutagenesis using long oligonucleotides. See U.S. Pat. No. 7,262,050 for an example of such methods.

Humanized antibodies can also be obtained from transgenic animals. For example, transgenic, mutant mice that are capable of producing a full repertoire of human antibodies, in response to immunization, have been described (see, e.g., Jakobovits et al., *Proc. Natl. Acad. Sci. USA*, 90:2551 (1993); Brüggemann et al., *Year in Immuno.*, 7:33 (1993), Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge.

The human amino acid sequence of the human monoclonal antibody prevents the occurrence of undesired adverse effects such as rejection reactions or anaphylactic shock.

According to a further preferred embodiment, the antibody according to the present invention is N-terminally, internally and/or C-terminally modified. The modification is selected from at least one of the di-, oligo-, or polymerization of the monomeric form e.g. by cross-linking using dicyclohexylcarbodiimide. The thus produced di-, oligo-, or polymers can be separated from each other by gel filtration. Further modifications include side chain modifications, e.g. modifications of $\epsilon$-amino-lysine residues, or amino and carboxy-terminal modifications, respectively. Further modifications include post-translational modifications, e.g. glycosylation and/or partial or complete deglycosylation of the protein, and disufide bond formation. The antibody may also be conjugated to a label, such as an enzymatic, fluorescent or radioactive label.

The antibody according to the present invention is produced from a human B cell or a hybridoma obtained by fusion of said human B cell with a myeloma or heteromyeloma cell.

The present invention further provides a hybridoma capable of producing a monoclonal antibody. The production of monoclonal antibodies using hybridoma cells is well-known in the art. The methods used to produce monoclonal antibodies are disclosed by Kohler and Milstein in *Nature* 256, 495-497 (1975) and also by Donillard and Hoffman, "Basic Facts about Hybridomas" in *Compendium of Immunology* V. II ed. by Schwartz, 1981.

Alternatively to the hybridoma technology the human monoclonal antibody may also be obtained by recombinant expression of nucleic acids encoding the light and heavy chain of the antibody.

Accordingly, the present invention provides a nucleic acid encoding the light and the heavy chain of the antibody, a vector comprising such antibodies and a host cell comprising such vector and/or such nucleic acids.

Preferably, a vector according to the invention is selected from adenoviruses, vaccinia viruses, baculoviruses, SV 40 viruses, retroviruses, plant viruses or bacteriophages such as lambda derivatives or M13 comprises at least one nucleic acid encoding the light chain and at least one nucleic acid encoding the heavy chain. A host cell transformed with said vector and cultured under conditions suitable for recombinant expression of the encoded antibody chain is capable of assembling the human monoclonal antibody such that a 3-dimensional structure is generated which is equivalent to the 3-dimensional structure of a human monoclonal antibody produced by a human B-cell. If the light chain is produced separately from the heavy chain, then both chains may be purified and subsequently be assembled to produce a human monoclonal antibody having essentially the 3-dimensional structure of a human monoclonal antibody as produced by a human B-cell.

In addition, a method is provided for producing the antibody as defined above comprising culturing a hybridoma under conditions allowing for secretion of an antibody, and optionally purifying the antibody from the culture supernatant.

In addition, pharmaceutical compositions comprising the antigenic polypeptide as defined above or the antibody as defined above are provided.

The pharmaceutical composition may further comprise pharmaceutically acceptable ingredients known in the art.

Preferably, the pharmaceutical compositions are applied for the treatment of diseases caused by *A. baumannii* in infections such as blood-stream infection, pneumonia, chronic bronchitis, local infections including wound infections and invasive infections of joints, mainly in immunocompromised patients and/or in patients with compromised respiratory function. The pharmaceutical compositions are further intended for but not limited to the prophylaxis and/or treatment of hospital-acquired (nosocomial) infections. Since the main victims of *A. baumannii* infections are intubated patients, burn victims, patients in surgical and/or medical intensive care units, cancer and AIDS patients, immunocompromised patients, immunosuppressed patients, diabetic patients, military personal, combat personal and associated support personal, as well as intravenous drug abusers, the pharmaceutical compositions are in particular intended for prophylaxis and/or treatment of diseases caused by *A. baumannii* in said group of patients.

The pharmaceutical composition may further comprise antibiotic drugs.

The pharmaceutical compositions comprise the antigenic polypeptide or the antibody in a concentration range of 0.1-30 mg/kg body weight.

The pharmaceutical compositions may be administered in any known manner such as intravenous, intra-muscular, intra-dermal, subcutaneous, intra-peritoneal, topical, intra-nasal administration, or as inhalation spray.

A further aspect of the invention refers to a diagnostic composition comprising the antigenic polypeptide or the antibody as defined above for detecting a bacterial infection in a patient. Detection of a bacterial infection, in particular a bacterial infection caused by *A. baumannii* according to the invention, may be performed on isolated bacterial DNA, or directly from clinical samples like sputum, bronchoalveolar lavage or tracheal aspiration, usually after dilution in ultrapure $H_2O$. Preferred are samples directly obtained from a lung lavage of a human such as a human patient with a pulmonary disorder. Clinical samples might also include bodily materials such as blood, blood sera, urine, tissues and the like. Typically the samples may be taken from wound, burn, lung, and urinary tract infections of humans or mammals. Antigenic polypeptides of the invention may be used to check for antibodies in blood sera. Antibodies are suitable for detection of the antigenic polypeptide (targets) e.g. in a clinical sample. The high value as a diagnostic tool of the antigenic polypeptides or the antibody specific thereto is demonstrated in Table 1 and FIG. 3.

The present invention provides a polyclonal or monoclonal antibody for use in the treatment and/or prevention of a bacterial infection in a mammal.

Preferably the mammal is human. The antibody is preferably used for treatment and or prevention wherein the bacterial infection is caused by *A. baumannii*, most preferably this infection is hospital acquired.

Disease areas that currently are especially amenable to antibody-based treatments include cancer, immune dysregulation, and infection. Depending upon the disease and the biology of the target, antibodies used for treatment—therapeutic antibodies—can have different mechanisms of action. A therapeutic monoclonal antibody may bind and neutralize the normal function of a target. For example, a monoclonal antibody that blocks the activity of the protein needed for the survival of a cancer cell causes the cell's death. Another therapeutic monoclonal antibody may bind and activate the normal function of a target. For example, a monoclonal antibody can bind to a protein on a cell and trigger an apoptosis signal. Finally, if a monoclonal antibody binds to a target expressed only on diseased tissue, conjugation of a toxic payload (effective agent), such as a chemotherapeutic or radioactive agent, to the monoclonal antibody can create a guided missile for specific delivery of the toxic payload to the diseased tissue, reducing harm to healthy tissue.

Prophylactic antibodies are guarding from or preventing the spread or occurrence of disease or infection An antibody defined by its structure/sequence has potentially prophylactic and therapeutic function depending on the time of administration.

Further, the present invention provides a polypeptide for use in the treatment and/or prevention of a bacterial infection in a mammal encoded by a nucleic acid molecule comprising a polynucleotide selected from the group consisting of:
a) a polynucleotide having the nucleic acid sequence depicted in any one of SEQ ID NOs: 1, 3, 5, 7, 9, 11, 13 and 15;
b) a polynucleotide encoding a fragment, analog or functional derivative of a polypeptide encoded by the polynucleotide of (a), wherein said fragment, analog or functional derivative has immunostimulatory activity;
c) a polynucleotide encoding a polypeptide having an amino acid sequence that is at least 80% identical to the amino acid sequence depicted in any one of SEQ ID NOs: 2, 4, 6, 8, 10, 12, 14 and 16 and having immunostimulatory activity;
d) a polynucleotide which is at least 80% identical to the polynucleotide of (a), and which encodes a polypeptide having immunostimulatory activity;
e) a polynucleotide which hybridizes under stringent conditions to the polynucleotide of any one of (a) to (d); and
f) a polynucleotide that is the complement of the full length of a polynucleotide of any of (a) to (d).

Preferably the polypeptide is for use in a mammal. More preferably the polypeptide is for use in treatment and/or prevention of a bacterial infection wherein the infection is caused by *Acinetobacter baumanii*; most preferably the antigenic polypeptide of the invention is for use in treatment and/or prevention of a bacterial infection, wherein the infection is hospital-acquired.

The invention is further illustrated by reference to specific embodiments described in the Examples and Figures presented below.

EXAMPLES

Example 1

Identification of Targets (Antigenic Polypeptides)

1.1 Materials

Unless not otherwise specified, chemical defined reagents were analytical grade and derived from qualified suppliers, mainly Sigma-Aldrich (Buchs, Switzerland).

1.1.1 Bacterial Media

Luria-Bertani broth (LB) consisted of 1% (w/v) tryptone (Fluka/Sigma-Aldrich, Switzerland), 0.5% (w/v) yeast extract (Fluka,), 1% (w/v) NaCl. Immediately after preparation the LB was autoclaved (121° C. for 20 minutes) and kept sterile at room temperature for up to 3 months. For LB-agar (LBA) plates, 0.75% (w/v) agar (Fluke), was added to LB before the media was autoclaved. Afterwards the hot LBA was distributed into plastic petri dishes (Sterilin, Cambridge, UK) before the media cooled below 50° C. Once the LBA within the petri dishes solified the LBA plates were kept at 4° C. for up to 3 months. BHI-Agar plates were ordered at Becton Dickinson (Heidelberg, Germany).

1.1.2 Bacterial Strains

Several bacterial strains were used. The most relevant bacterial strains used to generate the data and the experimental procedures are listed in Table 5. In addition, several clinical isolates of *A. baumannii*, were received from Prof. Seifert (Institute of Medical Microbiology and Hygiene, University of Cologne, Germany), Prof. Dijkshoorn (Leiden University Medical Centre, Leiden, NL), Prof. Nordmann, (Centre Hospitalier Universitaire der Bicêtre, Service de Bactériologie-Virologie, Le Kremlin-Bicêtre cedex, France).

TABLE 6

| Strain | Species | Reference | Source |
| --- | --- | --- | --- |
| ATCC19606 | A. baumannii | Hugh R., Reese R. Int. J. Syst. Bacteriol. 17: 245-254, 1967 | Prof. Luis Actis, Miami University, Department of Microbiology, 40 Pearson Hall Oxford, Ohio 45056 |
| OmpA KO | A. baumannii | Gaddy, J. A. et al., Infection and Immunity 77 (8), S. 3150-3160. (2009) | |
| CsuE KO | A. baumannii | Tomares, Microbiology, 154, 3398 (2008) | |
| AYE | A. baumannii | Vallenet et al., PLoS One 3: E1805-E1805 (2008)) | Profs. D. Raoult, M. Drancourt URMITE-CNRS UMR6236, Marseille France |
| SDF | A. baumannii | | |
| ACICU | A. baumannii | Iacono M., et al., Antimicrob. Agents Chemother. 52: 2616-2625 (2008). | Prof. Alessandra Carattoli Department for Infectious, Parasitic and Immune-Mediated Diseases, Istituto Superiore di Sanità, Viale Regina Elena 299, 00161 Rome-Italy |
| Ruh134 | A. baumannii | Clinical isolate Rotterdam, NL, 1982 | Prof. L. Dijkshoorn, Leiden University Medical Centre, Leiden, NL |
| Ruh875 | A. baumannii | Clinical isolate Dordrecht, NL, 1984 | |

TABLE 6-continued

| Strain | Species | Reference | Source |
|---|---|---|---|
| Berlin-95 | A. baumannii | Clinical isolate Berlin, GE, 2006 | Prof. Seifert, Institute of Medical Microbiology and Hygiene, University of Cologne, Germany |
| BMBF65 | A. baumannii | Clinical isolate Singapore, 2004 | |
| AB-M | A. baumannii | Eveillard, et al., | Prof. Marie-Laure Joly Guillou, UFR Sciences |
| AB-NM | A. baumannii | Journal of Infection 60 | pharmaceutiques et ingénierie de la santé 16, |
| SAN | A. baumannii | (2), 154-161, 2010 | Bd Daviers, 49045, Angers, France |
| PA O11 | P. aeruginosa | ATCC 33358, Liu PV, et al. Int. J. Syst. Bacteriol. 33: 256-264, 1983 | |
| DH5alfa | E. coli | | Invitrogen |
| BL-21(DE3) | E. coli | | Novagen |

NCBI: National Center for Biotechnology Information; ATCC: American Tissue Culture Collection, Virginia, USA1.1.3 A. baumannii reference genomes Several published genomes were used for identification and characterization of identified targets as summarized in Table 7.

TABLE 7

Genome Sequences

| A. baumannii Genome | References sequence |
|---|---|
| ATCC19606 | [1]NZ_ACQB00000000 |
| AYE | [1]NC_010410 |
| ACICU | [1]NC_010611 |
| SDF | [1]NC_010400 |
| AB307-0294 | [1]NC_011595 |
| 6014059 | [1]NZ_ACYS00000000 |
| 6013113 | [1]NZ_ACYR00000000 |
| 6013150 | [1]NZ_ACYQ00000000 |
| AB0057 | [1]NC_011586 |
| ATCC 17978 | [1]NC_009085 |
| AB059 | [1]NZ_ADHB00000000 |
| AB058 | [1]NZ_ADHA00000000 |
| AB056 | [1]NZ_ADGZ00000000 |
| AB900 | [1]NZ_ABXK00000000 |

[1]http://www.ncbi.nlm.nih.gov/genome

1.1.3 Patient Sera

Patient sera were collected in various hospitals. Sera form 20 patients were described in previous studies (Pantophlet, R. et al. *Clin. Diagn. Lab. Immunol.* 7 (2), 293-295, (2000)) and were received from Prof. Seifert (Institute of Medical Microbiology and Hygiene, University of Cologne, Germany).

Further 57 patient sera were collected from hospitals in Athens (Greece), Sevilla (Spain), Pittsburgh (PE, USA) and Jerusalem (Israel). The following inclusion criteria were applied:
1. the patients have a confirmed *A. baumannii* bloodstream infections, pneumonia or severe wound infection,
2. the patient health status allows for blood collection and
3. that the patient is an adult less than 85 years of age.
Patients with confirmed viral infection (e.g. Hepatitis A, B or C, HIV), anemia or a suppressed immune system were excluded. All patients signed an informed consent. Sera from healthy donors were collected from the Swiss-Red-Cross blood donation centre in Bern (Switzerland).

1.2 Approaches to Identify Suitable Targets

1.2.1 "Shedome" Analysis

The concept of this method is to identify polypeptides on the *Acinetobacter* membrane as they are accessible to large molecules such as antibodies. Thus live *A. baumannii* bacteria were shed with trypsin, a 23 kDa protease, and analyzed by mass spectrometry (MS). The identified peptides were assigned to proteins using public available databases. It can be expected that, besides contaminants of highly abundant proteins and lysed bacteria, the digest contains peptides derived from proteins present on the extracellular side of the bacterial membrane.

1.2.1.1 Preparation of Bacterial Cultures

*A. baumannii* strain ATCC19606 was streaked onto an LBA plate and incubated overnight (16 h-24 h) at 37° C. The LBA plate with visible bacterial colonies was kept at 4° C. for up to 1 month. As starting culture, 25 ml LB were inoculated using *A. baumannii* colonies from the LBA plate and incubated overnight at 37° C. shaking at 200 rotations per minute (rpm). The optical density at 600 nm ($OD_{600}$) of the overnight culture was measured. LB (0.4 l) was inoculated with overnight culture at a starting $OD_{600}$ of 0.05 and incubated at 37° C. shaking at 200 rpm for 3.5 h until an $OD_{600}$ of 0.68 was reached.

1.2.1.2 Trypsin Digests of Live Bacteria

Rodriguez-Ortega et al. (Nature Biotechnology, 24, 191-197, 2006) previously described a method for tryptic digest of gram positive bacteria, which was used to establish the following protocol for the gram negative *A. baumannii*. The bacteria were centrifuged at 3500 g for 10 minutes at 4° C. The pellet was washed 3 times in 40 ml PBS (8% (w/v) NaCl, 2% (w/v) KCl, 1.1% (w/v) $Na_2HPO_4$, 0.2% (w/v) $KH_2PO_4$, pH=7.4) at 4° C. by resuspension and centrifugation. The pellet was washed once in 2 ml sucrose buffer (PBS containing 40% (w/v) sucrose, 5 mM DTT (Dithiothreitol) and finally the pellet was resuspended in 2 ml sucrose buffer containing 20 µg sequencing grade trypsin (Promega, V5113). The suspension was incubated for 30 minutes at 37° C. and then centrifuged for 10 minutes at 3500 rcf at 4° C. The supernatant was removed and centrifuged again for 5 minutes at 14000 rcf at 4° C. Again the supernatant was removed and filtered through a sterile filter for syringes (0.2 µm, Nalgene #194-2520). To 0.75 ml filtrate 0.75 µl formic acid were added, mixed and stored at −70° C. until analyzed by MS.

1.2.1.3 MS-Analysis of Tryptic Digest

Peptides were identified by mass spectrometry (nano LC-MS/MS with data-dependent collision induced fragmentation) at the Department of Clinical Research, University of Berne, Switzerland by the group of Dr. Manfred Heller. The UniprotKB Database (The UniProt Consortium, *Nucleic Acids Res.* 39: D214-D219, 2011), without entries from Firmicutes and *E. coli*, was used to assign peptides to proteins.

Briefly, a volume of 3 µl or 6 µl was loaded onto a pre-column (Magic C18, 5 µm, 300 Å, 0.15 mm i.d.×30 mm length) at a flow rate of ~5 µl/min with solvent A (0.1% formic acid in water/acetonitrile 98:2). After loading, peptides were eluted in backflush mode onto the analytical nano-column (Magic C18, 5 µm, 100 Å, 0.075 mm i.d.×75 mm length) using an acetonitrile gradient of 5% to 40% solvent B (0.1% formic acid in water/acetonitrile 4.9:95) in 60 min at a flow rate of ~400 nl/min. The column effluent was directly coupled to an LTQ-orbitrap XL mass spectrometer (Thermo Fisher Scientific, MA, USA,) via a nanospray ESI source operated at 1.700 kV. Data acquisition was made in data dependent mode with precursor ion scans recorded in the Fourier transform detector (FT) with resolution of 60'000 (@ m/z=400) parallel to five fragment spectra (CID) of the most intense precursor ions in the linear iontrap. CID mode settings were: Wideband activation on; precursor ion selection between m/z range 360-1400; intensity threshold at 500; precursors excluded for 15 sec. CID spectra interpretation was performed with PHENYX on a local, dual quad core processor server run under Linux using UniprotKB SwissProt and TrEMBL databases. Allowed, variable modifications were: Met oxidation (limited to 2), Asn/Gln deamidation (2), and pyrrolidone carboxylic acid on N-terminal Glu (1). Parent and fragment mass tolerances were set to 20 ppm and 0.5 Da, respectively. Protein identifications were accepted as true positive if at least two different peptides, resulting in a protein score of ≥10.0, were identified.

1.2.1.4. Data Analysis and Target Selection

Several identified proteins were intracellular proteins of highly abundant proteins such as ribosomal proteins. To discriminate between such contaminants and putative membrane targets, the identified proteins were analyzed for their localization within the bacteria using publicly available online tools. (http://bp.nuap.nagoya-u.ac.jp/sosui/sosuigramn/sosuigramn_submit.html, K. Imai et al., *Bioinformation* 2(9), 417-421, 2008). Proteins that were assigned as extracellular or outer membrane protein were selected for further analysis. In addition, proteins that were annotated by the UniprotKB Database as a homologue to known extracellular or outer membrane proteins were selected as well.

1.2.2. Comparative Proteomics

The concept of this method is to focus on polypeptides for which expression is experimentally confirmed in various and different *Acinetobacter* strains. Accordingly, the whole proteome of five *A. baumannii* strains was determined by mass spectrometry. The five strains were selected due to their diverse sources of isolation. To enrich for putative targets that are present on the extracellular surface, protein preparations were enriched for outer membrane proteins prior MS analysis according to their hydrophilic and hydrophobic properties. The peptides identified by mass spectrometry were assigned to proteins using publicly available databases and selected according to IT-predictions and literature searches.

1.2.2.1 Preparation of Bacterial Cultures

*A. baumannii* strains ATCC19606, BMBF65, SDF, ACICU, AYE (see Table 6, above) were streaked onto BHI-Agar plates and incubated overnight (16 h-24 h) at 37° C. The agar plates, containing visible bacterial colonies were used to inoculate 75 ml LB and cultures were incubated for 25 h at 37° C. shaking at 200 rpm. The $OD_{600}$ of the cultures was measured and LB (0.5 l) was inoculated with overnight culture at a starting $OD_{600}$ of 0.02. The 0.5 l cultures were incubated overnight at 37° C. shaking at 200 rpm. $OD_{600}$ was measured and 900 OD/ml of each culture were used for protein preparation.

1.2.2.2 Outer Membrane (OM) Protein Preparations

OM-proteins were essentially prepared as described previously by Arnold and Linke (*Curr Protoc Protein Sci.*; Chapter 4:Unit 4.8.1-4.8.30., 2008) with slight modifications to prepare OM-proteins for further downstream analysis. 900 OD/ml were pelleted at 4° C. for 20 minutes and 4000 g. All following steps were performed on ice with chilled solutions and apparatus at 0° C. to 4° C. The bacteria were resuspended in 7 ml resuspension buffer (0.1 M NaCl, 10 mM $MgCl_2$, 50 mM Tris-HCl, pH=8.0, 10 mg/l DNase I (Sigma-Aldrich,)) and 0.1 ml protease inhibitor cocktail (Sigma-Aldrich,) was added. The suspension was sonicated 5 times for 10 seconds at the level 5 using the Sonifier B-12 (Branson Sonic Power Company, CT, USA) with intervals of 1 minute on ice. The lysate was incubated on ice for 30 minutes and subsequently centrifuged at 2000 g for 15 minutes to remove intact bacteria. The supernatant was transferred to centrifuge tubes, capable for ultracentrifugation, and resuspension buffer was added to a final volume of 12 ml. The solution was centrifuged at 100'000 g and 4° C. for 1 hour. Supernatant was discarded and the pellet resuspended in 12 ml resuspension buffer containing 0.1 ml protease inhibitor cocktail. The ultracentrifugation was repeated and the pellet resuspended in 12 ml CM buffer (0.1 M NaCl, 50 mM Tris-HCl, pH=8.0, 1% (w/v) Sodium N-Lauroylsarcosinate (Fluka)). 0.1 ml protease inhibitor cocktail was added to the suspension and the mixture incubated at room temperature for 30 minutes by rotating the tube on an intelli-mixer (LTF Labortechnik, Germany) set to an angle of 90° and 25 rotations per minute. The solution was ultracentrifuged and the pellet washed three times in 12 ml cold $ddH_2O$ by resuspension and ultracentrifugation as described above. At this stage the pellet was frozen at −20° C. until further use. The OM-protein preparation was chloroform/methanol precipitated (Wessel D. and Flügge U., *Anal. Biochem.* 138, 141-143, 1984) dividing the OM-protein preparation into two aliquots containing 45% and one aliquot containing the remaining 10%. The pellets were stored at −20° C. For protein quantification the chloroform/methanol precipitated 10% aliquot was resuspended in 0.1 ml water of which 50 µl were hydrolyzed with 50 µl 1M NaOH for 2 minutes at room temperature and neutralized with 0.1 ml 0.5 M HCl. The hydrolyzed sample was titrated and protein quantified using Bradford protein reagent (Biorad, CA; USA) according to manufacturer's instructions. Titrated bovine serum albumin, hydrolyzed like the samples, was used as a standard for quantification.

1.2.2.30M-Proteome Determination—LC-MS and Data Analysis

The proteins were solubilized in 8 M urea solution, reduced with 1 mM DTT for 30 min at 37° C. and alkylated with 55 mM iodoacetamide for 30 min in the dark at 25° C. The samples were then diluted with 0.1 M ammoniumbicarbonate buffer to a final urea concentration of 1 M. Proteins were digested by incubation with sequencing-grade modified trypsin (1/100; w/w, Promega, Madison, Wis.) overnight at 37° C. Peptides were desalted on C18 reversed-phase spin columns according to the manufacturer's instructions (Microspin, Harvard Apparatus), dried under vacuum and stored at −80° C. until further use.

Peptide mixtures were analyzed using high-resolution nano-LC-MS on a hybrid mass spectrometer consisting of a linear quadrupole ion-trap and an Orbitrap (LTQ-Orbitrap XL, Thermo Fisher Scientific). Peptides were analyzed twice on an Eksigent Nano LC system (Eksigent Technologies) connected to a hybrid mass spectrometer consisting of a linear quadrupole ion-trap and an Orbitrap (LTQ-Orbitrap XL, Thermo Fisher Scientific), which was equipped with a nanoelectrospray ion source (Thermo Scientific). Peptide separation was carried out on a RP-HPLC column (75 µm inner diameter and 10 cm length) packed in-house with C18 resin (Magic C18 AQ 3 μm; Michrom Bioresources) using a linear gradient from 95% solvent A (water, 0.1% formic acid, and 2% acetonitrile) and 5% solvent B (water, 0.1% formic acid, and 98% acetonitrile) to 72% solvent A and 28% solvent B over 60 min at a flow rate of 0.3 μl/min. The LTQ-Orbitrap was operated in data-dependent acquisition mode with the Xcalibur software. Survey scan MS spectra were acquired in the Orbitrap on the 350-2000 m/z range with the resolution set to a value of 60,000. The five most intense ions per survey scan were selected for collision induced dissociation (CID) fragmentation, and the resulting fragments were analyzed in the linear trap (LTQ). Dynamic exclusion was used within 30 s to prevent repetitive selection of the same peptide. Singly charged ions and ions with unassigned charge states were excluded from triggering MS/MS scans.

Raw data files from the MS instruments were converted with ReAdW into mzXML files and mzXML files were searched with Sorcerer-SEQUEST (Eng et al., *J Am Soc Mass Spectrom.* 1994; 5(11): 976-989) against a *Acinetobacter baumannii* protein database (ACIB3) from the UniProtKB/Swiss-Prot Protein Knowledgebase (Version 56.9) containing 3453 protein entries (292 in UniProtKB/Swiss-Prot+3161 in UniProtKB/TrEMBL). Statistical analysis of each search result for each LC-MS analysis was performed using the Trans-Proteomic Pipeline TPP (Keller et al., *Mol Syst Biol.* 2005; 1:2005.0017): v4.0 JETSTREAM rev 2 including PeptideProphet (Keller A, et al., *Anal. Chem.* 2002; 74(20): 5383-5392) and ProteinProphet (Nesvizhskii et al., *Anal. Chem.* 2003; 75(17):4646-4658). The ProteinProphet probability score was set to 0.9, which resulted in an average protein and peptide false discovery rate of less than 1% for all search results estimated by ProteinProphet and PeptideProphet.

The database search criteria included: 50 ppm mass tolerance for the precursor ion, variable modifications of 15.994920 Da for methionines (representing oxidized methionines), 57.021465 Da for carbamidomethylation as static modification for cysteines, at least one tryptic terminus per peptide, and up to two missed cleavage sites.

1.2.2.4 Data Analysis and Target Selection

To select for putative targets from the OM-proteome, the identified proteins of 5 different strains (see above, Table 6) were analyzed for their localization within the bacteria using publicly available online tools (PSORTb v3.0, Yu et al., *Bioinformatics* 26(13):1608-1615, 2010). Proteins that were present in the OM-proteome of all 5 strains and predicted to locate either extracellular or to the outer membrane were individually analyzed in detail. This included the genomic conversation among 14 publicly available reference genomes (presence/absence of gene and percentage of amino acid identity) and the predicted topology of the protein within the outer membrane using the publicly available online tool HHpred (Söding et al., *Nucleic Acids Res.* 2005 Jul. 1; 33 (Web Server issue): W244-8.). If available literature concerning the *Acinetobacter* protein identified or homologues in other species was considered as well.

Proteins that (1) were encoded by at least 13 of 14 genomes analyzed with an amino acid conversation of ≥90% and (2) were predicted to display parts of the protein sequence on the extracellular side of the outer membrane were considered as putative antibody targets. In those cases where the literature predicted homologues of such a putative antibody target to be down-regulated or absent in antibiotic resistant *A. baumannii* strains, the targets were no longer followed. For instance, the outer membrane protein CarO was previously shown to be down-regulated in Carbapenem resistant *A. baumannii* strains (Mussi et al., *Antimicrob Agents Chemother.* April; 49(4): 1432-40, 2005). Despite the fact that the target was identified by comparative proteomics as well as specific target selection, CarO was considered a target of little clinical relevance and therefore was not investigated further.

1.2.3. Specific Target Identification

This method focuses on specific targets that are recognized by antibodies present in sera of convalescent *A. baumannii* patients. Accordingly, OM protein preparations enriched for outer membrane proteins, were separated by 2-dimensional gel electrophoresis (2DE). The 2DE consisted of an isoelectric focusing (IEF) followed by SDS-polyacrylamide gel electrophoresis (PAGE) step to resolve the OM proteins. Proteins recognized by patient sera were determined by immunoblot analysis. To increase the chance of identifying proteins that are expressed by various strains, immunoblots of at least two *A. baumannii* strains were compared and proteins present in all strains analyzed were selected for protein identification by MS-analysis. The proteins were individually characterized and selected according to IT-predictions and literature searches.

1.2.3.1 Preparation of Bacterial Cultures and OM-Protein Preparations

*A. baumannii* strains ATCC19606, BMBF-65 and Berlin-95 (see Table 6) were used to generate OM-protein preparation as described in 1.2.2.2.

1.2.3.2 Two-Dimensional Gel Electrophoresis (2DE)

Isoelectric focusing (IEF) was performed according to the manufacturer's instructions (GE Healthcare, United Kingdom) using the Ettan™ IPGphor™ 3 IEF System (GE Healthcare). Briefly, Immobiline pH3-10 NL 7 cm DryStrips (GE Healthcare) were rehydrated overnight at room temperature in 125 μl rehydration solution (8M Urea (Sigma-Aldrich), 2% CHAPS (Sigma-Aldrich), 40 mM DTT (Fluka,), 0.5% IPG buffer (GE Healthcare), 0.002% bromophenol blue). OM-preparations (20-30 μg) were dissolved in 50-100 μl rehydration solution, vortexed for 30 seconds and incubated at room temperature for several minutes. The sample was then centrifuged for 2 minutes at >14000 g and the supernatant was used for IEF. In duplicates, sample was loaded onto rehydrated Immobiline DryStrips using the cup-loading system and overlaid with mineral oil. Proteins were separated using the running conditions 300V for 1 h, linear gradient 300V-1000V for 30 minutes, linear gradient 1000V-5000V for 1 h 30 minutes and 5000V for 36 minutes. The strips were frozen immediately at −20° C.

The $2^{nd}$ dimension was performed exactly as described by the manufacturer's instructions (Invitrogen, USA) using NuPAGE® Novex 4-12% Bis-Tris ZOOM® Gels (Invitrogen) and 10 μl of Novex® Sharp Pre-stained Protein Standard (Invitrogen). One duplicate of the gels was used for blotting onto nitrocellulose membranes (Invitrogen) as described by the manufacturer's instructions for Tris-Glycine gels (Invitrogen), using 30V for 80 minutes as running conditions. The nitrocellulose membrane was stained with Ponceau S solution (Sigma-Aldrich) and a picture was recorded. The membrane was incubated for 1 h at room temperature in blocking buffer (5% Skim milk (Fluka) in PBS-T (PBS containing 0.05% Tween 20® (Sigma-Aldrich). Individual patient sera or mixtures were diluted 1:500 in blocking buffer and incubated with the membrane overnight at 4° C. The membrane was washed three times for five minutes in PBS-T and incubated with a human IgG specific secondary antibody (Invitrogen) at a dilution of 1:1000 in blocking buffer for 1 h at room temperature. The membrane was washed again three times and bound antibody was detected using TMB substrate (Promega). Proteins that were detected by a given patient serum in all *A. baumannii* strains tested, were selected for protein identification. Therefore proteins in the second duplicate of the 2DE-gels were visualized with Instant Blue™ (Expedeon, Cambridgeshire, UK). Proteins positive in immunoblots were localized in the gel duplicate by comparing the protein pattern of the gel with the protein pattern of the Ponceau S stained membrane and the immunoblot signals. The protein spots were excised and stored at −80° C. until protein identification by MS analysis.

1.2.3.3. MS-Analysis of Tryptic Digest

Proteins were identified from excised gel fragments by LC/ESI/MS/MS by the Protein Analysis Group, Functional Genomics Center Zurich, Switzerland using standard procedure. Briefly, gel pieces were washed twice with 100 µl 100 mM $NH_4HCO_3$/50% acetonitrile, washed with 50 µl acetonitrile. All three supernatants were discarded and 10 µl trypsin (100 ng in 10 mM Tris/2 mM $CaCl_2$, pH 8.2), 20 µl buffer (10 mM Tris/2 mM $CaCl_2$, pH 8.2) added and incubated overnight at 37° C. Supernatant was removed and gel pieces extracted twice with 100 µl 0.1% TFA/50% acetonitrile. All three supernatants were combined and dried. The sample was dissolved in 25 µl 0.1% formic acid and transferred to an autosampler vial for LC/MS/MS. 5 µl were then injected for peptide identification. Database searches were performed by using the ProteinLynx Global Server (SwissProt, all species) and Mascot (NCBInr, all species) search programs.

1.2.3.4. Data Analysis and Target Selection.

Proteins that were identified as *A. baumannii* protein and predicted to be or annotated as an outer membrane protein were chosen as putative targets. The targets were no more followed in cases where the literature predicted homologues of such a putative antibody target to be down-regulated or absent in antibiotic resistant *A. baumannii* strains.

Example 2

IT Predictions

For IT predictions of protein structure the Bioinformatics Toolkit form the Max-Planck Institute for developmental Biology in Tubingen was used (Biegert et al., *Nucleic Acids Res.* 34, W335-339). Tertiary structures were predicted using the tool HHpred (Soding J. et al., *Bioinformatics*, 2005, 21, 951-960,) that builds a hidden Markov Model (HMM) of the query sequence and compares it with a database of HMMs, representing annotated protein families (e.g. PFAM, SMART, CDD, COGs, KOGs) or domains with known structure (PDB, SCOP). As a setting for the online prediction, the HMM database pdb70.sub. —3Sep11 was used and HHblits were set to MSA generation method with maximal 3 iterations and local alignment mode. The predicted structures were assumed to be true with a high probability to be a true positive (>90%) and a homology that covers most of the query sequence. Where multiple hits met the requirements, the two hits with the highest probability and lowest E- and P-values were used as representing tertiary structure. Representing predicted tertiary structures to SEQ ID NOs: 2, 4, 6, 8, 10, 12, 14, 16 are assigned in Table 4 and can be downloaded from the pubmed online server or otherwise obtained with reference to Wang Y. et al., *Nucleic Acids Res.* 2007 January.

Prediction of N-Terminal Leader Sequence:

The N-terminal leader sequence was determined using the SignalP 3.0 Server Bendtsen J. D. et al., *J. Mol. Biol.*, 340:783-795, 2004.) for gram negative bacteria using hidden Markov models and Neural Networks.

Prediction of Sub Cellular Protein Localization:

The public available online tool Psortb v3.0 Yu et al., 2010 , *Bioinformatics* 26(13):1608-1615) was used for prediction of sub cellular localization. "Bacteria" and "gram-negative stain" were chosen as settings for prediction. The protein sequences were entered as single letter amino acid code.

For the shedome analysis, the public available online tool SOSUI.sub.GramN was used Imai et al., *Bioinfomation* 2(9), 417-421 (2008)), entering the protein sequences as single letter amino acid code.

Determination of Amino Acid Conservation and Gene Prevalence:

For determination of gene prevalence and amino acid conservation, the amino acid sequence to be analyzed was entered into the genomic blast online tool "tblastn" Cummings L, et al., *FEMS Microbiol Lett.* 2002 Nov. 5; 216(2): 133-8; Altschul et al., *Nucl Acid Res.*, 25:3389-3402, (1997)) as query sequence using single amino acid single letter code. All *A. baumannii* genomic databases were selected. Default BlastP parameters were chosen (BLOSUM62 Matrix, Gap costs to open=11, Gap costs to extend=1, using low complexity filter and composition based statistics). The Expect-values to be accepted was kept at a default setting of 10. Of the results, the prevalence and the percentage amino acid identity among the reference genomes (Table 4) was used for target selection.

In cases where a DNA sequence was used as a Query sequence, blastn was used instead, using default settings (BLOSUM62 Matrix, Gap costs to open=5, Gap costs to extend=2, Match scores=2, mismatch score=−3). Depending on the length of the sequence the program used low or strong complexity filter.

Example 3

Generation of Expression Vectors for the Generation of Recombinant Antigens

The nucleic acid sequences encoding the polypeptides of the present invention were amplified by PCR from genomic DNA of *A. baumannii* (ATCC19606) using primers containing appropriate restriction sites for cloning. PCR products were cloned in frame into the expression vector pET-28a(+) (Novagen; Germany) resulting in recombinant protein with an N-terminal His-tag. All oligonucleotides were generated at Microsynth (Balgach, Switzerland). For AB023, AB024, AB025, AB030, FimA, CsuAB and OmpA the whole coding sequence (cds) without the N-terminal signal peptide was cloned. The N-terminal leader sequence was determined and removed for cloning and expression of recombinant proteins. For AB031 the 78 amino acid extracellular loop was cloned as it was the only region of more than 2 amino acids within this molecule predicted to be on the extracellular side and therefore accessible to antibodies. The expression plasmids were sequenced at Microsynth to exclude PCR artifacts. SEQ ID NOs: 33 and 34 show the nucleotide sequence of the sequencing primer T7 and T7 term respectively. An additional sequencing primer, consisting of the nucleotide sequence described as SEQ ID NO: 35, was used for the expression vector of AB030 described in example 3.4.

3.1 Expression Vector for AB023 (SEQ ID NO: 1)

SignalP 3.0 Server predicted an N-terminal signal sequence at position 1-26 for SEQ ID NO: 2. The oligonucleotides oAB023wss GGCAGGATCCGCTGC TGCATTTGACCC (SEQ ID NO: 17) and oAB023as CGGAATGTCGACTTAGAA TGCAGTTG (SEQ ID NO: 18) were designed to bind at the position 76-95 and 1241-1254 of SEQ ID NO: 1 respectively. Restriction sites, added to the oligonucleotides oAB023wss and oAB023as for cloning, are underlined. The cds homologues to SEQ ID NO: 1 position 76-1254 was amplified by PCR from genomic DNA of ATCC19606 using the P:IX Polymerase (Invitrogen) and the oligonucleotide pair oAB023wss/oAB023as. Per 50 µl reaction, 50 ng of genomic DNA, 1 U P:IX polymerase, 1 mM MgSO4, 2× pfx buffer, 0.3 mM dNTP (each), 0.3 fl M oligonucleotide (each) were used. The PCR thermo cycle program was (94° C., 4 min) 35×(94° C., 15 s; 55° C., 30 s; 65° C., 2 min) (65° C., 5 min). The PCR product was purified using QIAquick gel extraction kit (QIAGEN, 28704) according to the manufactures instructions. The purified PCR product and 100 ng of the vector pET-28a(+) were digested using the restriction enzymes BamHI and SalI (Fermetas, ER0051, ER0641) and the digests were purified by using QIAquick PCR Purification Kit (QIAGEN, 28104) according to the manufactures instructions. Subsequently 50 ng vector was ligated at a molar ratio of 1:2 with the PCR product for 2 h at room temperature using 2 units ligase (Fermentas, Canada) in a total volume of 20 µl and I×ligase buffer (supplied with ligase) Ligation reaction was transformed into chemicompetent E. coli (DH5a) and selected on LBA-plates containing 50 µg/ml kanamycin (Applicem) using standard procedures (Maniatis). Resistant colonies were selected for purification of plasmid DNA using commercially available kits (Promega, Wis., USA or QIAGEN, Germany) and purified plasmids were sequenced at Microsynth (Balgach, Switzerland) using the standard sequencing primers T7 (TAATACGACTCACTATAGG-SEQ ID NO; 33)and T7 term (TGCTAGTTATTGCTCA-GCGG-SEQ ID NO: 34) to verify correct integration of the PCR product. The expression vector for AB023 encoded the same amino acid sequence as expected from the Acinetobacter genome sequence of ATCCI9606 (DOCDE3) except for the signal peptide (amino acids 1-26) that was replaced by the His-tag from the vector.

3.2 Expression Vector for AB024 (SEQ ID NO: 3)

SignalP 3.0 Server predicted an N-terminal signal sequence at position 1-29 for SEQ ID NO: 4. The oligonucleotides oAB024wss GGCAGGATCCGCAACTTCTGATAAAGAG (SEQ ID NO: 19) and oAB024as CAAAGTCGACTTAGAAGCTATATTTAGCC (SEQ ID NO: 20) were designed to bind at the position 88-105 and 1287-1305 of SEQ ID NO: 3 respectively. Restriction sites, added to the oligonucleotides oAB024wss and oAB024as for cloning, are underlined. The cds homologues to SEQ ID NO: 3 position 88-1305 was amplified by PCR and cloned into pET-28a(+) exactly as described for the expression vector of AB023.

The expression vector for AB024 encoded the same amino acid sequence as expected from the Acinetobacter genome sequence of ATCC19606 (DOCDN5) except for the signal peptide (amino acids 1-29) that was replaced by the His-tag from the vector.

3.3 Expression Vector for AB025 (SEQ ID NO: 5)

SignalP 3.0 Server predicted an N-terminal signal sequence at position 1-21 for SEQ ID NO: 6. The oligonucleotides oAB025wss TCGCGGATCCCAAGGTTTAGTGCTTAATAATGATG (SEQ ID NO: 21) and oAB025as CGACAAGCTTAGAAACCAAACATTTTACGCTC (SEQ ID NO: 22) were designed to bind at the positions 67-88 and 1422-1446 of SEQ ID NO: 5 respectively. Restriction sites, added to the oligonucleotides oAB025wss and oAB025as for cloning, are underlined. The cds homologues to seq5 position 67-1446 were amplified by PCR and cloned into pET-28a(+) exactly as described for the expression vector of AB023 with the modification that the restriction enzyme HindIII (Fermentas, ER0501) was used instead of SaiI.

The expression vector for AB025 encoded the same amino acid sequence as expected from the Acinetobacter genome sequence of ATCC19606 (DOC8X7) except for the signal peptide (amino acids 1-21) that was replaced by the His-tag from the vector.

3.4 Expression Vector for AB030 (SEQ ID NO: 7)

SignalP 3.0 Server predicted an N-terminal signal sequence at position 1-44 for SEQ ID NO: 8. The oligonucleotides oABO30wss CTTGTGGATCCCAAAGTTCGGCTGAGACC (SEQ ID NO: 23) and oAB030as AAAGTCGACTTAAAGTTGTGGACCAATAAAGAAATG (SEQ ID NO: 24) were designed to bind at the position 133-150 and 2695-2721 of SEQ ID NO: 7 respectively. Restriction sites, added to the oligonucleotides oABO30wss and oAB030as for cloning, are underlined. The cds homologues to SEQ ID NO: 7 position 133-2721 were amplified by PCR and cloned into pET-28a(+) exactly as described for the expression vector of AB023 with the modification that the elongation time of the PCR was increased to 2 min 30 sec and the cycle number reduced to 30.

The expression vector for AB030 encoded the same amino acid sequence as expected from the Acinetobacter genome sequence of ATCC19606 (D00629) except for the signal peptide (amino acids 1-44) and the amino acid at position 58 that encodes for a threonine instead of serine. Since homologues of AB030 in other Acinetobacter baumannii strains (e.g. AB307-B7H123) contain at this position a threonine, this difference from the expected sequence was tolerated.

3.5 Expression Vector for AB031L (SEQ ID NO: 9)

The homology detection and structure prediction software HHPred Soding et al., Nucleic Acids Res.; 33 (Web Server issue):W244-8, 2005 Jul. 1) was used to predict the structure of AB031. A structural homologue of AB031 (Pubmed Protein ID 1ek9—Outer membrane protein TOLC) was predicted with highest probability (100%) and an E-value (0) of highest statistical significance. The alignment predicted the 78 amino acid sequence at position 87-164 of SEQ ID NO: 10 to locate to the extracellular side of the bacteria.

The oligonucleotides oAB031L1wss AAAGGATCCAGAGCATATGCTTTTCATAGTG (SEQ ID NO: 25) and oAB031L1as AAAGTCGACTTAAGATGGTCGGACTACTTGGTCTTCT (SEQ ID NO: 26) were designed to amplify the 78 amino acid loop by PCR. Restriction sites, added to the oligonucleotides oAB031L1ss and oAB031L1as for cloning, are underlined. The cds homologues of the 78 amino acid sequence was amplified by PCR from genomic DNA of ATCC19606 using the Dream-Taq polymerase (Fermentas, EP0701) and the oligonucleotide pair oAB031L1wss/oAB031L1as. Per 50 µl reaction, 50 ng of genomic DNA, 0.5 U taq polymerase, 1× taq buffer, 0.2 mM dNTP (each), 0.2 µM oligonucleotide (each) were used. The PCR thermo cycle program was (94° C., 3 min) 5× (94° C., 15 s; 50° C., 15 s; 72° C., 2 min) 25× (94° C., 15 s; 55° C., 15 s; 72° C., 2 min) (72° C., 5 min). The PCR product was cloned into pET-28a(+) as described for the expression vector of AB023. The expression vector for AB031L1 encoded the same amino acid sequence as expected from the 78 amino acid sequence of SEQ ID NO: 10.

3.6 Expression Vector for FimA (SEQ ID NO: 11)

SignalP 3.0 Server predicted an N-terminal signal sequence at position 1-20 for SEQ ID NO: 12. The oligonucleotides oFimAwss GGACGA GGATCCGCTGATGGTACAATTACA (SEQ ID NO: 27) and oFimAas AACT AAGCTTTCAACCCATTGATTGAGCAC (SEQ ID NO: 28) were designed to bind at the position 61-78 and 392-407 of SEQ ID NO: 12 respectively. Restriction sites, added to the oligonucleotides for cloning, are underlined. The cds homologues to seq11 position 61-407 was amplified by PCR and cloned into pET-28a(+) exactly as described for the expression vector of AB025.

The expression vector for FimA encoded the same amino acid sequence as expected from the *Acinetobacter* genome sequence of ATCC19606 (D00767) except for the signal peptide (amino acids 1-20) that was replaced by the His-tag from the vector.

3.7 Expression Vector for CsuAB (SEQ ID NO: 13)

SignalP 3.0 Server predicted an N-terminal signal sequence at position 1-23 for SEQ ID NO: 14. The oligonucleotides oCsuABwss AATACT GGATCCGCTGTTACTGGTCAG (SEQ ID NO: 29) and oCsuABas AACT AAGCTTTTAGAAATTTACAGTGACTAATAGAG (SEQ ID NO: 30) were designed to bind at the position 70-84 and 512-537 of SEQ ID NO: 13 respectively. Restriction sites, added to the oligonucleotides oCsuABwss and oCsuABas for cloning, are underlined. The cds homologues to SEQ ID NO: 13 position 70-537 was amplified by PCR and cloned into pET-28a(+) as described for the expression vector of AB025.

The expression vector for CsuAB encoded the same amino acid sequence as expected from the *Acinetobacter* genome sequence of ATCC19606 (D0C5S9) except for the signal peptide (amino acids 1-23) that was replaced by the His-tag from the vector.

3.8 Expression Vector for OmpA (SEQ ID NO: 15)

SignalP 3.0 Server predicted an N-terminal signal sequence at position 1-22 for SEQ ID NO: 16. The oligonucleotides oOmpAwss CTGCT GAATTCGGCGTAACAGTTACTCC (SEQ ID NO: 31) and oOmpAas CAAGAAAGCTTATTATTGAG (SEQ ID NO: 32) were designed to bind at the position 67-83 and 1064-1071 of SEQ ID NO: 15 respectively. Restriction sites, added to the oligonucleotides oOmpAwss and oOmpAas for cloning, are underlined. The cds homologues to SEQ ID NO: 15 position 67-1071 were amplified by PCR and cloned into pET-28a(+) exactly as described for the expression vector of AB023 with the modification that the restriction enzymes EcoRI and HindIII (Fermentas, ER0271, ER0501) were used instead.

The expression vector for OmpA encoded the same amino acid sequence as expected from the *Acinetobacter* genome sequence of ATCC19606 (D0CDF2) except for the signal peptide (amino acids 1-22) that was replaced by the added His-tag from the vector.

Example 4

Expression and Purification of Recombinant Proteins 4.1 Expression of Recombinant Proteins in *E. coli*.

For recombinant expression of His-tagged proteins, chemicompetent *E. coli* BL-21(DE3) were transformed with the individual expression vectors described above and selected on LBA-plates containing 50 µg/ml kanamycin using standard procedures. Overnight culture in LB containing 50 µg/ml kanamycin of resistant colonies were used to start a 0.5 l LB culture containing 50 µg/ml kanamycin at an $OD_{600}$ of 0.2 or lower. The culture was incubated at 37° C. and 200 rpm until an $OD_{600}$ of 0.5-1 was reached. IPTG (Sigma-Aldrich) was added at a concentration of 1 mM and bacteria were incubated further at 37° C. and 200 rpm for 3-4 h. Bacteria were centrifuged (3500 g, 10 min) and pellet was frozen at −20° C.

4.2 Extraction of Recombinant Proteins from *E. coli* Bacterial Pellets.

Bacterial cell pellet was resuspended in 10 ml cell disruption buffer (0.15 M NaCl, 10 mM $MgCl_2$, 10 mM $MnCl_2$, 20 mM Tris-HCl, pH=8.0, 10 mg/l DNaseI), the suspension was sonicated on ice as described in 1.2.2.2 and incubated on ice for 30 minutes. The suspension was centrifuged (4000 g, 10 min at 4° C.), supernatant was discarded and pellet resuspended in 10 ml detergent buffer (0.15 M NaCl, 20 mM Tris-HCl, pH=8.0, 1% TritonX 100) by mechanical forces. The suspension was centrifuged at 8000 g, 4° C. for 10 minutes. In case of his tagged AB031L1, the supernatant was supplemented with 5 mM DTT to generate AB031L1 binding buffer and immediately used for Ni-NTA affinity purification. For all other recombinant proteins, the supernatant was discarded and the pellet was washed twice in 20 ml deionized cold water by resuspending the pellet and repeating the centrifugation. The washed pellet was frozen at −20° C. until further use.

Recombinant protein was extracted in 10-20 ml binding buffer by incubating the resuspended pellet for 30 min rotating at room temperature. For His-tagged FimA, the pellet was extracted with binding buffer G (6M GuHCl, 0.5 M NaCl, 20 mM Imidazole (Merck, Germany), 5 mM DTT, 20 mM Tris-HCl, pH=9.0) while for His-tagged AB023, AB024, AB025, AB030, CsuAB and OmpA the pellet was extracted with binding buffer U (8 M Urea, 0.5 M NaCl, 20 mM Imidazole, 5 mM DTT, 20 mM Tris-HCl, pH=8.0).

4.3 Ni-NTA Purification of Recombinant his Tagged Proteins.

HisTrap™ HP columns (GE Healthcare, 17-5247-01) were used for affinity purification of his-tagged proteins. The Äkta avant apparatus (GE Healthcare) was used to operate the purification at a system flow rate of 1 ml/min and 0.5 MPa pre and 0.3 MPa delta column pressure limit. The columns were equilibrated with 5 column volumes (CV) running buffer. The running buffer consisted of the same components as the binding buffer for each antigen, except that no DTT was present. Binding buffer containing the extracted recombinant proteins were applied to the column and the column was washed with running buffer until the UV 280 nm signal recorded was stable. Bound proteins were eluted from the column using 10 CV of a linear gradient of 20 mM to 500 mM imidazole in running buffer. Fractions of 0.5 ml were collected and analyzed for presence, purity and quantity of recombinant protein by SDS-PAGE and Coomassie staining respectively. Fractions of highest purity and concentration of recombinant protein were pooled and quantified by comparison titrated recombinant protein with a titrated BSA standard (0.5, 1, 2, 4, 6 μg per lane) on an SDS-PAGE gel stained with Coomassie.

FimA was precipitated by adding ethanol to 90% (v/v), cooled to −80° C. and centrifuged at >14'000 rcf at 4° C. for 30 minutes and dried by Speed Vac. FimA was either stored as a pellet or dissolved in binding buffer U at a concentration of 1 mg/ml at −20° C. All other proteins were diluted in running buffer to 1 mg/ml or 2 mg/ml and stored at −20° C.

4.4 Refolding of OmpA

OmpA was refolded according to McConnell et al. (McConnell, Michael J.; Pachón, Jerónimo (2011): *Protein Expression and Purification* 77 (1), S. 98-103). Briefly, his tagged OmpA (1 ml at 1-2 mg/ml) was 50-fold diluted in 50 ml refolding buffer (10 mg/ml n-octyl-β-D-glucopyranoside, 20 mM NaPi, pH 7.4) and incubated overnight at 42° C. The volume was concentrated to 1 mg/ml OmpA using Amicon Ultra-15 centrifugal devices with a 10 kDa cut off (Millipore, Mass., USA).

Example 5

Generation of Polyclonal Rabbit Sera and Purification of Rabbit IgG

Antigens were individually prepared for generation of rabbit immune sera. AB030 was ethanol precipitated and resuspended in 1 M Urea buffer (1 M Urea, 10 mM Tris-HCl, pH=8.0, 0.1% SDS) at a concentration of 1.2 mg/ml. AB031-L1 was precipitated and the pellet dissolved in 1 M Urea buffer at a concentration of 2.5 mg/ml. Antigens (1.5 mg each) were sent to Biogenes (Berlin, Germany) where rabbit antisera were generated. Of each rabbit preimmune serum was taken before immunization. For each antigen, two rabbits were immunized and boosted 7 and 14 days after immunization. On day 28, animals were boosted and 20 ml serum prepared and analyzed by ELISA and immunoblot analysis using recombinant protein. Total serum was prepared between day 42 and 56 after immunization. Sera contained 0.02% thimerosal as preservative.

Total IgG was purified from serum by protein A affinity purification using standard protocols. Purified total IgG was either in Tris-Glycine buffer pH=7.5, 250 mM NaCl, 0.02% thimerosal or in Tris-Glycine buffer pH=7.5.

Thimerosal was removed by dialysis prior to experiments with live bacteria. Briefly, sera and total IgG were dialyzed twice for 30 minutes at room temperature and once overnight at 4° C. against 1-2 l PBS using Slide-A-Lyzer dialysis cassettes with a 10 kDa cut off (Thermo Fisher Scientific, MA, USA).

Example 6

Immunoblot Analysis

Reference strains (*E. coli, P. aeruginosa* or *A. baumannii*) or clinical isolates of *A. baumannii* were grown in LB media (if not otherwise mentioned) to stationary phase or logarithmic phase ($OD_{600}$ 0.3-1.2) and centrifuged for 5-10 min at 4000 g. Bacterial cell pellets were resuspended in water and lysed with an equal volume of 2×SDS sample buffer (0.1 M Tris-HCl pH=6.8, 4% (w/v) SDS, 0.2% (w/v) bromophenol blue, 20% glycerol, 0.2 M DTT) or 2× Novex® Tris-Glycine SDS Sample Buffer with reducing agent (LC2676, Invitrogen) at a final concentration equivalent to 12 $OD_{600}$/ml and heated for 10 minutes at 98° C. Purified proteins were diluted in SDS sample buffer accordingly, reaching a concentration of 1-2 μg per 10 μl or an equivalent $OD_{600}$/ml. Per lane of a Novex® 4-20% Tris-Glycine gel (Invitrogen), 10 μl of bacterial suspension or purified antigen were loaded. 5-10 μl molecular weight standards (SeeBlue® Pre-stained, or Novex® Sharp Pre-stained Protein Standard, Invitrogen) were loaded on a separate lane. Proteins were separated by SDS-PAGE, according to the manufacturer's instructions, using the running conditions 140 V for 90 minutes (Invitrogen). In cases where only purified antigens were separated, NuPAGE® 4%-20% Bis-Tris gels (NP0322BOX, Invitrogen) were used instead and separated according to the manufacturer's instructions for denatured, reduced samples using MES running buffer (Invitrogen).

Gels were either stained with Coomassie as described above or blotted onto a nitrocellulose membrane and analyzed by Ponceau S staining and immunoblot analysis as described above for 2DE. Rabbit antisera were diluted 1:500-1:1000 and human sera 1:500. Secondary antibodies, HRP-Goat anti-rabbit IgG (Sigma-Aldrich) and HRP-Goat anti-human IgG (Invitrogen), were used at a dilution of 1:2000.

Results of immunoblot analysis are shown in FIGS. 3, 4, 5, 6C and 9C.

Example 7

ELISA 96-well ELISA plates (Nun, 439454) were coated overnight at 4° C. or for 2 h at room temperature for each antigenic polypeptide diluted in coating buffer at 1 μg/ml and 0.1 ml per well. Urea running buffer [8 M urea, 0.5 M NaCl, 20 mM Imidazol, 20 mM Tris-HCl, pH 8.0] was used for His-tagged AB023, AB024, AB025, AB030, FimA and CsuAB as coating buffer. PBS was used as coating buffer for refolded OmpA and AB031 L1.

Coated ELISA plates were washed three times with PBS-T (0.35 ml per well using Skan washer 400, Skatran). Human sera or rabbit sera were used as primary antibody. Primary antibody was diluted in PBS-T and 0.1 ml added to each well. Prior to use as primary antibody human sera were titrated starting at a dilution of 1:200 and rabbit antisera were titrated starting at a dilution of 1:100 or 1:200. ELISA plates were incubated with primary antibodies for 1 h at room temperature and then washed three times in PBS-T. HRP-Goat anti-human IgG (Invitrogen) or HRP-Goat anti-rabbit IgG (Sigma-Aldrich) were used as secondary antibodies at a dilution of 1:2000 and 1:5000, respectively. ELISA plates were washed again three times in PBS-T and bound HRP was detected by the color change of O-Phenylenediamine (Fluka). The reaction was stopped using 1 M HCl and quantified by measuring the OD at 490 nm.

Use of human sera as primary antibody allows detection of targets while use of rabbit sera proves the immunogenicity of the targets.

Figure 1:
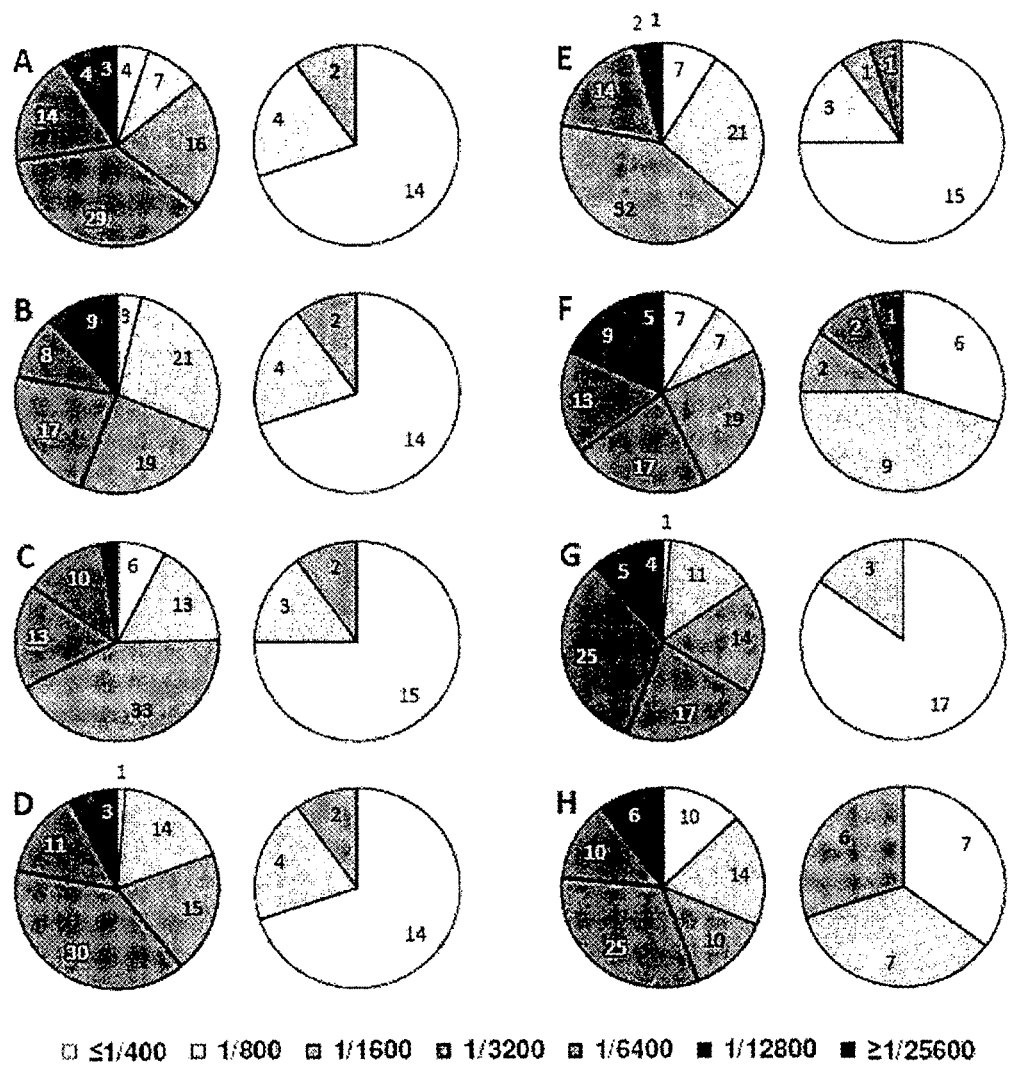
FIG. 1 shows IgG titres in sera from convalescent *A. baumannii* patients (left) and ordinary, randomly selected blood donors (right).

Results of ELISA are shown in FIGS. 1 and 2.

Example 8

Bacterial FACS Analysis $OD_{600}$ of stationary phase bacteria or logarithmic growing bacteria was measured. Bacteria were diluted in PBS containing 0.5% (w/v) BSA as blocking agent at an $OD_{600}$ of 0.1. Per reaction 0.05 ml of bacterial suspension was used and combined with 0.05 ml primary antibody in round bottom 96-well cell culture dishes (Corning, N.Y., USA).

Unbound antibody was removed by two washing cycles consisting resuspended bacteria in 0.2 ml blocking agent, centrifugation for 10 minutes at 1700 g and removal of supernatant. Optionally at this stage, bound antibody was fixed by incubation in 4% (w/v) formaldehyde/PBS for 10 min on ice. If fixative was used, bacteria were washed twice. Secondary antibody, Goat anti-human IgG-Alexa Fluor 488, Goat anti-human IgM-Alexa Fluor 488 or Goat anti-rabbit IgG-FITC (Invitrogen), 0.1 ml per well, were added at a dilution of 1:1000 and incubated for 30 minutes. Bacteria were washed again and analyzed using a FACS Calibur. Instrument at settings adjusted to optimally discriminate the bacterial population from debris and weak from strong fluorescent signals (Forward scatter: Voltage E01, Amp. Gain: 7.0, log. Sideward scatter: Voltage 659, Amp. Gain: 1.0, log., Fl-1: Voltage 767, Amp. Gain: 1.0, log.). As negative control, wash buffer only, no primary antibody or preimmune serum were used. Patient sera or rabbit immune sera were used as positive a control (strong signal). All solutions (except bacterial solutions) were sterile filtered to reduce FACS artifacts.

Results are shown in FIGS. 6 A and B and in FIG. 7

Example 9

Immunofluorescence Analysis (IFA)

Various methods were used to prepare bacteria for IFA. Bacterial colonies from LBA or BHI plates were resuspended in 50 µl water at high densities ($OD_{600}$>1) and smeared onto a well of 10-well glass slides (MP Biomedicals Inc., USA). Liquid bacterial cultures were smeared directly onto the slides. The smears were air dried and fixed for 10 min with 4% (w/v) formaldehyde in PBS followed by 3 washing steps using PBS. Alternatively bacteria were fixed for 10 min in −20° C. acetone and air dried. Another approach to prepare bacteria for IFA was to grow liquid bacterial cultures directly on glass slides (BD Biosciences, NJ, USA) to enable biofilm formation. Culture was removed and bacteria attached to the glass slide were fixed as described above.

IFA was performed as follows: fixed bacteria were incubated with blocking agent (PBS containing 1% (w/v) BSA) for at least 30 minutes. Buffer was replaced by primary antibody diluted in blocking reagent. Rabbit immunsera were diluted 1:50-1:500. After incubation for 1 hour bacteria were washed 3-4 times with PBS. Secondary antibodies (goat anti-rabbit IgG-FITC (F2765, Invitrogen), diluted in blocking reagent at a dilution of 1:200-1:400, were incubated for 45 minutes and washed 3-4 times with PBS. Slides were overlaid with Vectashield containing DAPI (H-1200, Vector labs) and sealed with a cover slide and nail varnish. Slides were analyzed and pictures taken using the 100-fold oil immersion objective of the Nikon fluorescence microscope "fluonik" at the Institute of Anatomy at the University of Berne, Switzerland. All steps were performed at room temperature.

Results are shown in FIG. 8B

Example 10

Agglutination Assay

Stationary phase bacteria were diluted in PBS to an $OD_{600}$ of about 3. Logarithmic phase bacteria were concentrated by centrifugation and resuspension in PBS to an $OD_{600}$ of about 3. On a multiwall glass slide, 10 µl bacterial suspension was mixed with an equal volume of antibody at a concentration of 0.2-1.5 mg/ml for total IgG purified from rabbit sera. The concentration depended on the characteristics of the individual antibodies. Monoclonal and affinity purified polyclonal antibodies need a much lower concentration compared to total IgG purified from immunsera. The slide was gently agitated and incubated at room temperature for 10 minutes. Agglutination was observed using a Motic System Microscope (B1 Series) at a 10×-40× magnification.

Results are shown in FIG. 8A

Example 11

Direct FimA Pull Down Assay

A 20 µl bed volume of protein A beads (POROS® MabCapture™, Applied Biosystems®, CA, USA) was washed twice in 1 ml PBS by centrifugation (300 g, 1 min) and removal of the supernatant. Beads were coated with antibody by incubating beads with 10 µg antibody in 0.2 ml PBS for 30 minutes and 30 rpm at room temperature. Beads were washed again twice in 1 ml PBS and beads were taken up in 0.4 ml supernatant of a LB overnight culture of *A. baumannii*. Supernatant was prepared by centrifugation of the bacterial culture at >4000 g for 5 minutes and supernatant was filtered through a 0.2 µm filter for syringes (Nalgene #194-2520). The mixture was incubated for 1 h and 30 rpm at room temperature. Beads were washed again twice in 1 ml PBS. Finally, beads were resuspended in 30 µl lysis buffer for NuPAGE® 4%-20% Bis-Tris gels (NP0322BOX, Invitrogen) and incubated at 98° C. for 5 min. The sample was tested for presence of native FimA by immunoblot analysis as described above according to the manufacturer's instructions for denatured, reduced 4%-20% Bis-Tris gels using MES running buffer (IM-8042 Version H, Invitrogen). Rabbit immune serum against FimA was used for detection of FimA.

Results are shown in FIG. 11.

Example 12

Active and Passive Immunization in Animals

Active and passive immunization studies were performed using the mouse *Acinetobacter pneumonia* model using as read outs percentage survival, clinical scores and body weights previously developed by Eveillard et al., 2010, *Journal of Infection* 60 (2), S. 154-161.

12.1 Active Immunization

On days 0, 14, 28, 42, each mouse (135 C3H/HeN mice, 18-20 g, 6 weeks old. Elevage Janvier, Sarthe, France) was immunized intra peritoneal with 10 µg antigen in 0.1 ml 50% (v/v) Gerbu adjuvant (GERBU Biotechnik GmbH, Germany)/PBS. As negative controls, mice were either immunized with 50% (v/v) Gerbu adjuvant/PBS or PBS only.

On day 49, the pneumonia model was started according to the established protocols at the laboratory of Marie Laure Joly-Guillou and Matthieu Eveillard (Eveillard et al., *Journal of Infection* 60 (2), S. 154-161, 2010). Briefly, the mice were rendered transiently neutropenic by injecting cyclophosphamide (Baxter, Ill., USA) by intra-peritoneal injection (150 mg/kg body weight in 0.15 ml) on days 4 and 3 before *A. baumannii* inoculation. The mice were anesthetized by isoflurane in conjunction with pure oxygen. Intratracheal instillation of *A. baumannii* was performed as previously described (Joly-Guillou et al., *Antimicrob Agents Chemother*. February; 41(2):345-51, 1997). Briefly, the trachea was canulated with a blint needle and 50 µl of a bacterial suspension containing $10^8$ cfu/mL were deposited. Inoculum size was confirmed by quantitative culture.

After intra-tracheal instillation of the inoculums, the mice were returned to their cages (day 0) and observed to assess spontaneous outcome. This outcome was evaluated daily (including day 0) and concerned mortality, mouse weight changes, and a clinical score built on the basis of mice mobility (score=0 for a spontaneous mobility, score=1 when a mobility was only observed after stimulation, and score=2 for an absence of mobility), the development of a conjunctivitis (score=0 in the absence of conjunctivitis, score=1 when there was a conjunctivitis), and the aspect of hair (score=0 for a normal hair and score=1 for ruffled hair). Overall, this clinical score varies from 0 for normal mice to 4 for severe illness.

Results are shown in FIG. 12.

12.2 Passive Immunization

The pneumonia model was started according to the established protocols at the laboratory of Marie Laure Joly-Guillou and Matthieu Eveillard (Eveillard et al., *Journal of Infection* 60 (2), S. 154-161, 2010.). Briefly, the mice were rendered transiently neutropenic by injecting cyclophosphamide by intra-peritoneal injection (150 mg/kg body weight in 0.15 ml) on days 4 and 3 before *A. baumannii* inoculation. On the day 0, 3 h before *A. baumannii* inoculation, mice were passively vaccinated intraperitoneally with either 0.15 ml rabbit antiserum, naïve rabbit serum or PBS. Pneumonia was induced analogous to the active immunization protocol starting with anesthetization of the mice. Analogous, survival, clinical score and body weight were monitored. Results are shown in FIGS. 11 and 13.

Example 13

Generation of mAbs

Peripheral blood lymphocytes purified by Ficoll-Paque gradient centrifugation from 40 ml whole blood samples are resuspended in 3 ml cell culture medium (IMDM/Ham's F12 50:50; 10% FCS) and 3 ml cellculture supernatant of EBV-secreting B-95-8 marmoset cells. After incubation for 3 to 15 hours at 37° C. and 6.5% $CO_2$, loose and adherent cells are transferred after one washing/centrifugation step in HANKS buffer into 18 ml cell culture medium containing 1 µg/ml Cyclosporin A+/−supplements. Cells are seeded in 96 well round bottom plates in volumes of 200 µl per well and cultivated for 1 to 3 weeks until fast growing colonies, lymphoblastoid cell lines (LCL), can be identified and the medium turns yellow due to pH shifting. Cell supernatants are analyzed for antigen-specific antibodies by ELISA. Antibody-producing cells are afterwards passaged until cell numbers sufficient for the following fusion procedure are obtained. $2.5×10^5$ or $1.25×10^5$ LCL and the same amount of fusion partner cells (e.g. mouse-human heteromyeloma LA55) are used for one electrofusion. Cells are harvested when growing exponentially and washed once with PBS and afterwards with electrofusion buffer. The LCL supernatant is stored at 4° C. and later used as a positive control in screening ELISAs. After combining the two cell types, cells are spinned down and the emerged pellet is carefully resuspended in 200 µl electrofusion buffer. For fusion, the cell mixture is transferred to the Helix-Fusion chamber of a Multiporator (Eppendorf) and the cell fusion program (Alignment: 5 Volt, 30 sec; Pulse: 30 Volt, 30 sec, No. Pulse: 3; Post-Alignment: 5 Volt, 30 sec) is applied. Afterwards the cells are incubated at room temperature for 5 to 10 minutes, resuspended in 4 ml cell culture medium without FCS and dispensed in 4 wells of a 24-well plate. After 3 hours of incubation at 37° C. and 6.5% $CO_2$ the cell suspensions are pooled, mixed with 4 ml selection medium and transferred to a 96-well round-bottom plate (200 µl/well). After one week the medium is replaced by cell culture medium without selective reagents. Afterwards cells are cultivated until fast growing hybridoma colonies can be identified. Then the supernatants are analyzed for the presence of specific antibodies by ELISA. The identified hybridoma are grown up, re-cloned by two time single cell cultivation and cryopreserved for development.

Example 14

Bactericidal Assay

HL-60 cells (ATCC CCL-240) were cultivated in IMDM (Sigma-Aldrich) or RPMI-1640 (Sigma-Aldrich), each containing 20% (v/v) heat inactivated (40 min at 56° C.) fetal bovine serum (FCS) (Biochrome, Berlin, Germany) and 2 mM GlutaMAX-I (Gibco/Invitrogen, USA) at 37° C. in a 6% $CO_2$ cell culture incubator. Cells were maintained at a cell density between $10^5$-$10^6$ cells/ml by passaging cells every 3-4 days into a fresh cell culture flask and replacing 80%-90% of the cell culture with fresh media. HL-60 cells were not cultivated longer than 4 months.

Four days in advance of the bactericidal assay, the HL-60 cells were differentiated by addition of 310 µl dimethylformamide (Sigma-Aldrich, Germany) to $8×10^6$ HL-60 cells in 40 ml medium. The cells were incubated for 4 days at 37° C.

On the day of the bactericidal assay, overnight cultures of *A. baumannii* in LB were diluted 1:150 in 3 ml fresh LB medium and incubated for 3 h at 37° C. and 200 rpm until an $OD_{600}$ of 0.5-1.5 was reached. The culture was diluted to an $OD_{600}$ of $3.8×10^{-6}$ in to room temperature prewarmed IMDM containing 0.1 (w/v) % BSA. Antibodies or serum and corresponding controls were equally diluted in PBS. Each diluted antibody (20 µl) was combined with 80 µl bacterial suspension in a well of a 96-well cell culture plate. The concentration of antibody depended on the *A. baumannii* strain, serum and antibody used. Antibody (0.5 µg/well for ATCC 19606 and CsuE KO, 5 µg/well for Ruh134) of total IgG from rabbit immune serum (αCsuAB) or naive rabbit serum was used.

Antibody and bacteria were incubated at 37° C. and 130 rpm for 20 min. Differentiated HL-60 cells (60 µl) or medium and 20 µl baby rabbit serum (BRS) (Charles River Wiga GMBH, Germany) as complement or BRS previously heat inactivated by incubating for 40 min at 56° C. (HBRS) were added and wells incubated at 37° C. and 130 rpm for 120 min. Colony forming units (cfu) were determined as follows. Each well was resuspended thoroughly and 10 µl of undiluted suspension and a 1:5 diluted suspension were plated onto LBA. LBA-plates were incubated at 37° C. and cfus were counted 16-20 h later.

Results are shown in FIGS. 9 A and B.

Example 15

Peptide/Epitope Mapping

Peptide mapping of rabbit immune sera and the corresponding pre-immune sera were performed by Pepperprint GmbH (Heidelberg, Germany) by microarray analysis. From the Seq ID NOs 2, 4, 6, 8, 10, 12, 14 and 16, all possible linear peptide fragments consisting of 5, 8 and 15 amino acids were synthesized. Fragments were coated onto PEGMA copolymer film with a linker of two β-alanines and aspartic acid. The microarrays consisting of peptide fragments from Seq ID NOs 2, 4, 6, 8, 10, 12, 14 and 16 in duplicate were stained with rabbit pre-immune and specific immune sera that were raised against the corresponding recombinant proteins (e.g. Microarray coated with peptide fragments of Seq ID NO 2 was stained with pre-immune and immune serum of a rabbit immunized with recombinant protein of Seq ID NO 2). The generation of recombinant proteins is described in Example 3 and 4. The generation of the immune sera is described in Example 5. The antibody staining procedure was performed as follows: after 30 min pre-swelling in standard buffer (PBS, pH 7.4+0.05% Tween 20) and 30 min in blocking buffer (Rockland blocking buffer B-070), the peptide microarrays with the coated peptide fragments were incubated with rabbit pre-immune sera at a dilution of 1:1000 for 16 h at 4° C. and shaking at 500 rpm. After washing in standard buffer twice for 1 min, the microarrays were stained with the secondary goat anti-rabbit IgG(H+L) DyLight680 antibody at a dilution of 1:5000 for 30 min at room temperature. The peptide microarrays were washed twice for 1 min with standard buffer, rinsed with distilled water and dried in a stream of air. Read-out was done with Odyssey Imaging System at a resolution of 21 μm and green/red intensities of 7/7. After the read out, the staining procedure was repeated with the corresponding immune serum starting with the pre-swelling step. The incubation in blocking buffer was skipped. The signal intensities of the corresponding pre-immune and immune sera were compared. A software algorithm from the PepSlide® Analyzer was used to calculate the median staining intensity of each peptide, duplicates averaged and the standard deviation calculated. Based on average intensities, an intensity map was generated and specific binders in the peptide map identified. Peptide and intensity maps were correlated with visual inspection of the microarray scans to identify consensus motifs and distinctive peptides that interacted specifically with the rabbit immune sera.

Results Example 15

To verify the immunogenicity of peptide fragments, microarray analysis was performed as described in Example 15. The Seq ID NOs 2, 4, 6, 8, 10, 12, 14 and 16 were translated into linear peptide fragments consisting of 5, 8 and 15 amino acids and interaction analyzed with specific rabbit immune sera. By this approach for all rabbit immune sera, antibody epitopes were identified with varying lengths. Most consensus motifs consisted of 5 amino acids, while others were 6, 7 or 8 amino acids in length. The pre-immune sera used as control showed only negligible background. Based on the fragment, consisting of 8 amino acids, the immune serum specific to Seq ID NO 14 showed a single epitope consensus motif PVDFTVAI (SEQ ID NO: 36) and thus shows monoclonal reactivity.

The invention claimed is:

1. An antibody that specifically binds to the epitope consensus motif PVDFTVAI shown in SEQ ID NO: 36; wherein said antibody is an IgG capable of inducing an effector function towards *Acinetobacter baumannii*.

2. An antibody or antigen-binding fragment thereof that specifically binds to the epitope consensus motif PVDFTVAI (SEQ ID NO: 36).

3. The antibody of claim 2, wherein the antibody is human.

4. The antigen-binding fragment of claim 2.

5. An eukaryotic expression host cell capable of producing the antibody of claim 2.

6. A hybridoma capable of producing the antibody of claim 2.

* * * * *